(12) United States Patent
Spitzer et al.

(10) Patent No.: US 7,075,501 B1
(45) Date of Patent: *Jul. 11, 2006

(54) HEAD MOUNTED DISPLAY SYSTEM

(75) Inventors: Mark B. Spitzer; Ronald Gale, both of Sharon, MA (US); Jeffrey Jacobsen, Hollister, CA (US)

(73) Assignee: Kopin Corporation, Taunton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 993 days.

(21) Appl. No.: 08/384,237

(22) Filed: Feb. 6, 1995

Related U.S. Application Data

(63) Continuation-in-part of application No. 07/971,352, filed on Nov. 4, 1992, now abandoned, which is a continuation-in-part of application No. 07/944,207, filed on Sep. 11, 1992, now Pat. No. 5,444,557, which is a continuation-in-part of application No. 07/823,858, filed on Jan. 22, 1992, now abandoned, which is a continuation-in-part of application No. 07/643,552, filed on Jan. 18, 1991, now Pat. No. 5,300,788, which is a continuation-in-part of application No. 07/872,297, filed on Apr. 22, 1992, now Pat. No. 5,317,436, which is a continuation-in-part of application No. 07/636,602, filed on Dec. 31, 1990, now Pat. No. 5,206,749.

(51) Int. Cl.
*G09G 5/00* (2006.01)

(52) U.S. Cl. .............................. 345/8; 345/87
(58) Field of Classification Search ................ 345/6–8, 345/102; 359/54, 55, 59
See application file for complete search history.

(56) References Cited

U.S. PATENT DOCUMENTS

| | | | | |
|---|---|---|---|---|
| 3,375,375 A | | 3/1968 | Abbey et al. | |
| 4,028,725 A | | 6/1977 | Lewis | 358/103 |
| 4,034,401 A | | 7/1977 | Mann | 358/93 |
| 4,109,145 A | | 8/1978 | Graf | 250/201 |
| 4,181,405 A | | 1/1980 | Cohen | 350/174 |
| 4,287,809 A | | 9/1981 | Egli et al. | 89/41 |
| 4,361,384 A | | 11/1982 | Bosserman | 350/174 |
| 4,368,523 A | * | 1/1983 | Kawate | 350/333 |
| 4,562,478 A | * | 12/1985 | Hirasawa et al. | 345/102 |
| 4,636,866 A | * | 1/1987 | Hattori | 345/8 X |
| 4,869,575 A | * | 9/1989 | Kubik | 345/8 |
| 5,093,567 A | | 3/1992 | Staveley | 250/221 |
| 5,095,304 A | * | 3/1992 | Young | |

FOREIGN PATENT DOCUMENTS

| | | | |
|---|---|---|---|
| DE | 2715446 | | 10/1978 |
| FR | 2522804 | | 9/1983 |
| FR | 2612351 | | 9/1988 |
| GB | 2206979 | * | 1/1989 |
| JP | 54093378 | | 7/1979 |
| JP | 60046019 | | 3/1985 |
| JP | 1259580 | | 10/1989 |
| WO | 91/04508 | | 4/1991 |
| WO | WO93/01583 | | 1/1993 |

OTHER PUBLICATIONS

Fracis A. Jenkins et al, Fundamentals of Optics, McGraw–Hill, 1976, pp 62, 330–332.*

Katz "Low Cost Helment Mounted Display and Eye Tracking Concepts" MaK Technologies, Inc . Presentation, May 15, 1991.

Wireless LAN's get boost from Motorola EDN, News Article Mar. 7, 1991.

* cited by examiner

*Primary Examiner*—Amare Mengistu
(74) *Attorney, Agent, or Firm*—Hamilton, Brook, Smith & Reynods, P.C.

(57) ABSTRACT

A head mounted display system including a high resolution active matrix display which reduces center of gravity offset in a compact design. The active matrix display can be either a liquid crystal display or a light emitting display.

25 Claims, 39 Drawing Sheets

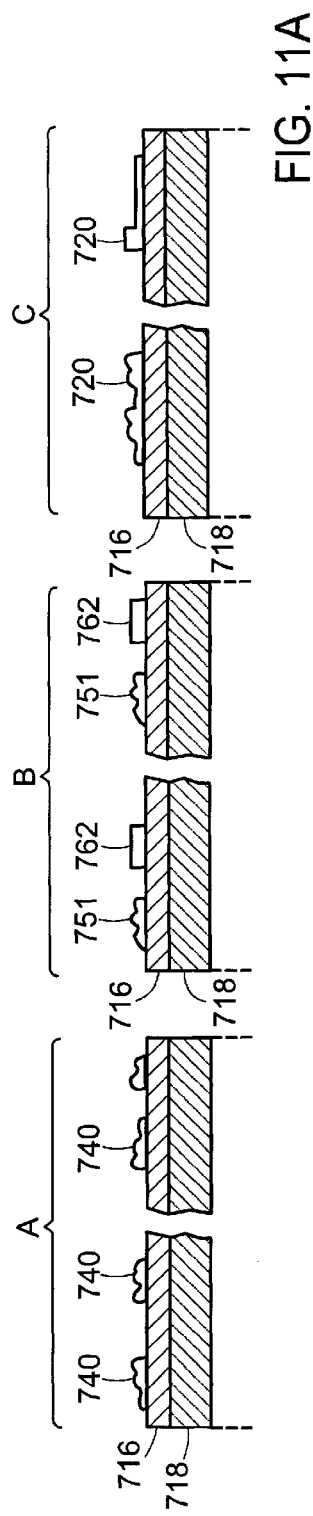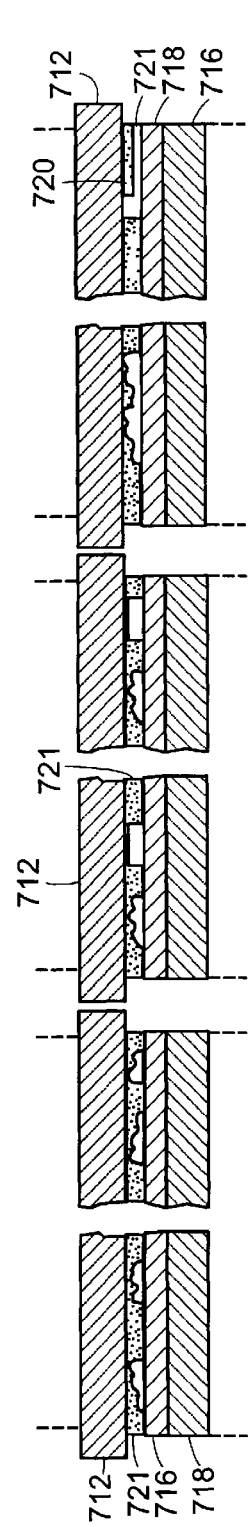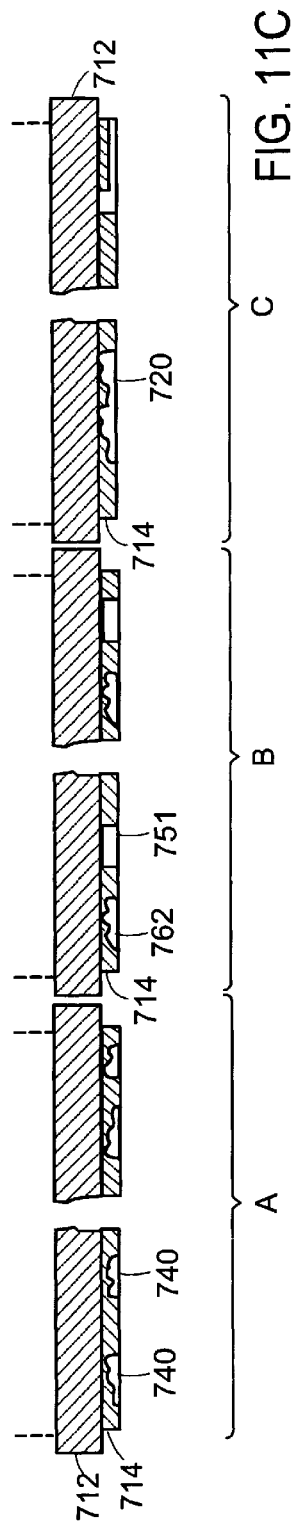

CROSS SECTIONAL VIEW      TOP VIEW
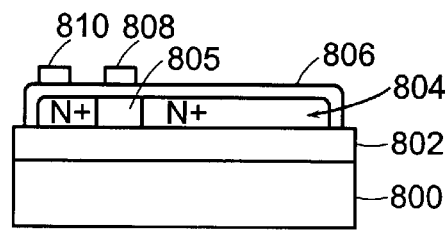 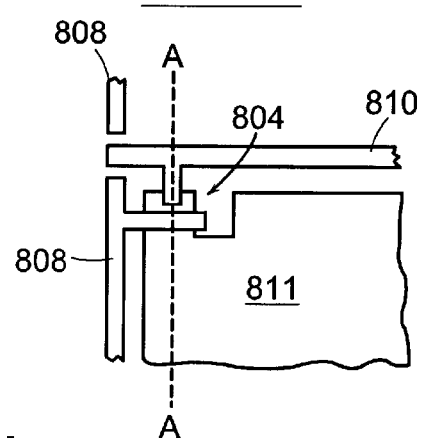
FIG. 12A
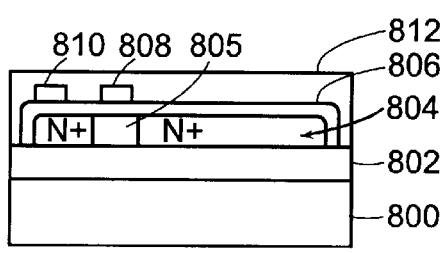 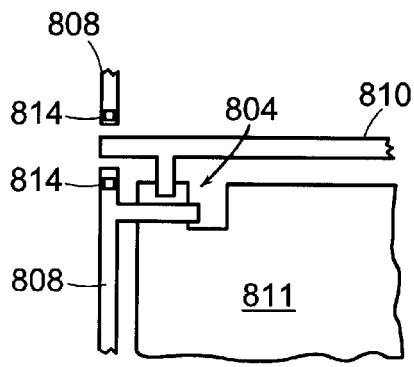
FIG. 12B
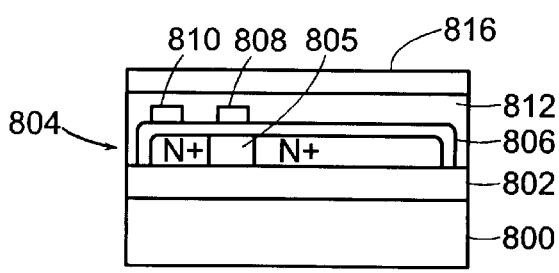 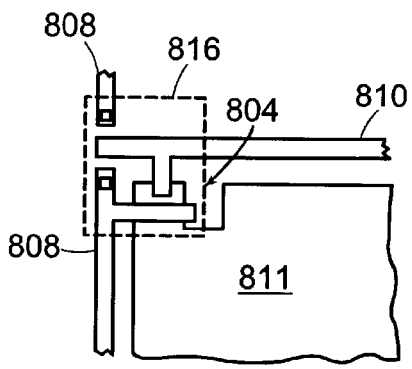
FIG. 12C

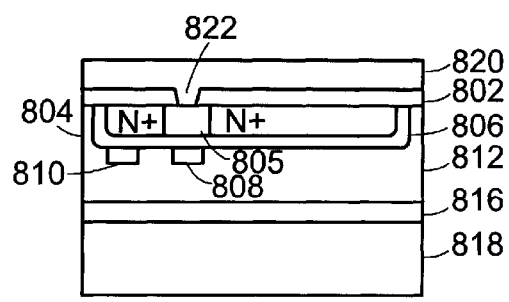
FIG. 12D
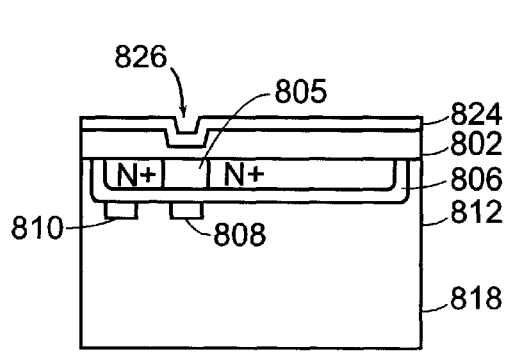
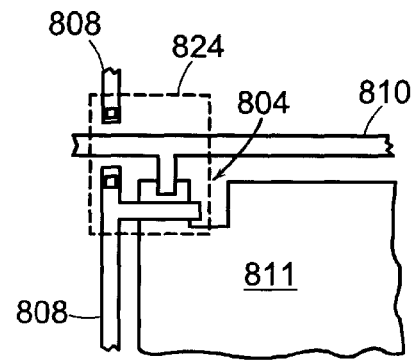
FIG. 12E

HEAD MOUNTED DISPLAY SYSTEM

RELATED APPLICATION

This is a Continuation of U.S. patent application Ser. No. 07/971,352 filed on Nov. 4, 1992, which is now abandoned, which is a continuation-in-part of application Ser. No. 07/944,207 filed on Sep. 11, 1992, now U.S. Pat. No. 5,444,557 which is a Continuation-In-Part application of U.S. Ser. No. 07/823,858 filed on Jan. 22, 1992 which is now abandoned and is also a Continuation-In-Part of U.S. patent application Ser. No. 07/643,552 filed on Jan. 18, 1991, now U.S. Pat. No. 5,300,788, and is also a Continuation-In-Part of U.S. patent application Ser. No. 07/872,297, filed Apr. 22, 1992, now U.S. Pat. No. 5,317,436, which is a Continuation-In-Part of U.S. patent application Ser. No. 07/636,602, filed Dec. 31, 1990, now U.S. Pat. No. 5,206,749, all of which are incorporated herein by reference.

BACKGROUND

Head mounted display systems have been developed for a number of different applications including use by aircraft pilots and for simulation. Head mounted displays are generally limited by their resolution and by their size and weight. Existing displays have relatively low resolution and are positioned at a relatively large distance from the eye. Of particular importance, is to keep the center of gravity of the display from extending upward and forward from the center of gravity of the head and neck of the wearer, where it will place a large torque on the wearer's neck and may bump into other instruments during use. There is a continuing need to present images to the wearer of a helmet mounted display in a high-resolution format similar to that of a computer monitor. The display needs to be as non-intrusive as possible, leading to the need for a lightweight and compact system.

SUMMARY OF THE INVENTION

The present invention uses a single-crystal material to produce a high-density active matrix array in a head mounted optical support system that provides for closeness of the display to the eye, compactness of the array and provides the desired level of resolution. With a density of 400 lines per centimeter, for example, a 1.27 centimeters display in accordance with the invention will fit into a system only 1.52 centimeters in depth. This system is more compact, has lighter weight, and a lower cost than existing head mounted displays.

To get the display system as close as possible to the eye and as compact as possible, a short focal length lens system must be used. The focal lengths of simple lenses are limited by lens geometry, where the thickness of the lens is less than the lens diameter. Thus, a simple lens has a shorter focal length as well as a small diameter. For the most compact system, the smallest possible lens that would focus the display image is used. The lens size is defined by the object size, which in this case is the size of the display element.

Since resolution needs to be increased while size needs to be decreased, the pixel density of the display needs to increase. Existing displays have pixel densities of about 120 lines per centimeter and are about 4.1 centimeters in diameter. Using a 3.81 centimeter lens, where the minimum focal length for a standard 3.81 centimeter lens is about 3.05 centimeters, results in a lens with a center thickness of over 1.52 centimeters. The use of this lens results in a lens-to-display distance of about 3.3 centimeters, which is the minimum depth of an existing head-mounted display for this geometry.

The present system, by increasing the pixel density to at least 200 lines per centimeter, and preferably to over 400 lines per centimeter, provides for a lens-to-display distance of less than one inch. The lens-to-display distance is preferably in the range of 1.0–2.2 centimeters.

The display can be a transmission type display with the light source directed adjacent the light valve active matrix or the light source can be positioned above the head of the user such that the light can be coupled to the light valve active matrix by one or more reflective elements.

Alternatively, the display can be an emission type device such as an active matrix electroluminescent display or an active matrix of light emitting diodes (LEDs).

Additional embodiments of the invention include a projected view active matrix display in which different polarization components of light are separated, one component being directed to the left eye, and another component being directed to the right eye. This provides a more efficient optical system in which more lift from the source is used to provide the desired image.

Another preferred embodiment utilizes an active matrix display in which the pixel size increases across the display to provide a wide angle field of view display.

The display can be fabricated as a visor with a number of displays which are tied together and positioned on a flat or curved plastic visor.

DETAILED DESCRIPTION OF THE DRAWINGS

The above, and other features of the invention including various novel details of construction and combination of parts, will now be more particularly described with reference to the accompanying drawings and that pointed out in the claims. It will be understood that the particular panel display and the methods used in fabricating those panels which embody the invention are shown by way of illustration only and not as a limitation of the invention. The principal features of this invention can be employed in various embodiments without departing from the scope of the invention.

FIGS. 11A–11C are another preferred process and transfer sequence for fabricating a light valve matrix and transferring it to a support structure.

FIGS. 12A–12E are yet another preferred process and transfer sequence for fabricating a matrix and transferring it to glass substrate.

Figure 3:
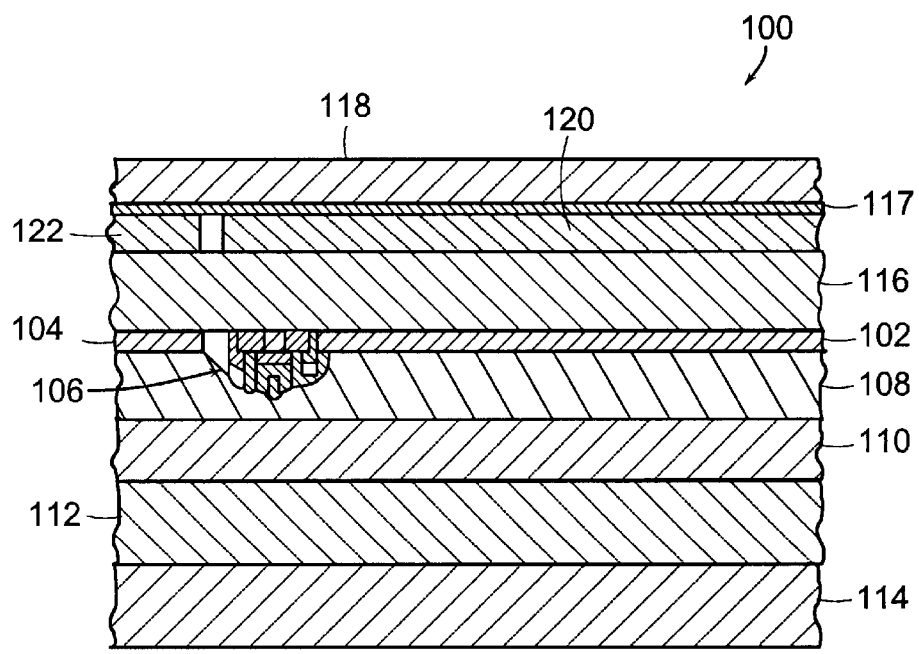
FIG. 3 is a cross-sectional view of a preferred embodiment of the display panel.
Figure 35:
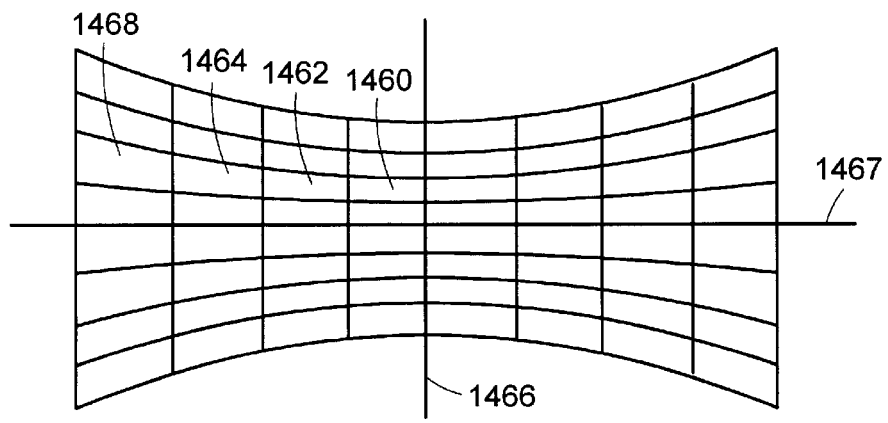

FIG. 35 provides a detailed view of a portion of the active matrix area of the device shown in FIG. 3.

Figure 36:
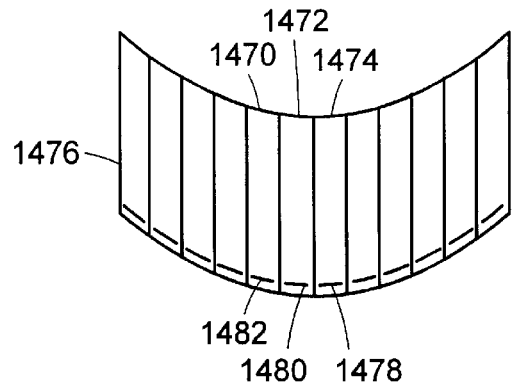

FIG. 36 provides a further embodiment wherein separate active matrix display elements are mounted or tiled onto a plastic visor screen. The visor screen can be polycarbonate, polyethylene or polyester material.

DETAILED DESCRIPTION

Figure 1A:
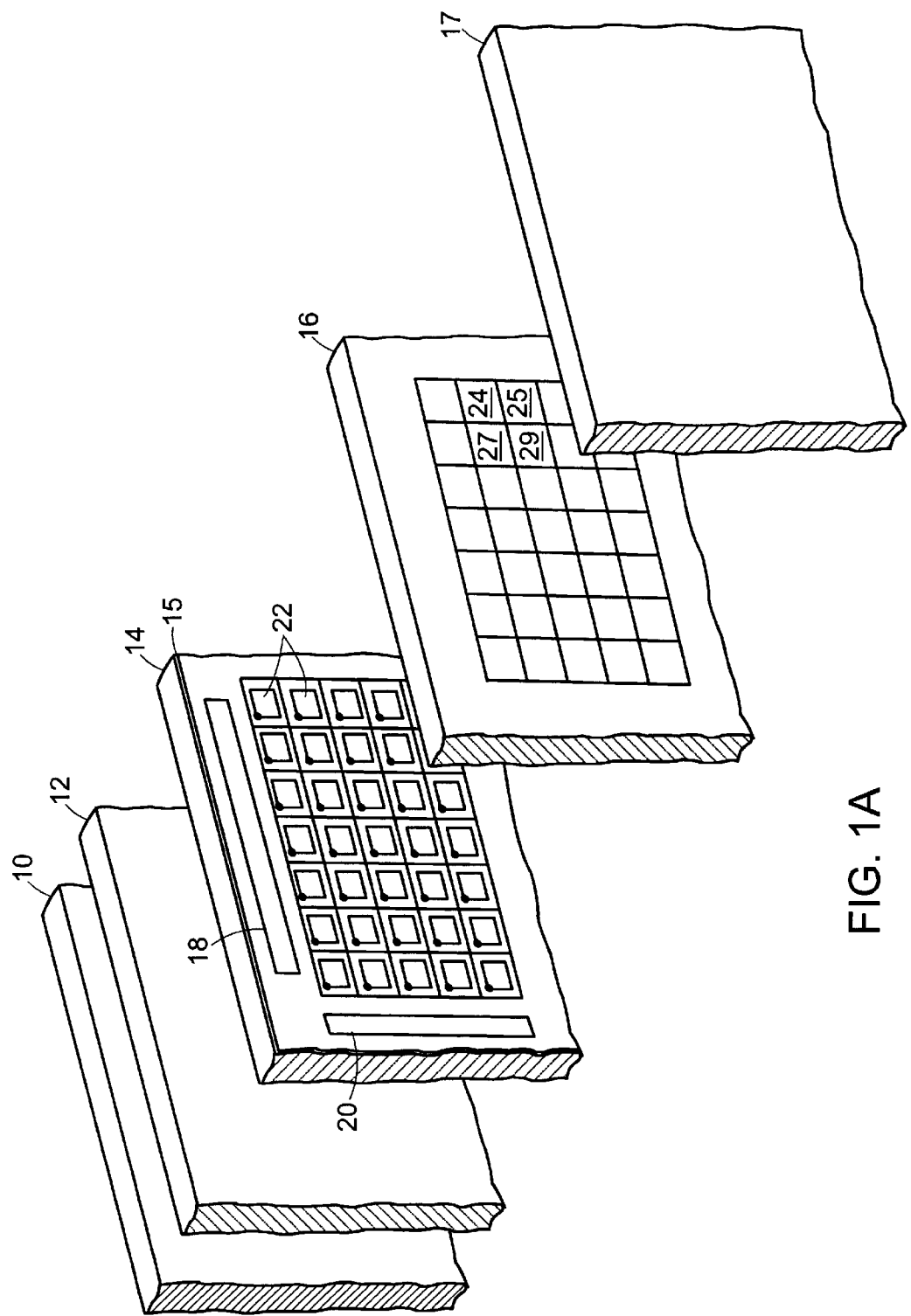
FIG. 1A is an exploded perspective view of a flat panel display.

A preferred embodiment of the invention is illustrated in the perspective view of a panel display in FIG. 1A. The basic components of the display include a light source 10 that can be white or some other appropriate color, a first polarizing filter 12, a circuit panel 14, a filter plate 16 and a second polarizing filter 17, which are secured in a layered structure. A liquid crystal material (not shown) is placed in a volume between the circuit panel 14 and the filter plate 16. An array of pixels 22 on the circuit panel 14 are individually actuated by a drive circuit having first 18 and second 20 circuit components that are positioned adjacent the array such that each pixel can produce an electric field in the liquid crystal material lying between the pixel and a counterelectrode secured to the color filter plate 16. The electric field causes a rotation of the polarization of light being transmitted across the liquid crystal material that results in an adjacent color filter element being illuminated. The color filters of filter plate system 16 are arranged into groups of four filter elements such as blue 24, green 25, red 27, and white 29. The pixels or light valves associated with filter elements 24, 25, 27, 29 can be selectively actuated to provide any desired color for that pixel group.

Other preferred embodiments employ the use of a solid state material to form a light valve for each pixel. A light emitting material such as an electroluminescent film or any material whose optical transmission properties can be altered by the application of an electric field can be used to supply the light valves of the present invention.

Figure 1B:
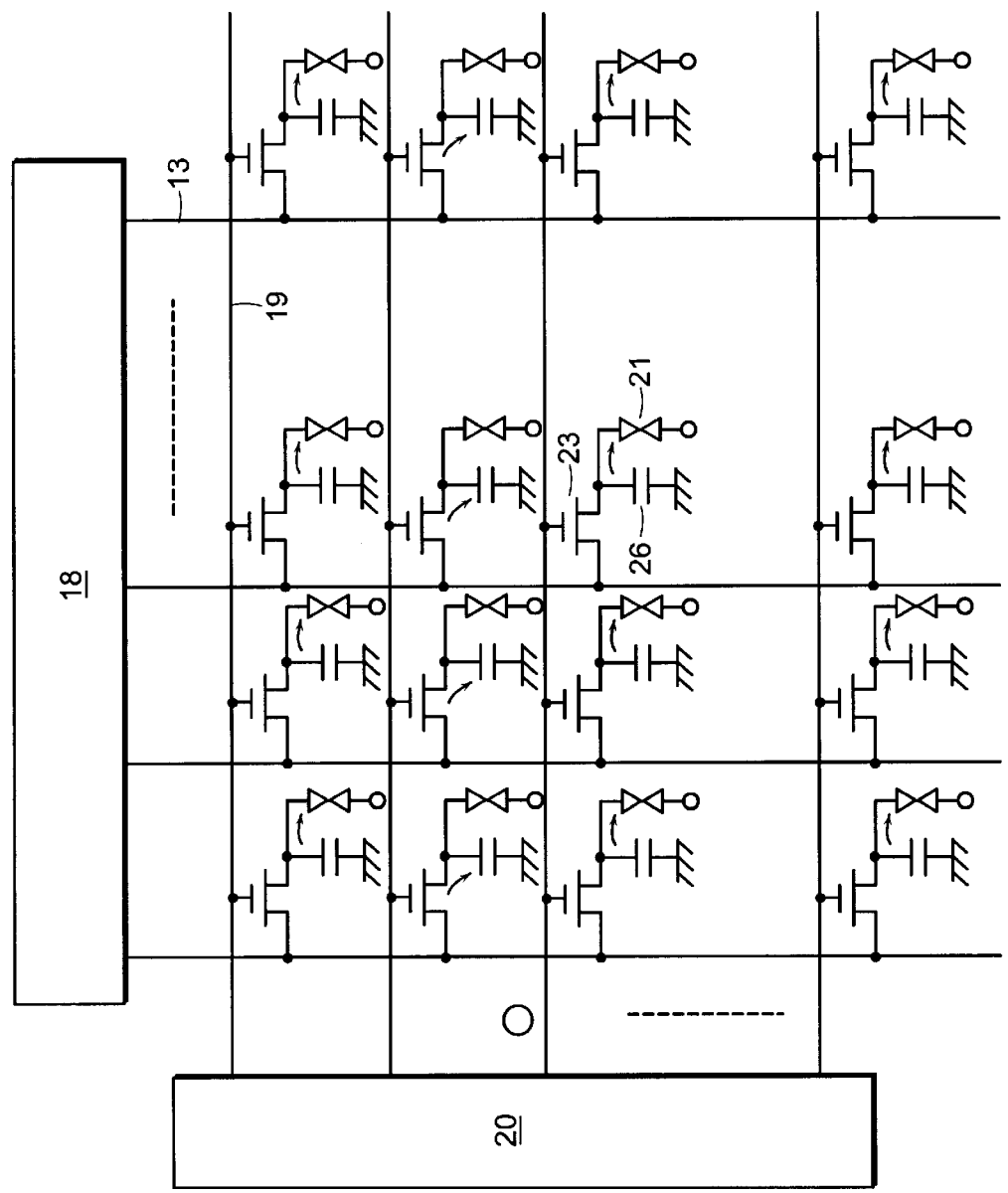
FIG. 1B is a circuit diagram illustrating the driver system for a flat panel display.

A drive circuit that can be used to control the display on the panel is illustrated in FIG. 1B. Circuit 18 receives an incoming signal and sends a signal to the pixels through buses 13. Circuit 20 will scan through buses 19 to turn on the individual transistors 23 which charges capacitor 26 in each pixel. The capacitor 26 sustains the charge on the pixel electrode and the liquid crystal 21 until the next scan of the array. The various forms of display systems may, or may not, utilize capacitors with each pixel depending upon the type of display desired.

FIGS. 2A–2L illustrate the use of an Isolated Silicon Epitaxy (ISE) process, to form silicon-on-insulator (SOI) films in which circuit panel circuitry is formed. Note that any number of techniques can be employed to provide a thin-film of single crystal Si. An SOI structure, such as that shown in FIG. 2A, includes a substrate 30 and an oxide 34 (such as, for example, $SiO_2$) that is grown or deposited on the substrate 30. A thin single crystal layer of silicon is formed over the oxide 34. The oxide (or insulator) is thus buried beneath the Si surface layer. For the case of ISE SOI structures, the top layer is a substantially single-crystal recrystallized Silicon, from which CMOS circuits can be fabricated. The use of a buried insulator provides devices having higher speeds than can be obtained in conventional bulk (Czochralski) material. Circuits containing in excess of 1.5 million CMOS transistors have been successfully fabricated in ISE material.

Figure 2A:
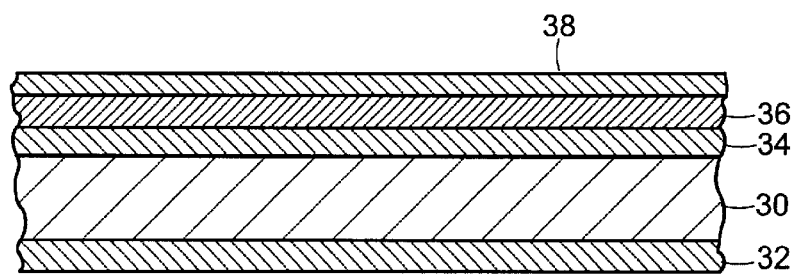
FIGS. 2A–2L is a preferred process flow sequence illustrating the fabrication of a circuit panel for a flat panel display.
Figure 2B:
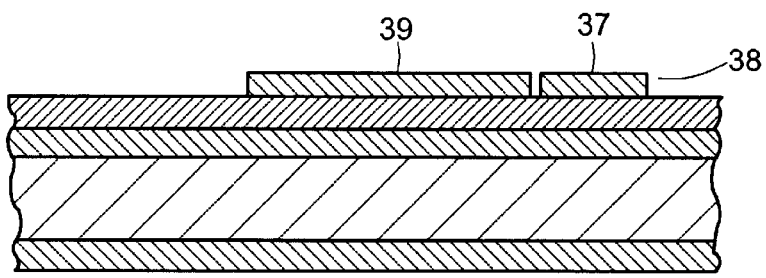
Figure 2C:
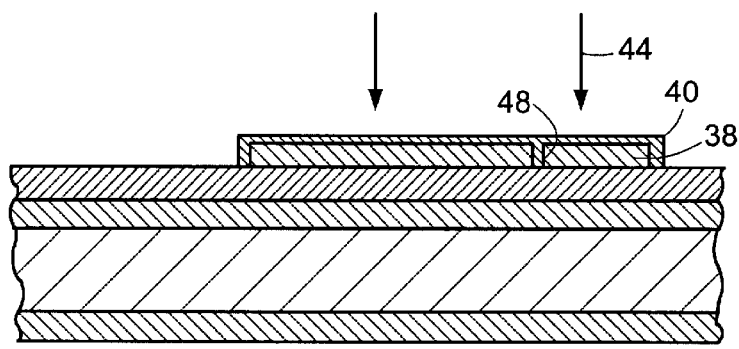

As shown in FIG. 2B, the film 38 is patterned to define a transistor region 37 and a pixel electrode region 39 for each pixel. An oxide layer 40 is then formed over the patterned regions including channel 48 between the two regions 37, 39 of each pixel. The intrinsic crystallized material 38 is than implanted 44 (at FIG. 2C) with boron or other p-type dopant to provide a n-channel device (or alternatively, an n-type dopant for an p-channel device).

Figure 2D:
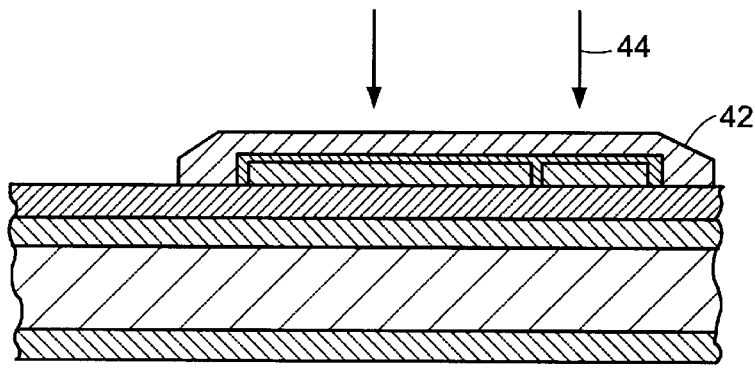
Figure 2E:
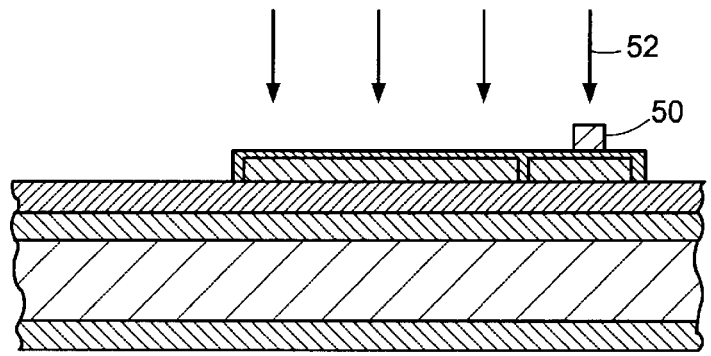
Figure 2F:
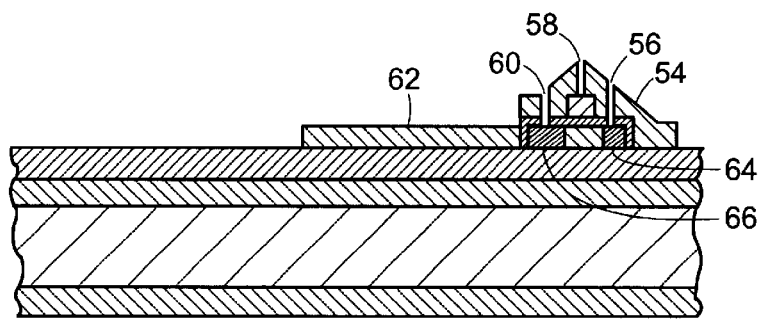
Figure 2G:
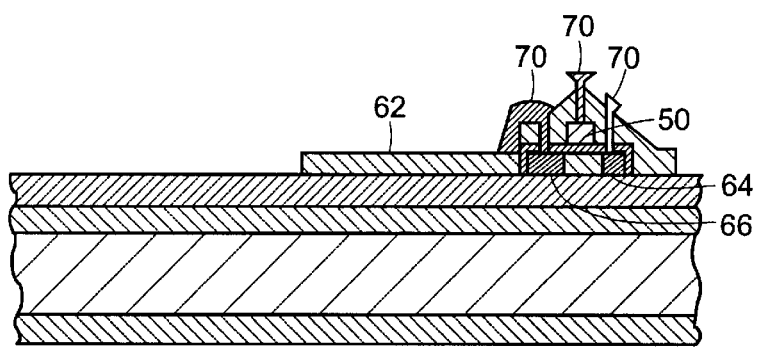
Figure 2H:
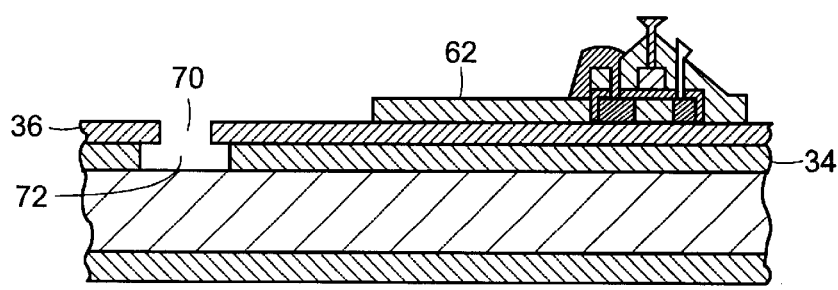

A polycrystalline silicon layer 42 is then deposited over the pixel and the layer 42 is then implanted 46, as seen in FIG. 2D, with an n-type dopant to lower the resistivity of the layer 42 to be used as a gate. The polysilicon is patterned to form the gate 50, as seen in FIG. 2E, which is followed by a large implant 52 of boron to provide p+ source and drain regions for the transistor. As shown in FIG. 2F, an oxide 54 is formed over the transistor and openings 60, 56, 58 are formed through the oxide 54 to contact the source 66, the drain 64, and the gate, respectively. A patterned metalization 70 of aluminum, tungsten or other suitable metal is used to connect the exposed pixel electrode 62 to the source 60 (or drain), and to connect the gate and drain to other circuit panel components.

A second fabrication procedure is one of the substrate release processes that have been developed to form thin (1 to 5 micron) films of processed silicon bonded to glass; these films contain active semiconductor devices such as FETs that are partially of completely fabricated prior to transfer. The crystallization and release procedures including the cleavage of laterally grown epitaxial films for transfer (CLEFT) approach are described more fully in U.S. Pat. No. 4,727,047 incorporated herein by reference. The chemical epitaxial lift-off (CEL) approach is described more fully in U.S. Pat. Nos. 4,846,931 and 4,883,561. Both of the CLEFT and CEL techniques permit the reuse of the substrate, leading to reduced cost compared to other approaches in which the substrates are consumed. By combining thin film release techniques with SOI wafers, we will be able to form the required high quality films and circuits on glass.

The foregoing indicates that CEL processes can be limited by the lateral distance that is required for the HF (or other etchant) undercut of the release layer. The key to large area panels using CEL is the release layer. The key to large area panels using CEL is the release of patterned devices and/or circuits rather than complete large-area films, because the circuits or devices have unused areas that can be used as vertical channels through the film to allow the etch to reach the release layer. This approach is illustrated in FIGS. 2H–2L. To remove the circuit from the release substrate a first opening 70 (in FIG. 2H) is formed in an exposed region of layer 36 that occurs between pixels. A second larger portion of layer 34 is than removed to form cavity 72 such that a portion of layer 36 extends over the cavity 72.

Figure 2I:
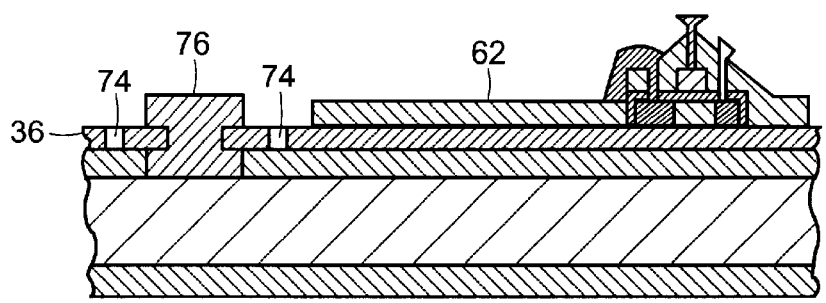
Figure 2J:
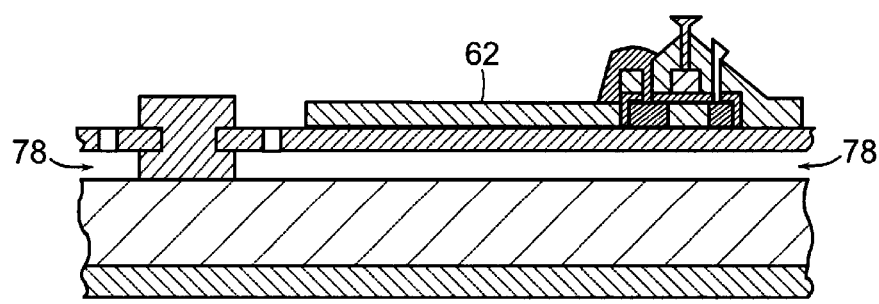
Figure 2K:
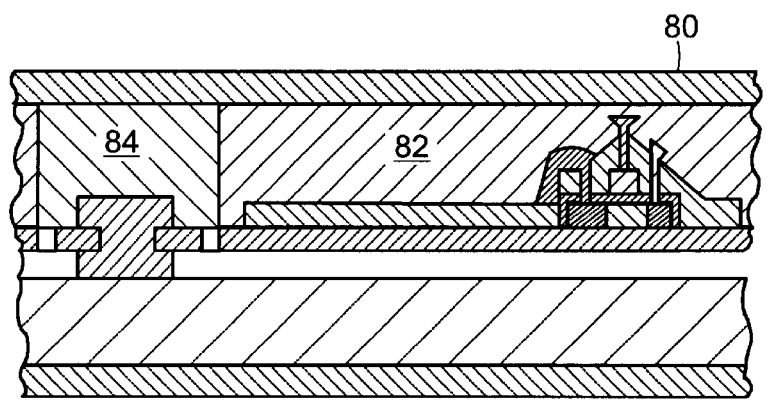

In FIG. 2I, a support post 76 is formed to fill cavity 72 and opening 70, and which extends over a portion of layer 36. Openings or via holes 74 are then provided through layer 36 such that an etchant can be introduced through holes 74, or lateral openings 78, to remove layer 34 (see FIG. 2J). The remaining insulating layer 36 and the circuitry supported thereon is now held in place relative to substrate 30 with support posts 76.

An epoxy that can be cured with ultraviolet light is used to attach an optically transmissive substrate 80 to the circuitry, and layer 36. The substrate 80 is than patterned such that regions of epoxy 82 is cured (see FIG. 2K). The substrate 30 and posts 76 are removed to provide the structure shown in FIG. 2L, which is than processed to provide the desired display panel.

Note that the UV-cured adhesive (or tape) can be patterned to protect the circuits where necessary, and HF can be used to reach the remaining the release layer.

Note that where the tape is used, tape provides support to the circuits after release. Large area GaAs devices containing films have been fabricated in this way, and these have been released to form devices from entire wafers on one tape. The released circuits can be remounted on the glass and the other elements of the liquid crystal display panel. Transparent adhesives are the preferred method of mounting.

Figure 2L:
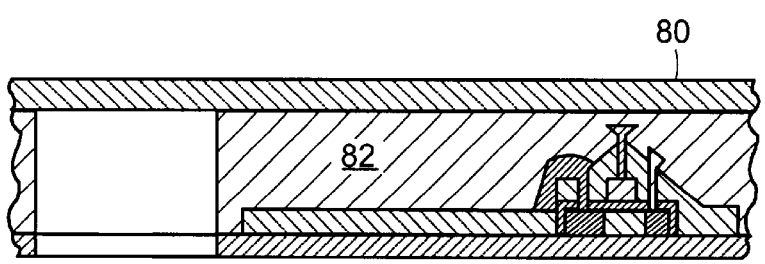

To form the final display panel the circuit panel shown in FIG. 2L is etched leaving the desired pixel elements exposed. Insulation and alignment layers, spacers, a sealing border and bonding pads for connections as added onto the circuit panel. A screen printing process can be used to prepare the border. The plate containing the color filters and the counterelectrode is sealed to the circuit panel with the sealing border after insertion of spacers. The display is filled with the selected liquid crystal material via a small filling hole or holes extending through the border. This filling hole is then sealed with a resin or epoxy. First and second polarizer films or layers are than bonded to both sides and connectors are added. Finally, a white light source 114, or other suitable light source, is coupled to polarize 112.

A cross-sectional view of the resulting device is shown in FIG. 3 wherein pixel electrodes 102 and 104 are laterally spaced from each other. Each pixel 102, 104 will have a transistor 106 and a color filter 120, 122 associated therewith. Polarizing elements 112, 118 are positioned on opposite sides of the structure which also includes bonding element or adhesive 108 and optically transmissive substrate 110, such as glass or plastic. Layer 108 can be a transparent epoxy or a low temperature glass that can have a thickness of 2–10 microns.

The CLEFT process permits the separation of a thin single-crystal films, grown by chemical vapor deposition (CVD), from a reusable homoepitaxial substrate. Unlike the CEL process, in the CLEFT process the circuits or devices are first bonded to glass and after mounting the separation is made between the circuits and the substrate.

The films removed from the substrate by CLEFT are essentially single-crystal, of low defect density, are only a few microns thick, and consequently the circuit panel has little weight and good transmission characteristics. For the purposes of the present application, the term "essentially single crystal" means a film in which a majority of crystals extend over a cross sectional area in a plane of the film of at least 0.1 cm$^2$, and preferably in the range of 0.5–1.0 cm or more.

The CLEFT process, illustrated in U.S. Pat. No. 4,727,047 involves the following steps: growth of the desired thin film over a release layer (a plane of weakness), formation of metallization and other coatings, formation of a bond between the film and a second substrate such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon the lateral epitaxy is accomplished by the ISE process or other recrystallization procedures. Alternatively, other standard deposition techniques can be used to form the necessary thin-film essentially single crystal material.

One of the necessary properties of the material that forms the release layer is the lack of adhesion between the layer and the semiconductor film. Since a weak plane has been created by the release layer, the film can be cleaved from the substrate without any degradation. The release layers can comprise multi-layer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated resulting in simpler handling as compared to W-cured tape.

In the ISE process, the oxide film is strongly attached to the substrate and to the top Si film which will contain the circuits. For this reason, it is necessary to reduce the strength of the bond chemically. This technique involves a release layer that is preferentially dissolved with an etchant without complete separation,to form a plane of weakness in the release layer. The films can then be separated mechanically after the glass is bonded to the circuits and electrodes.

Mechanical separation is accomplished as follows: The upper surface of the film is bonded with a transparent epoxy to a superstrate such as glass. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted on the glass. The substrate can then be used for another cycle of the CLEFT process, and the device processing is completed on the back surface of the film. Note that since the device remains attached to a superstrate, the back side can be subjected to standard wafer processing, including photolithography.

The method further involves the preparation of single crystal films, with seeding in the case of an Si substrate and without seeding for the case of foreign substrates. For the case of seeded Si films, the standard recrystallization process is employed. In either case, the bottom oxide or nitride layer can be optimized for release purposes.

Figure 4:
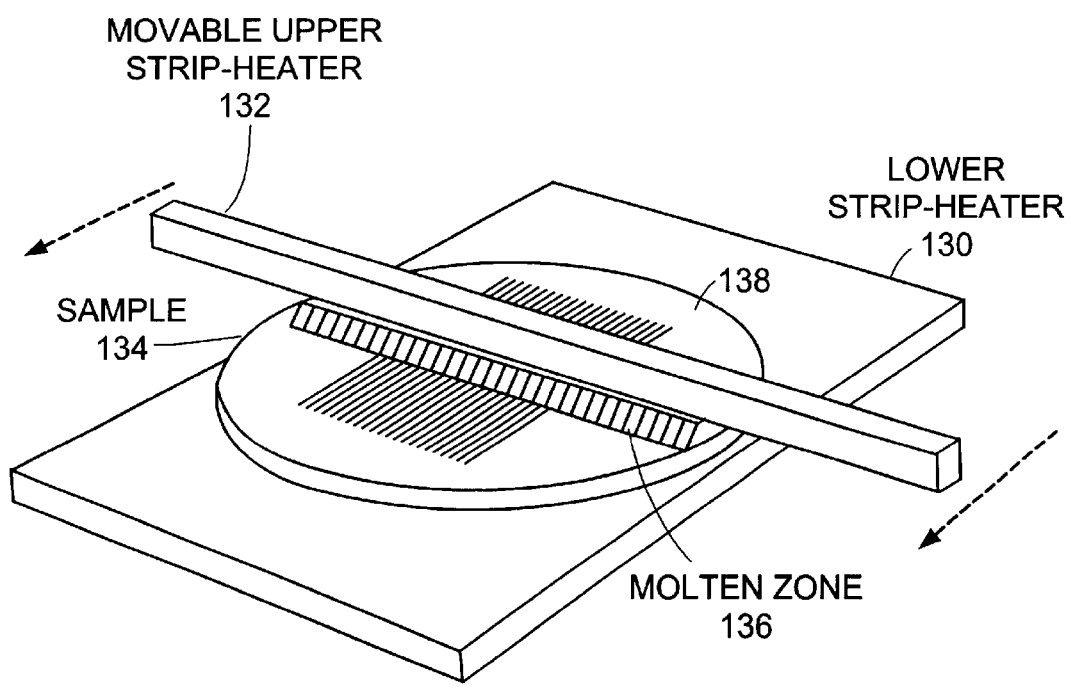
FIG. 4 illustrates in a perspective view a preferred embodiment of a system used for recrystallization.

In one embodiment of the recrystallization system, shown schematically in FIG. 4 the substrate temperature is elevated to near the melting point by a lower heater 130. An upper wire or graphite strip heater 132 is then scanned across the top of the sample 134 to cause a moving melt zone 136 to recrystallize or further crystallize the polycrystalline silicon. In the standard process on Si, the lateral epitaxy is seeded from a small opening through the lower oxide, and the resultant single crystal film has the orientation of the substrate. Capping layer 138 is deposited over the polycrystalline material prior to crystallization.

Figure 5A:
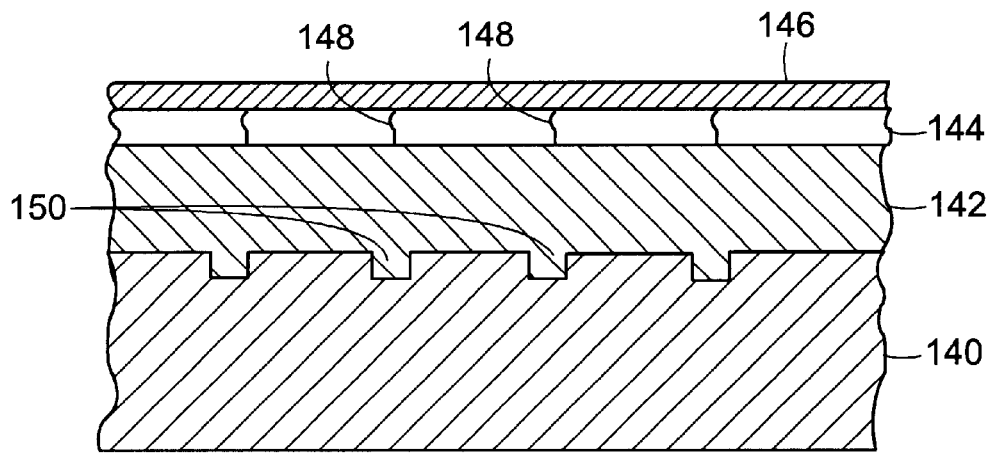
FIG. 5A illustrates the use of a patterned release layer to entrain boundaries in a crystallized material.

The use of foreign substrates precludes seeding. In this case, essentially single crystal Si is obtained by grain boundary entrainment techniques. Grain boundary entrainment can be used by patterning either the release oxide or the cap layer to introduce a modulation in the thermal gradients in the regrowth region. This modulation in the temperature field changes the location of the melt front and entrains the boundaries in predictable locations. Patterning of the release oxide 142 is shown in FIG. 5A. In this embodiment the substrate 140 has grooves 150 which are filled with the release oxide 142. Owing to this entrainment of boundaries 148 in the crystallized material 144 that can extend between the cap 146 and the release layer 142, the Si circuits or electrodes can be located in regions of high quality. Metallization and other features can be located over subgrain boundaries.

As shown, a preferable technique is to pattern the reusable substrate with the necessary entrainment structure. Once patterned in this way, the reusable substrate would not require repatterning. In such a scheme the entraining grooves are provided with a material of sufficient thickness to entirely fill the grooves. The material in the grooves could for example, comprise planarized $Si_3N_4$, while the release layer could comprise further deposition of $SiO_2$. Alternatively, the grooves could be filled entirely with $SiO_2$; the grooves could then function as channels for the release etch.

Figure 5B:
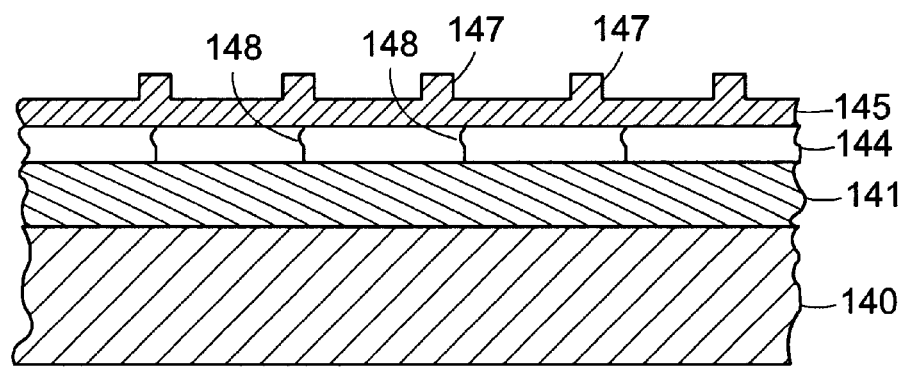
FIG. 5B illustrates the use of a patterned capping layer to entrain boundaries.

A second approach involves patterning the cap layer 145 after cap deposition, as shown in FIG. 5B. Patterned ridges 147 of the cap 145 overlie boundaries 148 in the recrystallized material that can extend between the cap 145 and release layer 141. A third approach would be to pattern the polycrystalline silicon layer.

Capping layers can be used with foreign substrates. The capping layer must be adherent throughout the thermal cycle, but must be removable for device processing. A cap works well for smooth Si substrates, but the patterned layers necessary for entrainment can require new films.

Figure 6A:
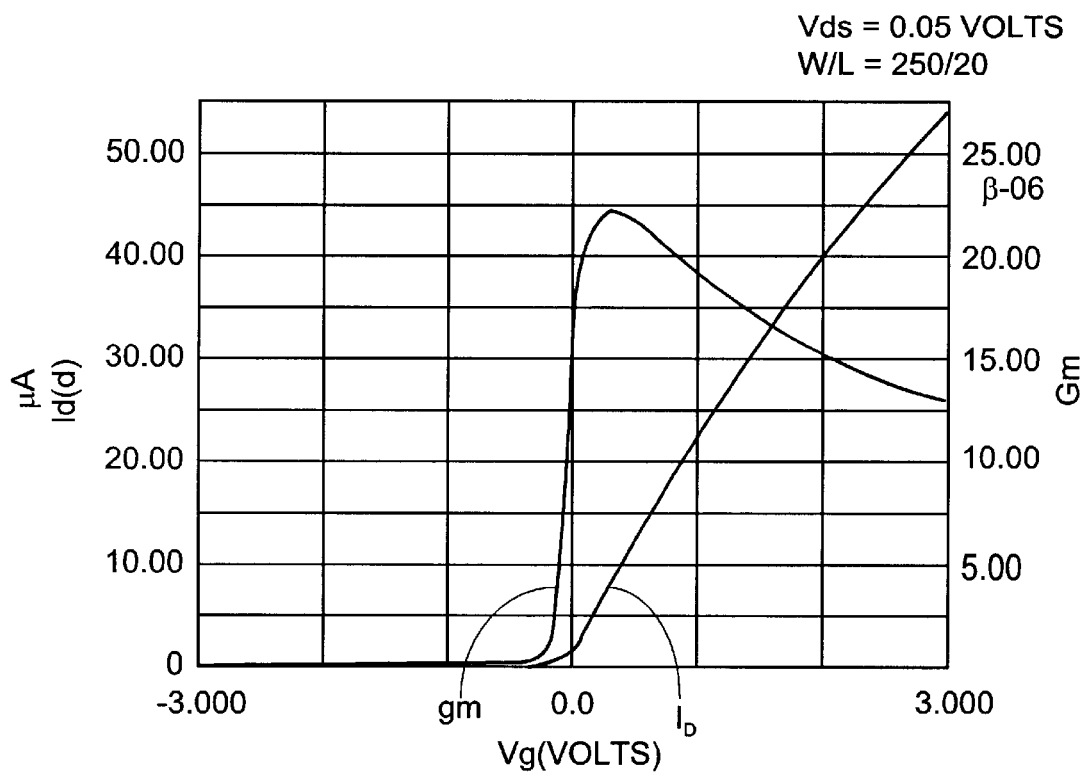
FIG. 6A illustrates the drain current and transconductance characteristics for a MOSFET prior to transfer to glass in accordance with the invention.
Figure 6B:
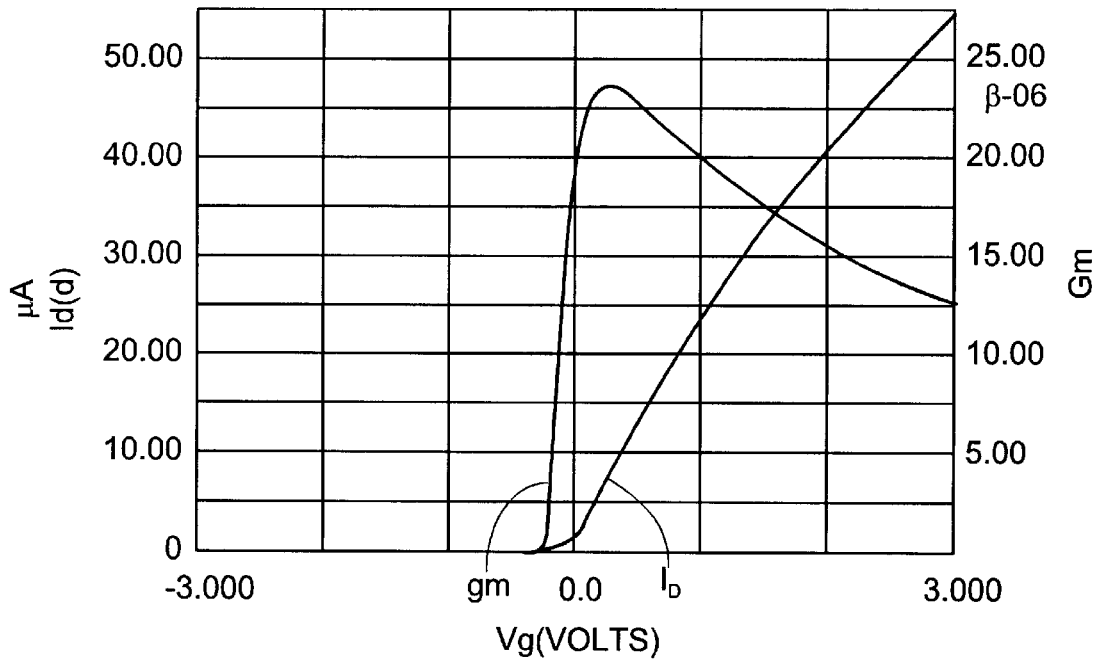
FIG. 6B illustrates the drain current and transconductance characteristics for the MOSFET of FIG. 6A after transfer to glass.

FIGS. 6–8 illustrate the electrical characteristics of a MOSFET made in accordance with the invention before and after transfer onto a glass substrate. FIG. 6A graphically depicts the drain current $I_D$ and the transconductance $G_M$ as a function of gate voltage $V_G$ in the linear region, where the drain-source voltage is 50 mV, for a MOSFET prior to transfer to glass. The MOSFET has a width-to-length ratio of 250 μm/20 μm and a gate oxide thickness of 890 A in a 0.5 μm thick recrystallized silicon material. FIG. 6B shows the drain current $I_D$ and transconductance $G_M$ of the same device after transfer to glass.

Figure 7A:
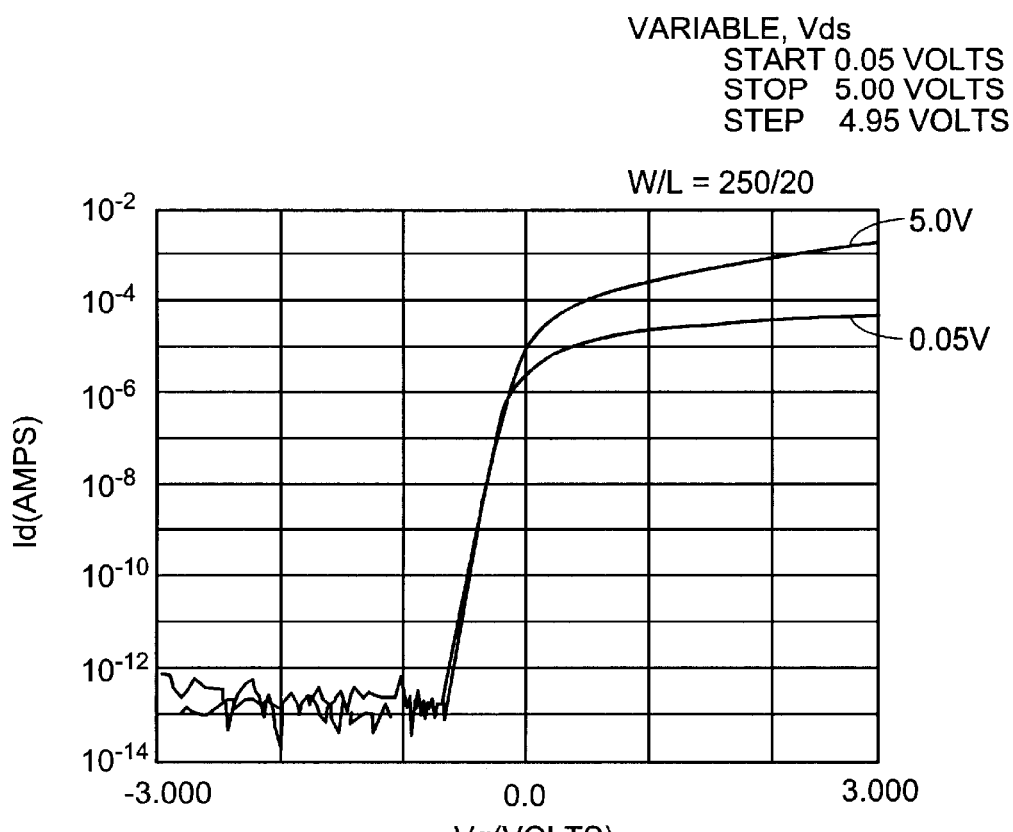
FIG. 7A illustrates the drain current of the device in FIG. 6A plotted on a logarithmic scale at two different drain voltages.

FIG. 7A graphically illustrates the drain current of the device of FIG. 6A plotted on a logarithmic scale at two drain-source voltages $V_{DS}$=50 mV and $V_{DS}$=5V.

Figure 7B:
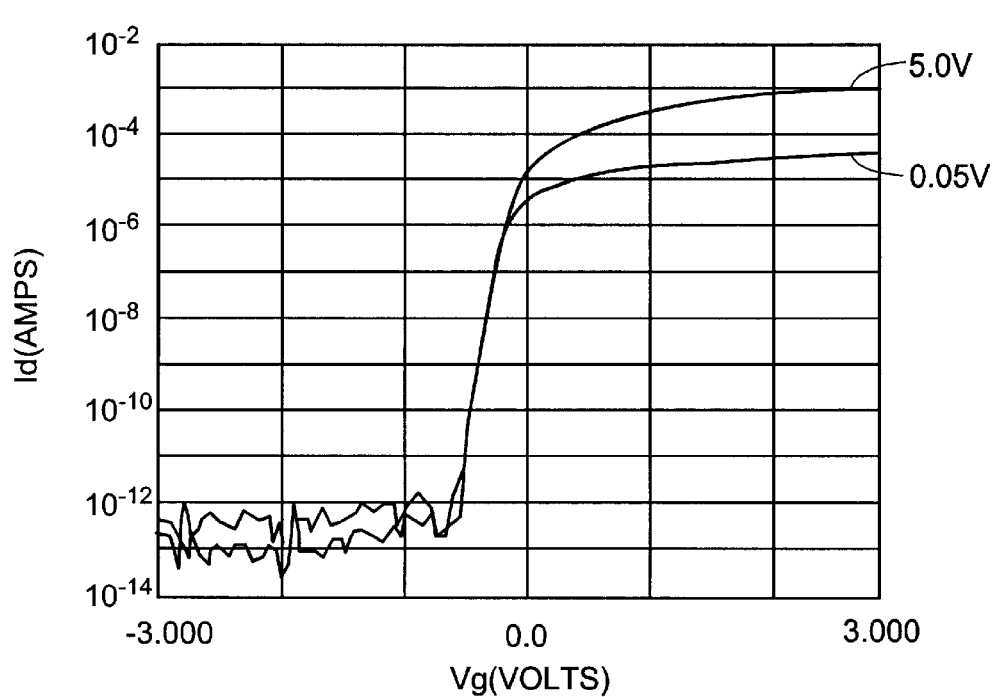
FIG. 7B illustrates the drain current of the device in FIG. 6B plotted on a logarithmic scale at two different drain voltages.

FIG. 7B graphically illustrates the drain current of the device in FIG. 6B plotted on a logarithmic scale at drain-source voltages of $V_{DS}$=50 mV and $V_{DS}$=5V.

Figure 8A:
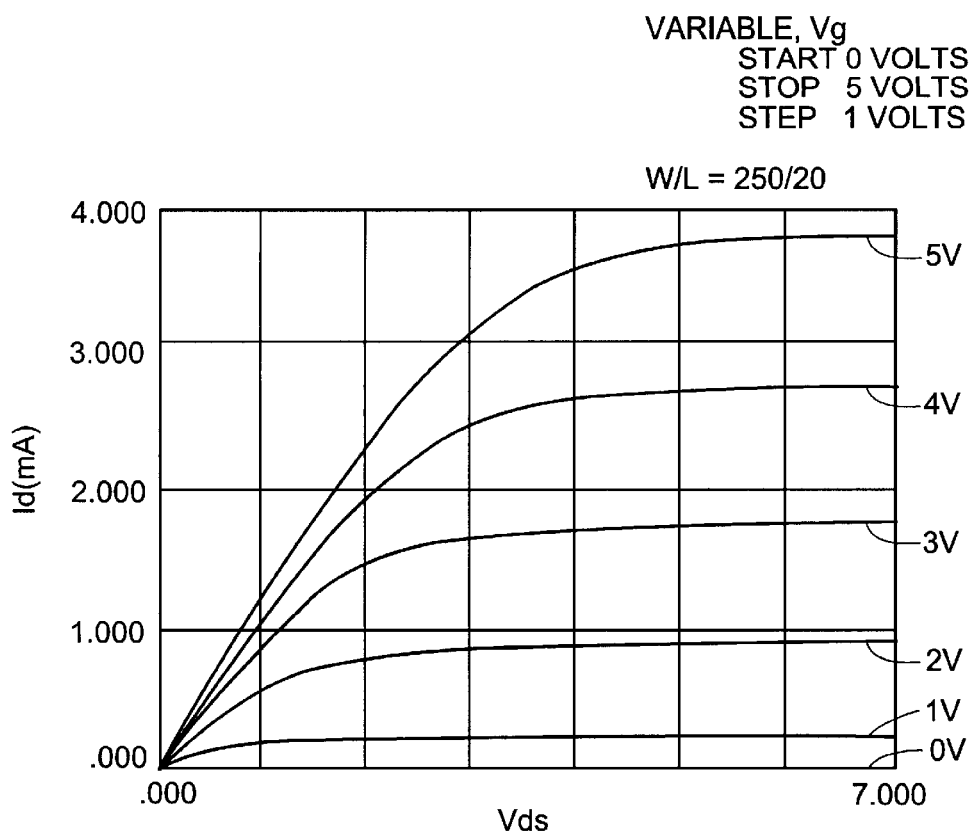
FIG. 8A illustrates the drain current output of the device of FIG. 8A with the gate voltage varying between 0 and 5 volts.

FIG. 8A graphically illustrates the drain current ID as a function of drain-source voltage of the device of FIG. 6A at gate voltages of $V_{GS}$=0, 1, 2, 3, 4 and 5 volts.

Figure 8B:
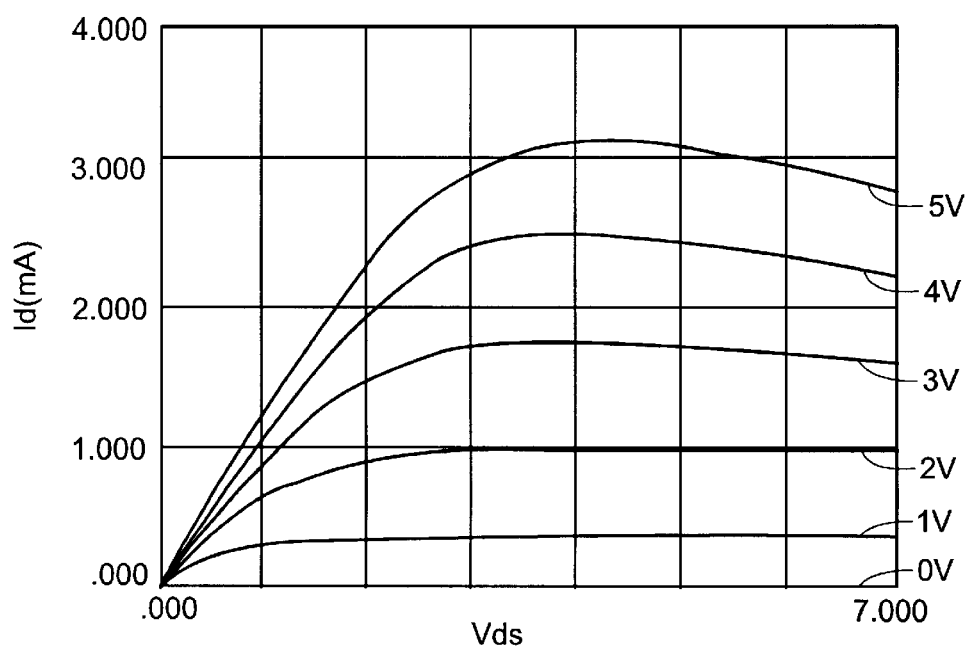
FIG. 8B illustrates the drain current output of the device of FIG. 6B with the gate voltage varying between 0 and 5 volts.

FIG. 8B graphically illustrates the drain current $I_D$ as a function of drain-source voltage of the device of FIG. 6B at gate voltages of $V_{GS}$=0, 1, 2, 3, 4 and 5 volts.

Figure 9:
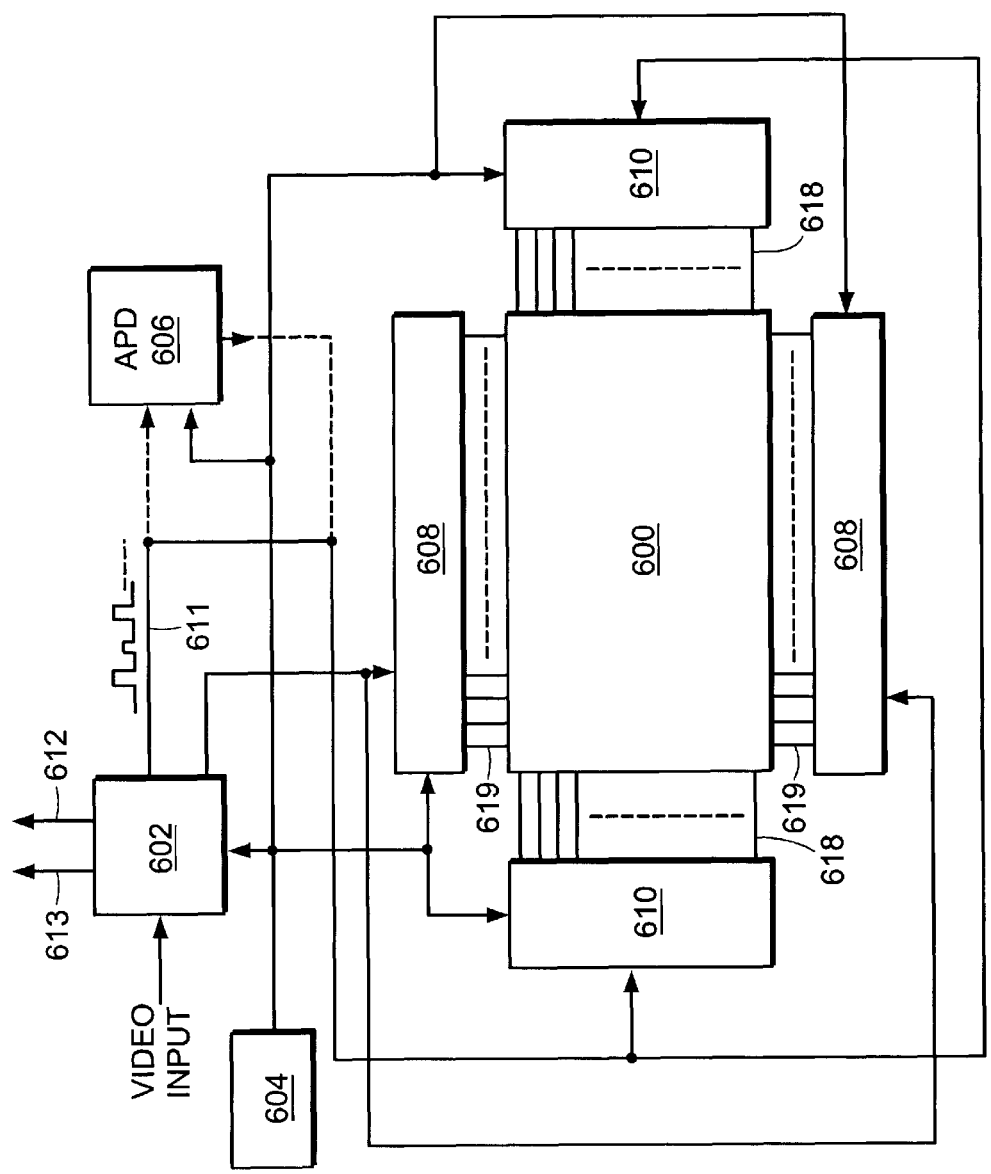
FIG. 9 is a circuit diagram illustrating the driver system for a projection device of the present invention.

Referring to FIG. 9, an active matrix 600 comprises a plurality of light valves which are individually actuated by collocated driver circuitry (see FIG. 1B). The collocated driver circuitry is controlled by supporting driver circuitry which includes a video conditioning circuit 602, a system clock 604, an optional amplitude to pulse duration (APD) converter 606, column drivers 608, and a row drivers 610.

The video conditioning circuit 602 receives a video input signal which may be an RGB signal, an NTSC signal or other video format signal, or any digital or analog signal. The conditioning circuit processes the incoming signal producing separate video output signals (on lines, 611, 612 and 613) for each primary color and a synchronization signal (on line 615) for the column and row drivers 608 and 610. The video output signal on line 611 is a serial data stream wherein the amplitude of each signal of the data stream determines the intensity of light transmitted through each light valve.

If the APD convertor is not employed, the serial data stream on line 615 is received by the row drivers 610. The row drivers 610 send each of the signal data streams to the light valves through buses 618. The column drivers receive the sync signal on line 615 and, responsive to the sync signal, will be sent through buses 619 to turn on individual transistors allowing the associated signal of the data stream to charge the capacitor in each pixel. The capacitor sustains a charge, which is proportioned to the amplitude of the associated signal, on the light valve until the next scan of the array.

Alternately, the ADP converter may be employed such that each signal of the video output data stream is converted to a pulse having a pulse width which is proportional to the signal's amplitude. In any case, the driver circuit operates in the same manner as previously described.

Projection display devices of the active matrix display system can employ light valve matrices having pixel densities which satisfy any of a wide range of the following existing computer display format requirements:

Thus, a display monitor employing one or more single crystal silicon light valve matrices having any of the above-described pixel densities may be provided in accordance with the active display system described herein.

| Application | Display Format (Column x Row) |
|---|---|
| 1) Common Personal Computer | 1024 x 768 |
|  | 1280 x 1024 |
| 2) Workstation (Advanced Personal Computer) | 1280 x 1024 |
|  | 1580 x 1280 |
|  | 2048 x 2048 |
| 3) Other Workstations (Non-Standard) | 1152 x 900 |
|  | 1280 x 1024 |
|  | 1600 x 1280 |

One feature of the active matrix display panel is that projection devices employing single crystal light valve matrices provide high resolution images. High resolution images are possible because high density light valve arrays may be formed in single crystal silicon films. Referring to Table 1, the light valve diagonal is shown for various array sizes and pixel densities. Note that the diagonal dimensions followed by an asterisk indicate the array is compatible with 35 mm optics. The use of 35 mm optics is a key feature in minimizing the size, weight and cost of the described optics requiring the light valve image designed dimension to be no greater than 42 mm (1.654 inches). Therefore, it is desirable to use a light valve imaging technology that provides the highest density of information content. It is likely that the light valve technology discussed herein is compatible with as-fabricated densities of 2000 dots-per-inch. This allows projection of high resolution images using compact, low cost and widely available optical components. The small size of the light valve allows the use of small format condenser lens assembly dichroic mirrors and prisms and projection lens. Subsequently, the package size of the described projector and monitor can be maintained at small dimensions and component weight is similarly minimized. Appropriate 35 mm format optical components are widely available and can be obtained at low cost relative to large and/or custom optical components. For projector and monitor requirements that cannot be met with a 35 mm compatible light valve, larger conventional or custom optical components may be employed, Due to the minimum size of a particular light valve format afforded by the described light valve technology, similar cost, size and weight advantages are translated to the procurement of custom optical components.

As has been described, the light valve technology described herein can be used to implement projection arrays of 1024×768 through 2048×2048 pixels using 35 mm format optical components. This will permit the execution of high resolution color and monochrome image projectors and monitors at relatively compact dimensions and low weight.

One implementation of the monitor is to form a 17.5 inch×11.5 inch image suitable for the display of two side-by-side 8.5 inch×11 inch pages with additional screen room for data window access. The use of the described light valve and projection technology would allow the physical format of the monitor to be less than 22 inches high, less than 20 inches wide, and less than 10 inches deep. The use of a single 150 to 300 watt metal-halogen lamp in this implementation would provide the rear-proportion screen image at a brightness of 25 foot-Lamberts or greater. The choice of screen material could include a simple diffuser for maximum viewing angle or a lenticular configuration for maximum brightness over a reduced solid viewing angle.

TABLE 1

DIAGONAL ARRAY DIMENSION - INCHES/(MM)
Fabricated dots/inch (DPI) on light valve matrix

| ARRAY SIZE | 800 | 1000 | 1200 | 2000 |
|---|---|---|---|---|
| 1024 × 768 | 1.600* | 1.280* | 1.137* | 0.640* |
|  | (40.64) | (32.51) | (28.88) | (16.26) |
| 1280 × 1024 | 2.049 | 1.639* | 1.366* | 0.820* |
|  | (52.04) | (41.63) | (34.70) | (20.82) |
| 1580 × 1280 | 2.542 | 2.033 | 1.695 | 1.017* |
|  | (64.56) | (51.65) | (43.05) | (25.82) |
| 2048 × 2048 | 3.620 | 2.896 | 2.414 | 1.448* |
|  | (91.96) | (73.57) | (61.32) | (36.78) |

Another feature of the active matrix display is that a projection display device employing single crystal silicon light valve matrices provides images with high brightness. To accomplish this, each single crystal silicon light valve matrix employed in a projection display device has a high optical aperture which is defined as the percentage of transparent area to total matrix area. Table 2 provides the optical aperture for various light valve arrays. It is noted that in general the minimum acceptable optical aperture for an array is 40%. As indicated by Table 2, as pixel density increases, which increases image resolution, optical aperture decreases. However, reducing the switching device size and/or the interconnect size for a given pixel density will increase the optical aperture.

TABLE 2

OPTICAL APERTURE COMPUTATIONS

| | | | | |
|---|---|---|---|---|
| Transistor length (um) | 3 | 3 | 3 | 3 |
| Transistor width (um) | 6 | 6 | 6 | 6 |
| Line width (um) | 2 | 4 | 6 | 8 |
| lines per inch | 1000 | 1000 | 1000 | 1000 |
| pixel size (um) | 25.4 | 25.4 | 25.4 | 25.4 |
| grid shadow (sq. um) | 97.6 | 187.2 | 268.8 | 342.4 |
| trans. shadow (sq. um) | 18 | 18 | 18 | 18 |
| pixel area (sq. um) | 645 | 645 | 645 | 645 |
| Packing Factor (%) | 85 | 85 | 85 | 85 |
| OPTICAL APERTURE (%) | 69.8 | 58.0 | 47.2 | 37.5 |
| Transistor length (um) | 3 | 3 | 3 | 3 |
| Transistor width (um) | 6 | 6 | 6 | 6 |
| Line width (um) | 2 | 4 | 6 | 8 |
| lines per inch | 800 | 800 | 800 | 800 |
| pixel size (um) | 31.8 | 31.8 | 31.8 | 31.8 |
| grid shadow (sq. um) | 123 | 238 | 345 | 444 |
| trans. shadow (sq. um) | 18 | 18 | 18 | 18 |
| pixel area (sq. um) | 1008 | 1008 | 1008 | 1008 |
| Packing Factor (%) | 85 | 85 | 85 | 85 |
| OPTICAL APERTURE (%) | 73.1 | 73.1 | 73.1 | 73.1 |
| Transistor length (um) | 3 | 3 | 3 | 3 |
| Transistor width (um) | 6 | 6 | 6 | 6 |
| Line width (um) | 2 | 4 | 6 | 8 |
| lines per inch | 1200 | 1200 | 1200 | 1200 |
| pixel size (um) | 21.2 | 21.2 | 21.2 | 21.2 |
| grid shadow (sq. um) | 80.7 | 153.3 | 218.0 | 247.7 |
| trans. shadow (sq. um) | 18 | 18 | 18 | 18 |
| pixel area (sq. um) | 448 | 448 | 448 | 448 |
| Packing Factor (%) | 85 | 85 | 85 | 85 |
| OPTICAL APERTURE (%) | 66.3 | 52.5 | 40.2 | 29.5 |
| Transistor length (um) | 3 | 3 | 3 | 3 |
| Transistor width (um) | 6 | 6 | 6 | 6 |
| Line width (um) | 2 | 4 | 6 | 8 |
| lines per inch | 2000 | 2000 | 2000 | 2000 |
| pixel size (um) | 12.7 | 12.7 | 12.7 | 12.7 |
| grid shadow (sq. um) | 46.8 | 85.6 | 116.4 | 139.2 |
| trans. shadow (sq. um) | 18 | 18 | 18 | 18 |
| pixel area (sq. um) | 161.3 | 161.3 | 161.3 | 161.3 |
| Packing Factor (%) | 85 | 85 | 85 | 85 |
| OPTICAL APERTURE (%) | 50.9 | 30.4 | 14.2 | 2.2 |

Figure 10A:
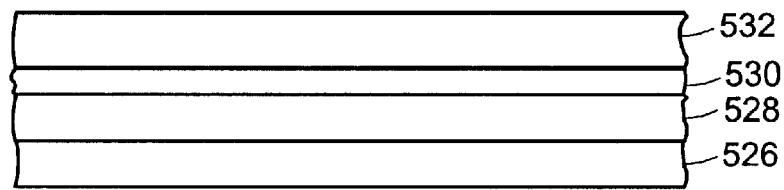
FIGS. 10A–10D are a preferred process and transfer sequence for fabricating a light valve matrix and transferring it to a support structure.

In another preferred embodiment, a growth and transfer process is employed within the display system to provide a thin-film of single crystal silicon positioned on glass as shown in FIGS. 10A–10D. Referring to FIG. 10A, a buffer (insulator) layer 528 of silicon is epitaxially grown on a silicon substrate 526. A strained GeSi layer 530 is epitaxially grown on the buffer layer 528 and an upper layer 532 of single crystal silicon is epitaxially grown on the GeSi layer. The strained layer 530 should be thin, on the order of a few hundred angstroms, to avoid misfit defect formation that would thread into the upper silicon layer 532.

Figure 10B:
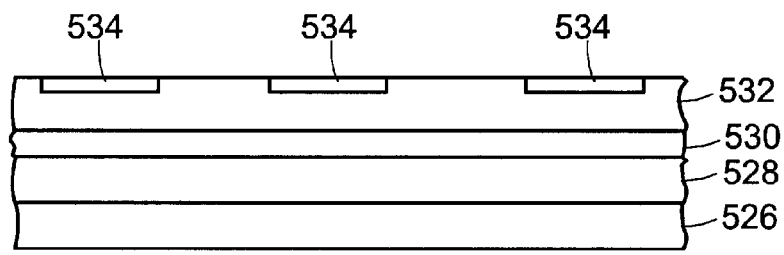
Figure 10C:
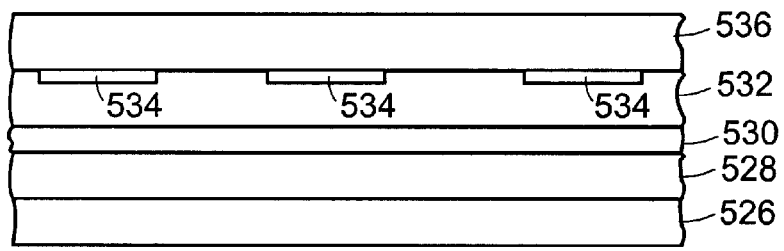
Figure 10D:
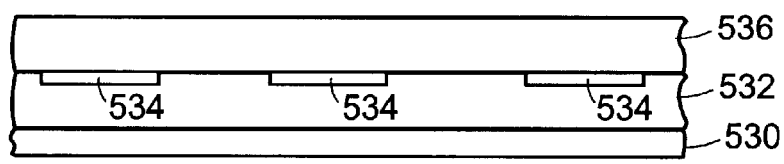

Referring to FIG. 10B, integrated circuit processing techniques, such as any of the techniques previously described herein, are employed to form light valve matrix circuitry 534 in the single crystal silicon layer 532. Next, the processed wafer is mounted with an epoxy adhesive of the type described below to a glass or plastic support 536 (FIG. 10C). The epoxy fills in the voids formed by the processing and adheres the front face to the support 536. The silicon substrate 526 and buffer layer 528 are etched off with the GeSi layer 530 serving as an etch stop layer (FIG. 10D). The GeSi layer could then be selectively etched away without effecting the silicon film 532.

Figure 25A:
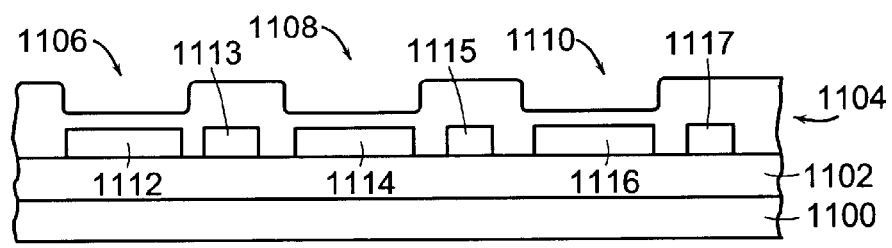
FIGS. 25A–25J is a preferred process flow sequence illustrating in cross-sectional views a photographic development process for fabricating an array of color filter elements.

FIGS. 11A–11C illustrate another preferred process for transferring and adhering circuits of thin films of silicon to a glass substrate. The starting structure is a silicon wafer 718 upon which an oxide layer 716 and a thin film of poly-Si, a-Si or x-Si 714 is formed using any of the previously described processes such as ISE or CLEFT. A plurality of circuits, such as pixel electrodes, TFT's, Si drivers and Si logic circuits, are then formed in the thin film. FIG. 25A shows three such wafers, A, B, C. In wafer A, logic circuits 740 are formed. In wafer B, pixel electrodes 762 and TFT's 751 are formed. In wafer C, driver circuits 720 are formed. A wafer is attached to a superstrate transfer body 712, such as glass or other transparent insulator, using an adhesive 721. Preferably the adhesive is comprised of an epoxy, such as, a cycloaliphatic anhydride; for example; for example, EP-112 LS made by Masterbond Inc. The adhesive must satisfy the following criteria:

Excellent spectral transmission in the visible range;

Good adhesion to glass, oxides, metals, nitrides;

No reactions with glass, metals, oxides, nitrides;

Low shrinkage;

Low warp/stress;

Able to tolerate acids or bases at 100° C. for extended periods without lifting, losing adhesion, or degrading;

Able to withstand 180° C. for 2 hours with no optical change;

Good resistance to acids and solvents;

Able to tolerate dicing and heating step (including an acid etch step with no lifting);

Low viscosity to allow thin adhesive films; and

Ability to be vacuum degassed to eliminate all bubbles.

In general, the cycloaliphatic anhydrides meet most of the above criteria. The epoxy preferably has a low cure temperature to minimize shrinkage, a very low ion content (<5 ppm) and spectral stability over extended time periods.

The wafer is attached, using the adhesive 721, to a glass superstrate 712. The adhesive is vacuum degassed to eliminate all bubbles. The sandwich structure is then cured at a low temperature of about 100° C. for 4–8 hours which causes the adhesive to gel and minimizes the shrinkage characteristics. Then the adhesive is fully cured at a higher temperature of about 160° C. for about 8 hours. This cure assures that the bonds are fully matured. Without this cure, the adhesive will not stand up to the subsequent acid etching step.

The wafer, is then cleaned and the native oxide 718 is etched off the back surface. The wafer is put into a solution (KOH or equivalent) of 25 grams to 75 ml H20 at 100° C. Depending on the thickness of the wafer, it may take up to 5 hours to etch the Si 718 and oxide 716 layers. The solution etches silicon very rapidly, i.e. 2 to 3 microns/min., and uniformly if the wafers are held horizontally in the solution with the etching surface face up. The etchant has a very low etch rate on oxide, so that as the substrate is etched away and the buried oxide is exposed, the etching rate goes down. The selectivity of the silicon etch rate in KOH versus the oxide etch rate in KOH is very high (200:1). This selectivity, combined with the uniformity of the silicon etching, allows the observer to monitor the process and to stop the etch in the buried oxide layer 716 without punching through to the thin silicon layer 714 above it. Wafers up to 25 mils thick and oxides as thin as 4000A have been successfully etched using this process. An alternative etchant is hydrazine, which has a much higher etch rate selectivity or ethylene diamine pyrocatacol (EDP).

When the silicon is completely gone, the vigorous bubbling, which is characteristic of silicon etching in KOH, abruptly stops, signalling that the etching is complete.

The thin films 714 transferred to the respective glass superstrates 712 are now rinsed and dried. If not already provided with circuits 740, 751, 762, or 720, the films 714 can be backside circuit processed if desired, since the epoxy adhesive 720 has very good resistance to chemicals. In addition, the epoxy is very low in stress, so that the thin film is very flat and can go through conventional photolithography steps.

In the aforementioned light valve matrix fabrication processes, disclination defects in the liquid crystal material may be induced by non-planar circuit topography formed in the film resulting in irregular stacking and subsequent image aberration. Planarized circuitry would eliminate the disclination problem. An option is to use the oxide layer after transfer of the film to the optically transmissive substrate to provide a planar surface. The oxide layer is planar or substantially planar (i.e. uniformities of <1 micron across its surface) such that an even topography is provided. Then any necessary shielding or pixel circuitry can be formed to produce a planarized circuit substantially free of disclination.

It is noted that light valve matrices having a diagonal of 1–2 inches do not require spacers in the liquid crystal volume (see FIG. 1A). Since spacers are non-transmissive elements, eliminating them from the volume results in an improved optical aperture and thus increased brightness for the matrix. Also prevents optical aberration caused by spacers at small pixel geometries.

Due to the higher intensities of light used in projection systems that are necessary to provide the desired brightness, the sensitivity of the single crystal pixel transistors to the light source can impair performance. The light source can be a halogen lamp that produces between 100 and 1000 watts and preferably operates in the range of 150–300 watts. Other lights such as discrete lasers (RGB), cathodoluminescent light sources, and arc-lamps producing similar levels of power per unit area can also be used. It is therefore desirable to reduce the sensitivity of the active matrix to the light source. This is accomplished by shielding one or both sides of each transistor in the array with a light shield that will substantially attenuate the light directed or scattered toward each transistor. A metal or other optically opaque material can be used as a shield. When the shield is a metal it can also serve as an interconnect or a gate to the transistor being shielded. At normal incidence, a metal shield can completely attenuate light from the source at wavelengths at or above the silicon bandgap with thicknesses in the range of 2000–10,000 angstroms. Shielding can also be employed around the edge of the active matrix to attenuate or block light directed towards the peripheral circuitry.

In FIGS. 12A–12E a process for fabricating a double shielded active matrix array for a projection system is illustrated. The left figure shows a cross-sectional view of a pixel transistor of each step or embodiment. The right side illustration in FIGS. 12A–12C and 12E show a top view including the transistor 804, pixel area 811, and interconnect lines 808 and 810. In FIG. 12A there is shown the silicon substrate 800, oxide layer 802, source and drain 804 regions, a channel region 805, a second oxide layer 806, and portions of the interconnect lines 808 and 810 that serve as the gate and source connector for the transistor 804. FIG. 12B shows a third oxide layer 812 and holes 814 formed therein to provide a bridge interconnect between portions of line 808. In FIG. 12C is shown the formation of the first metal shield 816 over the oxide 812 and through holes 814 to interconnect lines 808. The first shield 816 has a surface area to substantially block normally incident light from reaching transistor 804 from one side of the circuit panel. The area of shield 816 should be minimized to maintain the optical aperture of the array. FIG. 12D illustrates the use of a body contact 822 fabricated after the transfer of the panel onto glass substrate 818 and formation of the second shield 820. The fabrication of such a body contact is described more fully in U.S. Ser. No. 07/823,858 filed on Jan. 22, 1992, which is incorporated herein by reference. In FIG. 12E there is illustrated the use of a portion of the second shield 824 as a second back side gate 826. Gate 826 can be used to control the opposite side of the channel from the front side gate region 808. The present transfer process thus provides for additional back side processing to provide optical interconnects, optical shielding interconnects, and double sided gating of each or selected transistors in the array.

Color can be implemented in the projector or monitor through the use of color filters instead of dichroic mirrors. In one implementation, white light from a single or multiple lamps could be passed through each of red, green and blue filter to its incidence onto the appropriate color-assigned light valve. Alternatively, color filters can be fabricated directly on the light valve assembly. This could be done with a single color filter (e.g.,red, green or blue) on a light valve or the specific alignment of color filters on the discrete elements constituting the light valve. The latter would allow a color image to be obtained using a single light valve but forces a factor of 3 or 4 reduction in color pixel density as the elements are assigned a red, green, or blue filter or a red, green blue and white filter respectively. Alternatively, subtractive color filters (yellow, cyan and magenta) would be similarly used.

A key criterion in the projector/monitor design is the management of heat generated by the lamp light source. A significant portion of this heat is in the form of infrared (IR) radiation emanating from the lamp. Methods of controlling this IR radiation are its absorption by an IR filter or its reflection by an IR "heat mirror" that allows high transmission of visible light to the subsequent optics. Another method is the use of a dichroic mirror that separates the IR radiation from the visible light path and directs the IR to directly exit the projector or monitor housing.

A light valve panel formed by the described technology is compatible with 35 mm format optics. Therefore, this imaging device can be fabricated such that the assembled device has equivalent physical dimensions as a standard 35 mm photographic transparency whose image is projected via a conventional and generally available 35 mm "slide projector". Thus, an embodiment of the light valve projector is to use a single light valve matrix panel with integral drive electronics, as described herein, that is packaged to be size equivalent with a standard mounted 35 mm transparency and insert this modular electronic imaging device into a 35 mm "slide projector" without modification in order to generate the projected image. The light valve imaging device is connected by a cable to control electronics as are described herein. In this embodiment, a single light valve panel could generate a monochrome image or a color image through the use of applied color filters as described elsewhere herein. The light valve panel used for this embodiment can have the same fabricated element/pixel density as described for the other embodiments.

Figure 13:
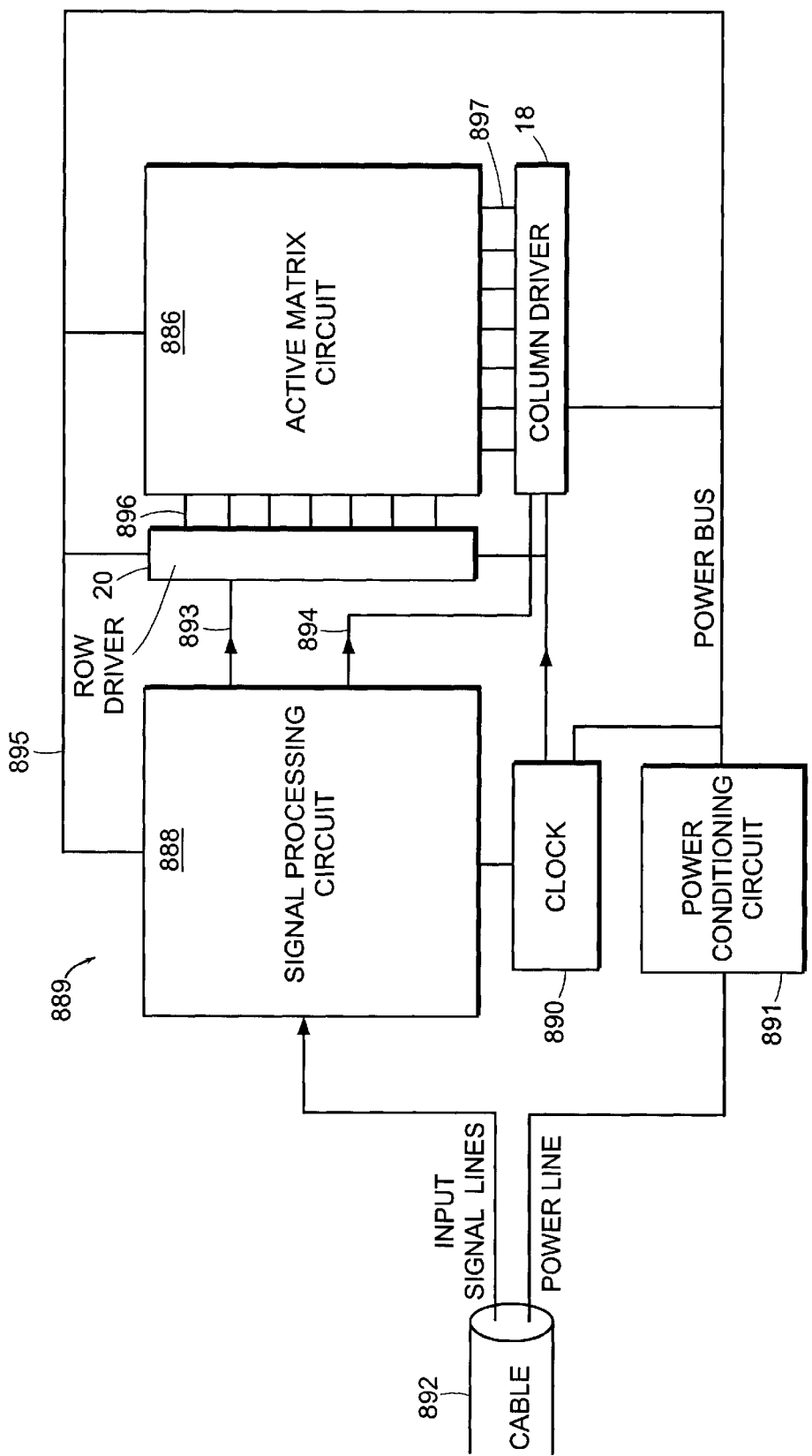
FIG. 13 is a circuit diagram illustrating a preferred driver system for an active matrix slide assembly.

Referring to FIG. 13, the active matrix comprises a plurality of light valves which are individually actuated by collocated driver circuitry 886 (see also FIG. 1B). The collocated driver circuitry is controlled by supporting driver circuitry which includes a signal processing circuit 888, a system clock 890, a power conditioning circuit 891, column drivers 18, and row drivers 20.

The signal processing circuit 888 receives via the cable 892 an input signal which may be an RGB signal, an NTSC signal or other video format signal, or any digital or analog signal. The signal processing circuit processes the incoming signal and (for a multi-color active matrix) produces separate video output signals for each primary color and synchronization signals for the column and row drivers. These signals are provided to the column driver (via bus 893) and row driver (via bus 894). The video output signal on line 895 is a serial data stream wherein the amplitude of each signal of the data stream determines the intensity of light transmitted through each light valve. Alternatively, the video output signal may be a digitally formatted data stream indicative of the light intensity. Preferably, the video output signal is VGA compatible, providing a data rate of up to 32 Mbps.

The serial data stream on line 895 is received by the row drivers 18. The row drivers send each of the signal data streams to the light valves through buses 896. The column drivers 20, responsive to the sync signal, send a signal through buses 897 to turn on individual transistors allowing the associated signal of the data stream to charge the capacitor in each pixel. The capacitor sustains a charge, which is proportioned to the amplitude of the associated signal on the light valve until the next scan of the array.

Figure 14:
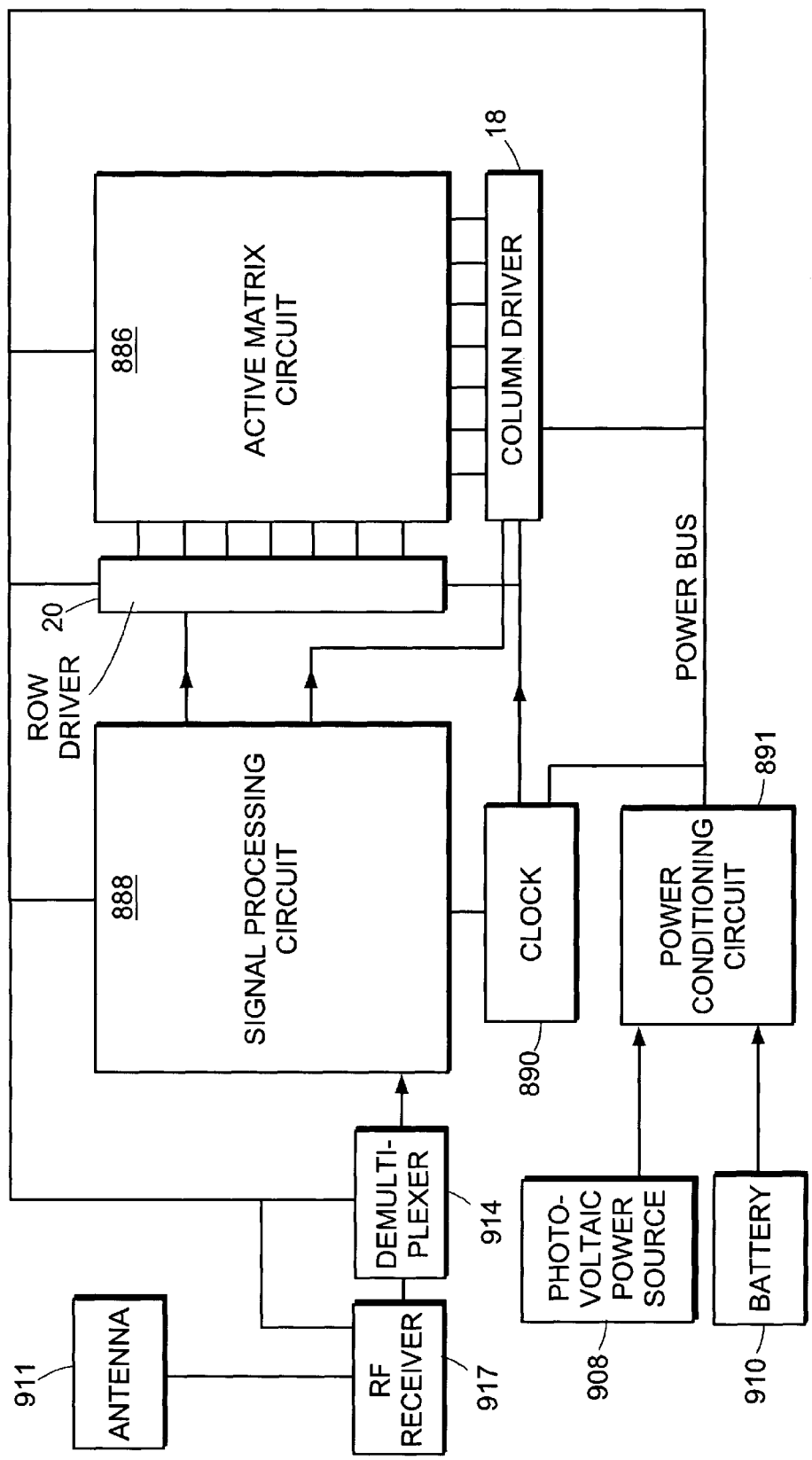
FIGS. 14 and 15 are circuit diagrams illustrating two preferred driver systems for an active matrix display.

In FIG. 14, an active matrix slide assembly 900 includes an AM slide 902 and a remote electronics housing 904. The slide 902 is dimensioned to be positioned in the chamber 838 of a 35 mm slide projector 830. In contrast to previously described embodiments, the slide 902 is not physically connected to the electronics housing 904. Instead, the slide and the electronics in the housing communicate with each other via antennas elements 905 and 906 respectively. In preferred embodiments, the antennas can be a pair of RF antennas or an infrared transmitter element such as an infrared LED paired with an infrared receiver element which can be a photodiode elements. The antenna 905 can be integrated into a handle (not shown) to provide for manual insertion and removal from chamber 838.

Figure 15:
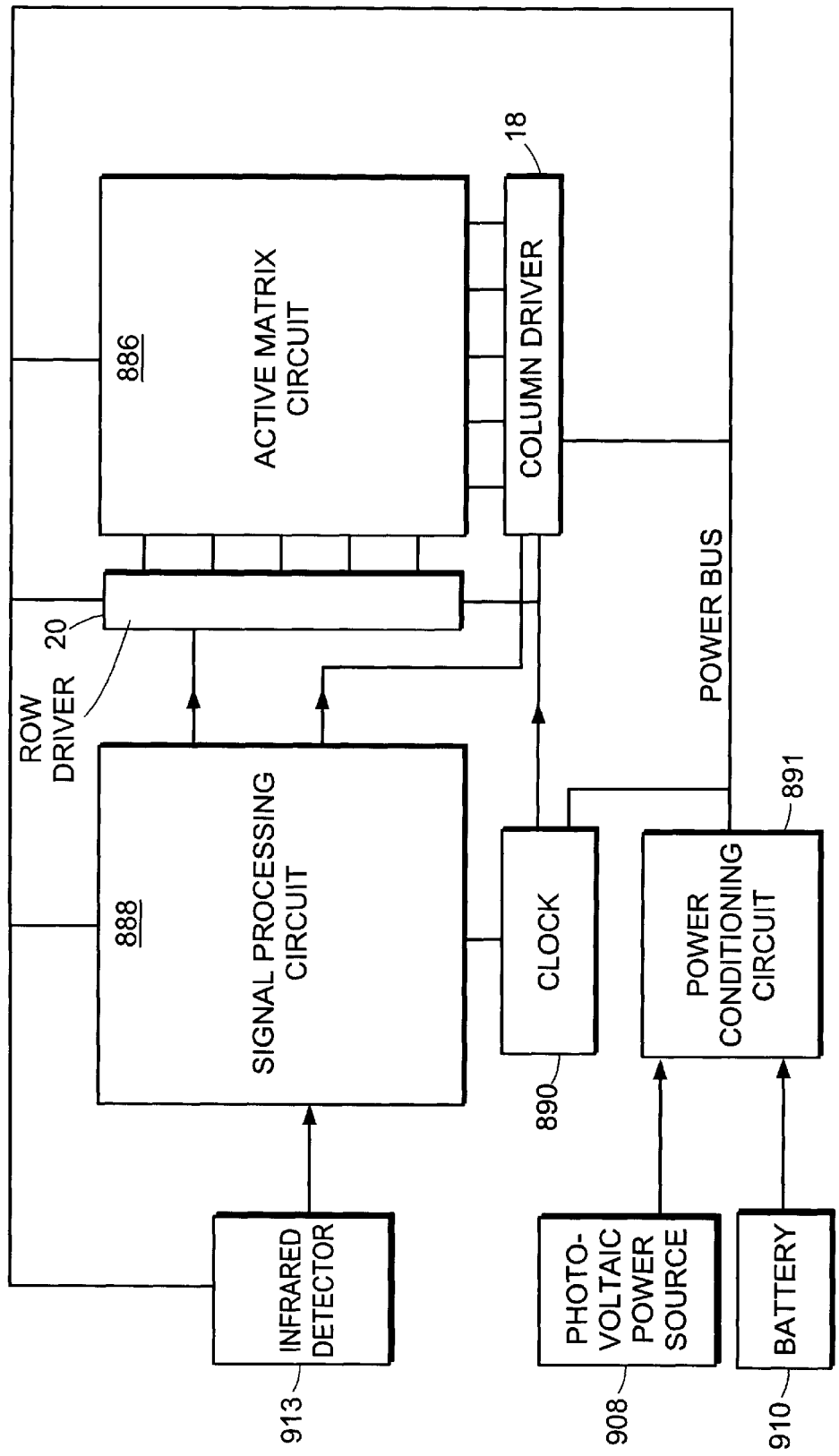

Driver circuitry for the active matrix slide assembly of FIG. 14 is illustrated in FIGS. 15A–15B. Referring to FIG. 15A, the driver circuitry includes the signal processing circuit 888, the system clock 890, the power conditioning circuit 891, column drivers 18, row drivers 20, a photovoltaic power source 908, a battery 910, an RF receiver 912 and an demultiplexer 914. The RF receiver 912 receives a stream of RF signals from the antenna 911. A demultiplexer 914 formats the RF signal stream such that it is can be processed by the previously-described signal processing circuit 888. The battery 910 and the photovoltaic power source 908, either individually or together, provide power to support the operations of the active matrix slide circuitry. The photovoltaic power source 908 can use slide projector light source energy to provide power to the active matrix slide and is therefore mounted onto the slide outer surface facing the light source (shown in FIG. 14).

Referring to FIG. 15B, the driver circuitry includes the signal processing circuit 888, the system clock 890, the power conditioning circuit 891, column drivers 18, row drivers 20, a photovoltaic power source 908, a battery 910 and an infrared detector photodiode 913. The photodiode 913 receives infrared signals from the electronics (not shown) which are processed by the signal processing circuit 888.

Figure 16:
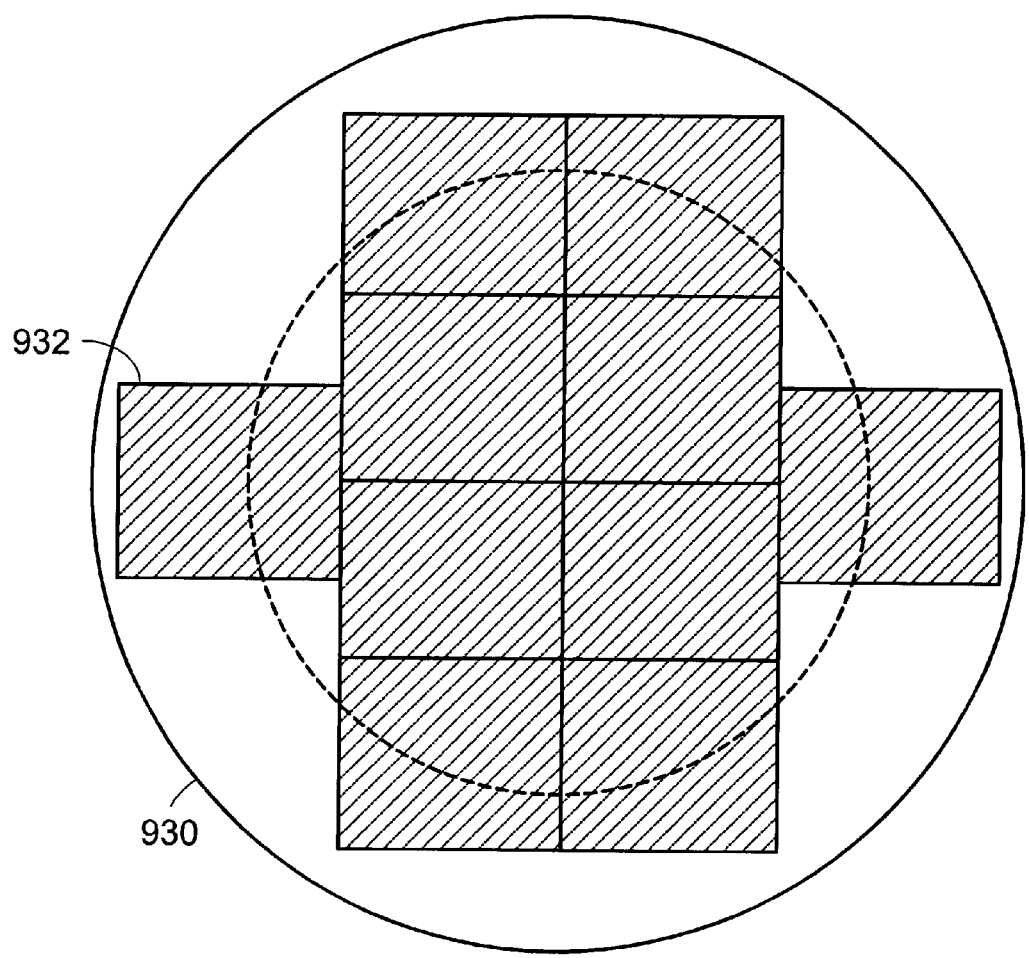
FIG. 16 is a top view of a semiconductor wafer which can be processed to provide a plurality of active matrices for use in active matrix slide assemblies.

As noted previously, an active matrix slide can be fabricated which has equivalent dimensions as a standard 35 mm slide. This can be accomplished because the previously described fabrication processes can produce a plurality of small active matrix circuit panels from a single wafer as shown in FIG. 16. Using a 6 inch silicon wafer 930, a number of active matrices can be produced from the wafer using any of the aforementioned processing techniques.

Figure 17:
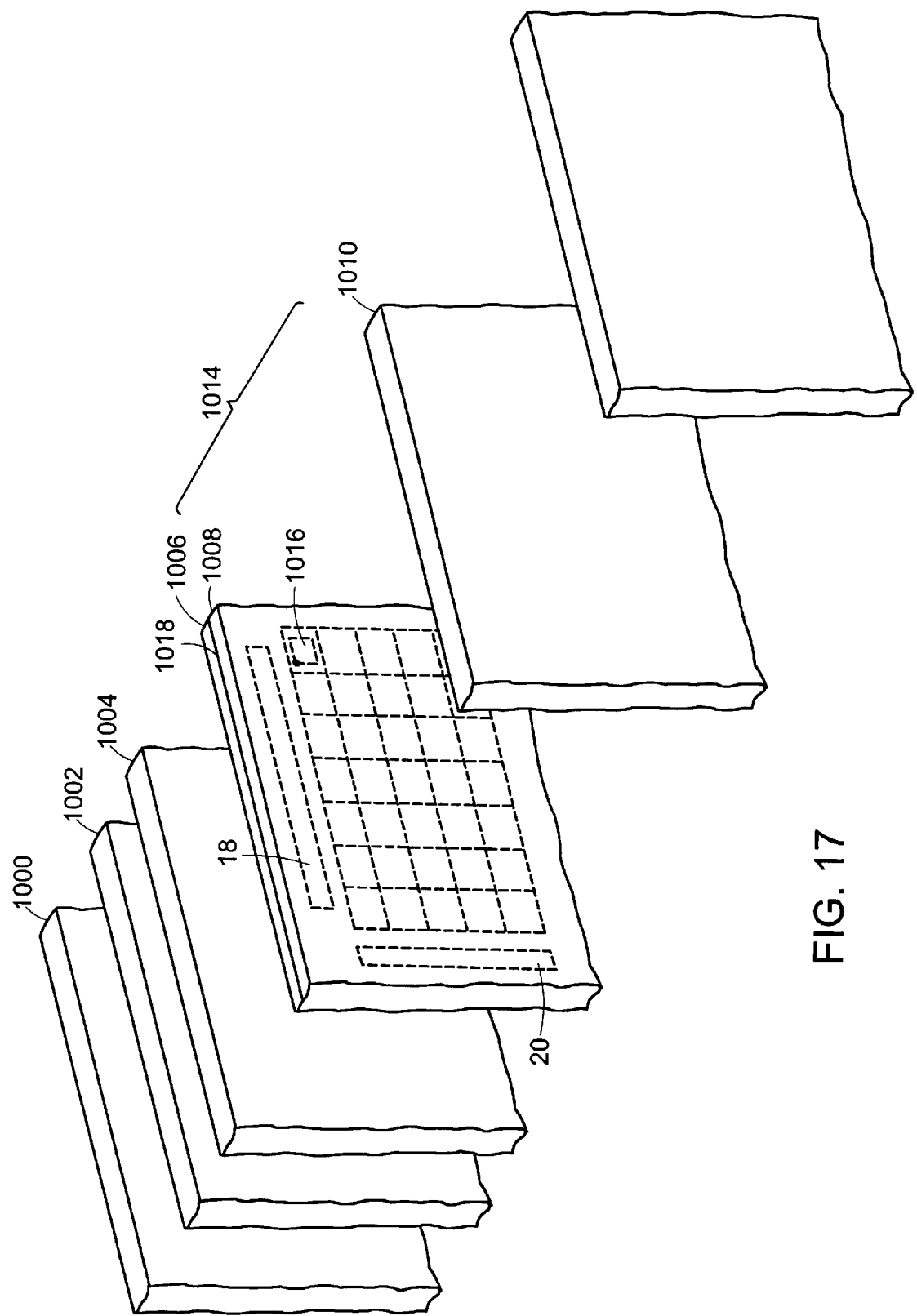
FIG. 17 is an exploded perspective view of an active matrix transmission display employing a color filter system of the present invention.

Another form of active matrix display system is illustrated in the perspective view of a liquid crystal transmission display in FIG. 17. The basic components of the display include a light source 1000 that can be white or some other appropriate color, a first polarizing filter 1002, an optically transparent substrate 1004, a color filter array 1006, an active matrix circuit panel 1008, a counterelectrode 1010 and a second polarizing filter 1012, which are secured in a layered structure. A liquid crystal material 1014 is placed in a volume between the active matrix circuit panel 1008 and the counterelectrode 1010.

The circuit panel 1008 comprises an array of pixel elements 1016 formed in a surface 1018 of a thin film of essentially single crystal silicon. The pixel elements 1016 are individually actuated by a drive circuit having first 18 and second 20 circuit components that are positioned adjacent the pixel array such that each pixel can produce an electric field in the liquid crystal material lying between the pixel 1016 and the counterelectrode 1010 secured to the polarizer 1012. The electric field causes a rotation of the polarization of light being transmitted across the liquid crystal material that results in an adjacent color filter element being illuminated. The color filter array 1006 is located adjacent to the circuit panel 1008 such that each color filter element is associated with a pixel element. The individual elements of color filter array 1006 can be grouped into an arrangement of three (or four) colors that can have any one of a number of geometric configurations such as a triad arrangement, a stripe arrangement or a quad arrangement. The three colors can be, for example, blue, green and red, or alternatively yellow, cyan and magenta, or any other group of colors that will provide the desired colors to be produced by the display. The four colors can be, for example, blue, green, red and white or yellow, cyan, magenta and white/black or any other group of four colors. The pixel elements 1016 or light valves associated with each filter element can be selectively actuated to provide any desired color for that pixel group.

A drive circuit that can be used to control the display is illustrated in FIG. 1B and was discussed previously or as described in U.S. Ser. No. 07/815,684, filed on Dec. 31, 1991.

The active matrix circuit panel is formed in or on a layer of essentially single crystal semiconductor material such as silicon. It is noted that any number of fabrication techniques, including those previously described herein, can be employed to provide thin films or layers of single crystal silicon.

Figure 18A:
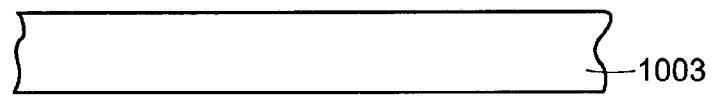
FIGS. 18A–18C is a preferred process flow sequence illustrating the SIMOX process for fabricating a single crystal silicon layer.
Figure 18B:
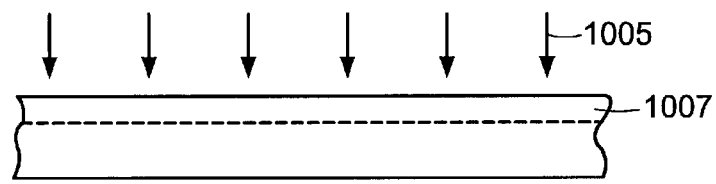
Figure 18C:
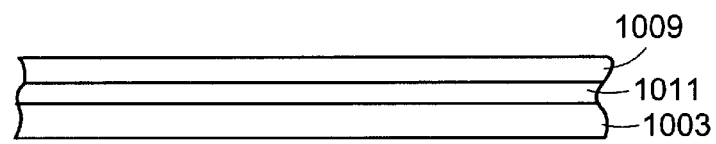

The present invention includes other fabrication techniques which can be employed to provide thin layers of single crystal silicon. In one embodiment, the SIMOX fabrication process shown in FIGS. 18A–18C can be used. A single crystal silicon substrate 1003 shown in FIG. 18A receives an implant of $5*10^{17}/cm^2$ to $2*10^{18}/cm^2$ of oxygen atoms 1007 (FIG. 18B). The implant process can be performed at temperatures exceeding 650° C. Next, the wafer is subjected to a high temperature annealing process 1005 (at about 1300° C.) for about six hours. Referring to FIG. 18C, the resulting structure has a buried oxide layer 1011 (thickness of about 4000 angstroms) below a single crystal layer 1009 (thickness of about 2000 angstroms). It is noted that a multiple implant and anneal procedure can be employed to further improve the crystallinity of the silicon layer.

Figure 19:
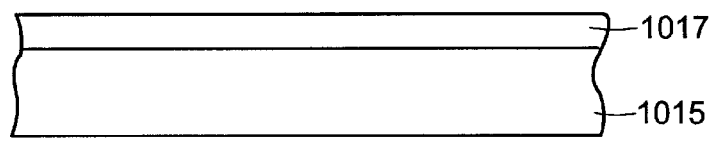
FIG. 19 illustrates the Van der Waals bonding approach for providing a single crystal silicon layer.

In another embodiment, a thin film or layer of single crystal silicon can be secured on a quartz substrate by Van der Waals bonding. Referring to FIG. 19, a silicon thin film 1017 is located on a quartz substrate 1015. The film 1017 is secured to the substrate 1015 by an electrostatic force known as a Van der Waals force, which is an attractive force between two different atoms or nonpolar molecules. The Van der Waals force arises because a fluctuating dipole moment in one molecule-type (either silicon or quartz) induces a dipole moment in the other molecule-type, and the two dipole moments interact.

Figure 20A:
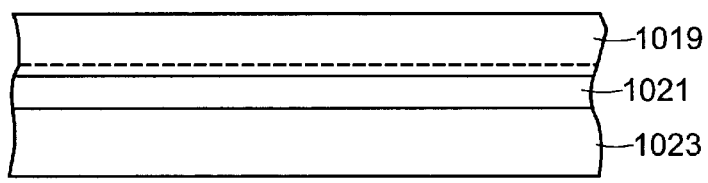
FIGS. 20A–20B is a preferred process flow sequence illustrating the bonded wafer process for forming a single crystal silicon layer.
Figure 20B:
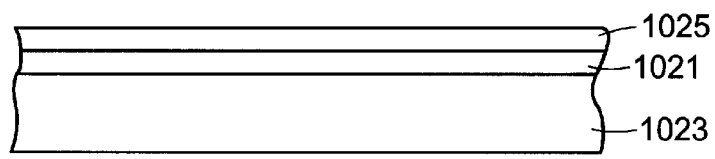

In another embodiment, a bonded wafer approach can be employed to provide a layer of single crystal silicon. Referring to FIG. 20A, an oxide layer 1021 is formed on a single crystal silicon wafer 1023 by known techniques. A second single crystal silicon wafer 1019 is positioned on the oxide layer 1021. The wafer 1019 is then processed to obtain a thin layer of single crystal silicon (dashed lines). Any known processing techniques, such as lapping or etching, can be used to obtain the thin layer of single crystal silicon 1025 (FIG. 20B). Active matrix circuitry can be formed in the single crystal silicon layer 1025.

Figure 21A:
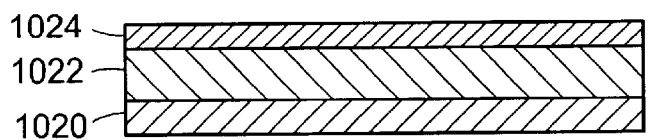
FIGS. 21A–21G is a preferred process flow sequence illustrating the fabrication of a transmissive active matrix color display.

FIGS. 21A–21G illustrate a preferred fabrication process for forming an active matrix color display. Referring to FIG. 21A, an SOI structure includes a substrate 1020 and an oxide 1022 (such as, for example, $SiO_2$) that is grown or deposited on the substrate 1020. A thin single crystal layer 1024 of silicon is formed over the oxide 1020. The oxide (or insulator) is thus buried beneath the Si surface layer. For the case of ISE SOI structures, described previously, the top layer is a substantially single-crystal recrystallized silicon, from which CMOS circuits can be fabricated. The use of a buried insulator provides devices having higher speeds than can be obtained in conventional bulk (Czochralski) material. However, it is noted that any number of techniques can be employed to provide a thin-film of single crystal Si.

Figure 21B:
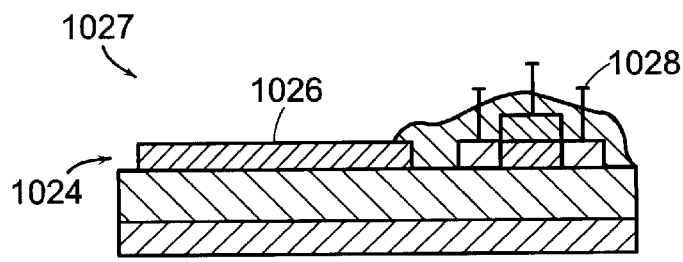
Figure 21C:
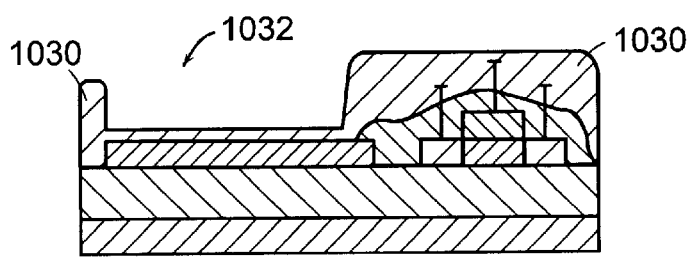

As shown in FIG. 21B, the film 1024 is patterned to define a pixel electrode region 1026 and a transistor region 1028 for each pixel element 1027. In one embodiment, the pixel electrode is formed of single crystal silicon. In another embodiment, the silicon is removed and indium tin oxide (ITO) is applied and patterned to form the pixel electrode. A transistor 1028 is then formed in accordance with any number of fabrication techniques, including those previously described herein. A thin layer of $SiN_2$ (not shown) is then formed over each pixel element. Next, a thin layer 1030 of optically transmissive material, such as $SiO_2$, is also formed over each pixel element 1027 and patterned to provide a well 1032 adjacent to each pixel electrode 1026 (FIG. 21C).

Figure 21D:
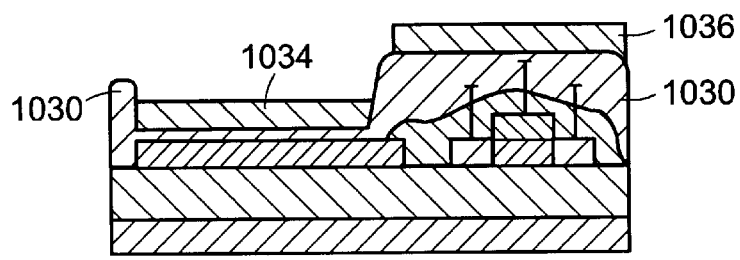

Referring to FIG. 21D, a color filter element 1034 is formed in the well 1032 adjacent to the thin film of essentially single crystal semiconductor material. Each color filter element 1034 is correlated with a pixel element 1027. The color filter elements can be formed by processing an emulsion or a photoresist carrier, as explained below, or by processing conventional filter materials. The individual color filter elements can be processed to provide an arrangement of three or four different color pixel elements in any of the previously described geometries. A matrix of opaque (or black) elements 1036 can also be formed adjacent to the thin film. Each opaque element 1036 is correlated with a pixel element 1027 serves to absorb light. A light shield for reflecting incident light and preventing the incident light from impinging upon the transistor 1028 associated with the pixel element can also be used. Such light shields are described in U.S. Ser. No. 07/823,858 filed on Jan. 22, 1992, which is incorporated herein by reference.

Figure 21E:
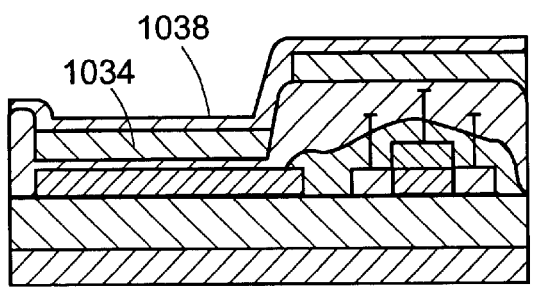
Figure 21F:
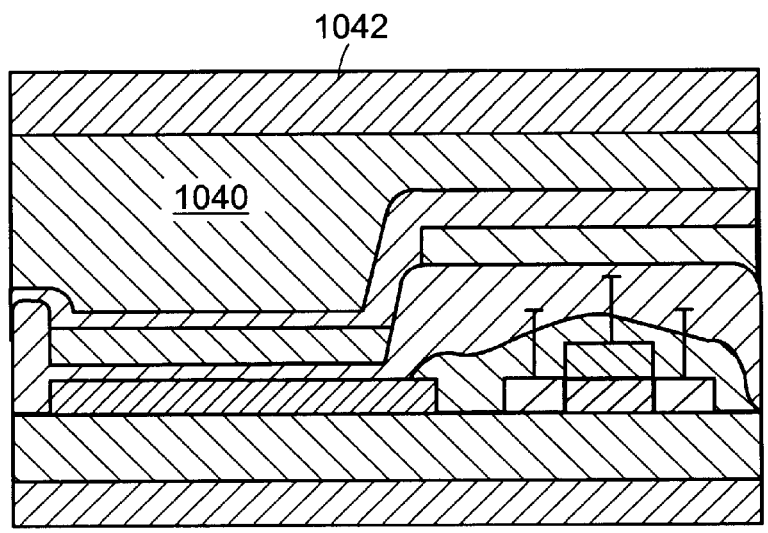

A thin optically transmissive layer 1038, which can be $SiO_2$, polyimide or sputtered glass, is formed over each pixel element (FIG. 21E). Referring to FIG. 21F, the active matrix structure is then transferred to an optically transmissive substrate 1042. To that end, an epoxy 1040 is used to attach an optically transmissive substrate 1042 to the active matrix and the color filter array. However, the optically transmissive layer 1038 isolates the color filter array from the epoxy 1040. The substrate 1020 (and optionally the oxide layer 1022) is removed and the epoxy 1040 is cured by heating the structure at about 160° C. for 24 hours.

Figure 21G:
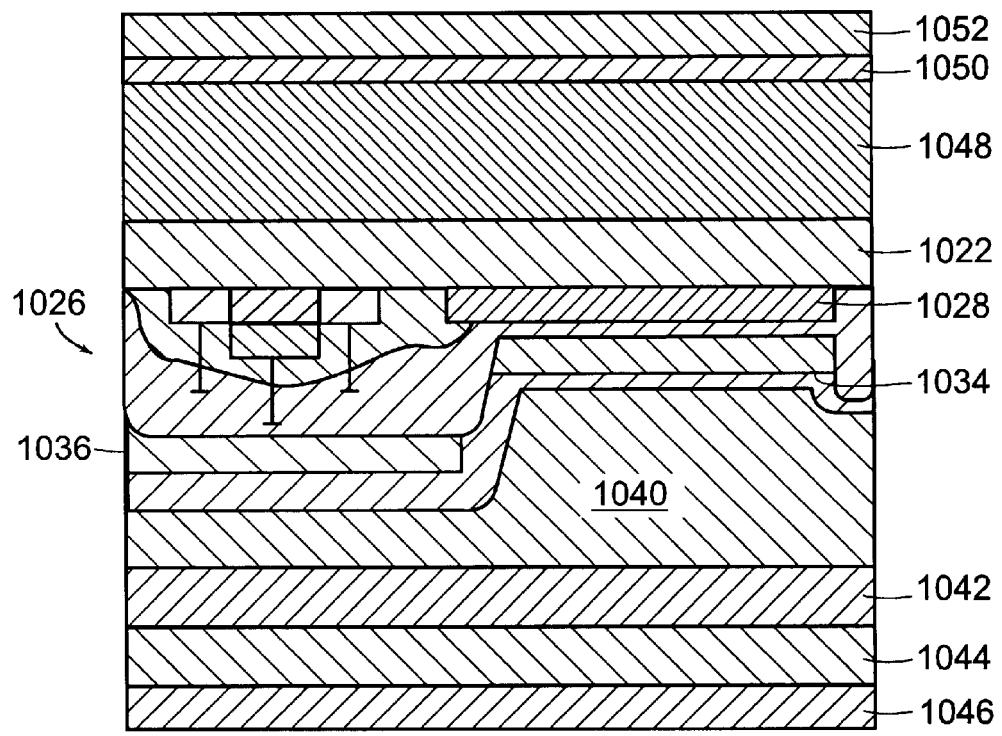

Referring to FIG. 21G, a cross-sectional view of the resulting display device is shown. Each pixel electrode 1028 and counterelectrode 1050 are laterally spaced from each other. Each pixel element 1027 will have a transistor 1028, a pixel electrode 1026 and an adjacent color filter element 1036 associated therewith. Polarizing elements 1052, 1044 are positioned on opposite sides of the structure which also includes the bonding element or adhesive 1040 and the optically transmissive substrate 1042, such as glass or plastic. The structure is completed by positioning a back light source 1046 adjacent to the polarizing element 1044.

Figure 22A:
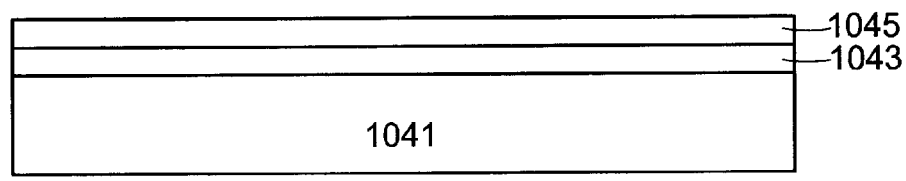
FIGS. 22A–22K is another preferred process flow sequence illustrating the fabrication of a transmissive active matrix color display.

FIGS. 22A–22K illustrate another preferred fabrication process for forming an active matrix color display. Referring to FIG. 22A, an SOI structure includes a silicon substrate 1041 and an insulating oxide layer 1043 (such as, for example, one micron of $SiO_2$) that is grown or deposited on the substrate 1041. A thin (i.e. 300 nm) single crystal layer 1045 of silicon is formed over the oxide 1043. The oxide is thus buried beneath the silicon surface layer, such that higher speed devices can be fabricated as explained previously. However, it is noted that any number of techniques can be employed to provide a thin film of single crystal silicon.

Figure 22B:
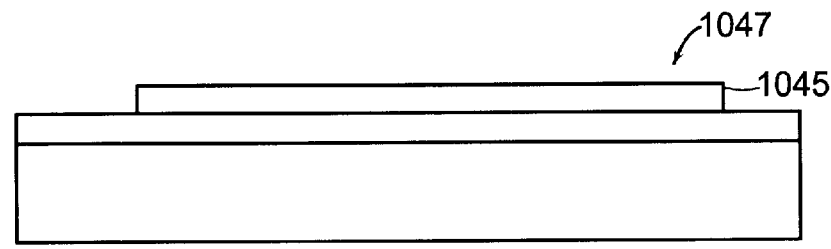
Figure 22C:
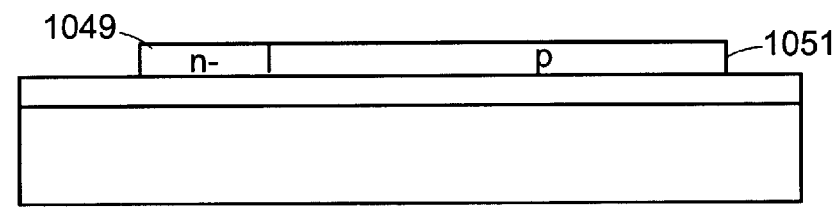

As shown in FIG. 22B, the film 1045 is patterned into islands to define each pixel element 1047. As explained below, the pixel elements are then processed to form a transistor and an electrode for each pixel. To that end, the pixel elements are masked (not shown) and subjected to deep and shallow implants to form an n-well region 1049 (FIG. 22C). Another masked is formed over the pixel elements, and the elements are subjected to deep and shallow implants to form an p-well region 1051.

Figure 22D:
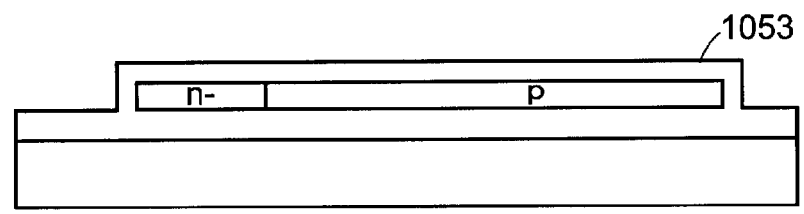
Figure 22E:
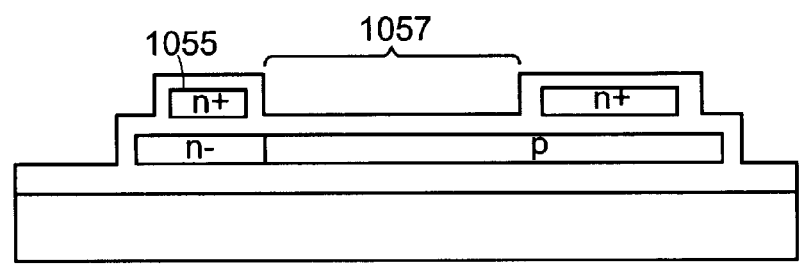

Referring to FIG. 22D, an $SiO_2$ layer 1053 having a thickness on the order of 70 nm is formed over each silicon island 1047. A layer of polysilicon having a thickness of about 500 nm is formed on the oxide layer 1053, doped to provide an n+ region and patterned to form a transistor gate 1055 (FIG. 22E). Another oxide layer 1057 having a thickness of about 70 nm is formed over the polysilicon.

Figure 22F:
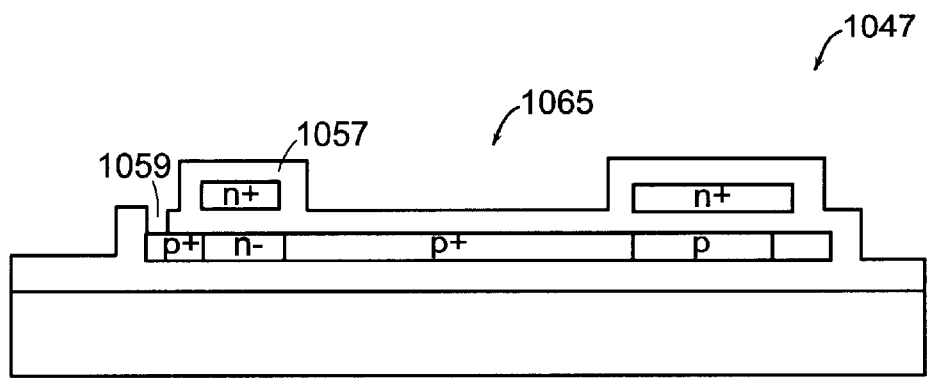

The pixel elements 1047 are masked (not shown) and doped with $2*10^{15}$ of phosphorus to provide an n+ source/drain implantation (FIG. 22F). After the mask is removed, the pixel elements are again masked and doped with $4*10^{15}$ of boron to provide a p+ source/drain implantation. As such, a transistor 1054 and a pixel electrode 1065 have been formed for each pixel element 1047.

Figure 22G:
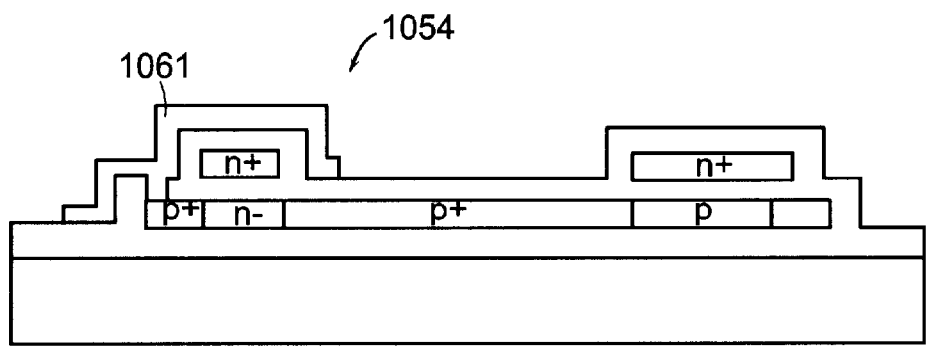

A portion 1059 of the oxide layer is then removed to form a contact for the transistor 1054. Referring to FIG. 22G, a metallization deposition is then performed to form a layer 1061 over the transistor 1054. The layer can comprise aluminum and has a thickness of about one micron. The layer 1061 serves as a pixel light shield as well as a contact for the transistor 1054.

Figure 22H:
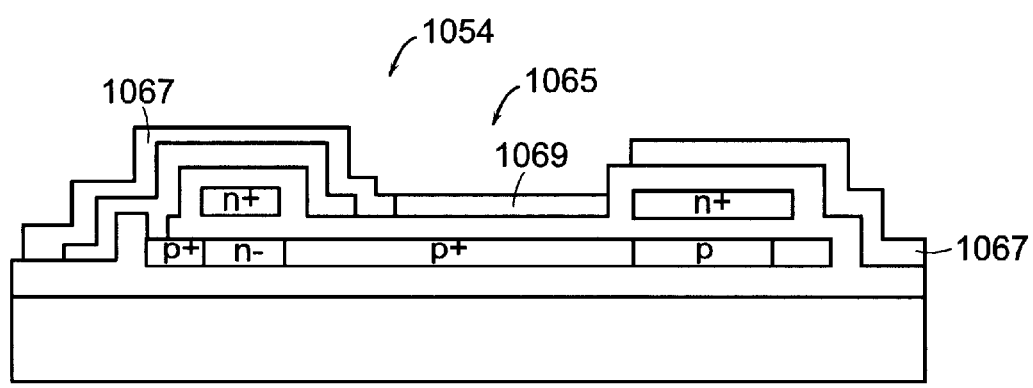

Referring to FIG. 22H, the entire pixel can be coated with a thin (about 150 nm) layer of silicon nitride (not shown). Next, a layer of amorphous silicon having a thickness of about 500 nm is deposited over each pixel element. The layer is then patterned to provide a matrix of black elements 1067, each black element associated with a transistor. A color filter element 1069 is formed over the pixel electrode 1065. The color filter elements can be formed by processing an emulsion or a photoresist carrier, as explained below, or by processing conventional filter materials. The individual color filter elements can be processed to provide an arrangement of three or four different color pixel elements in any of the previously described geometries.

Figure 22I:
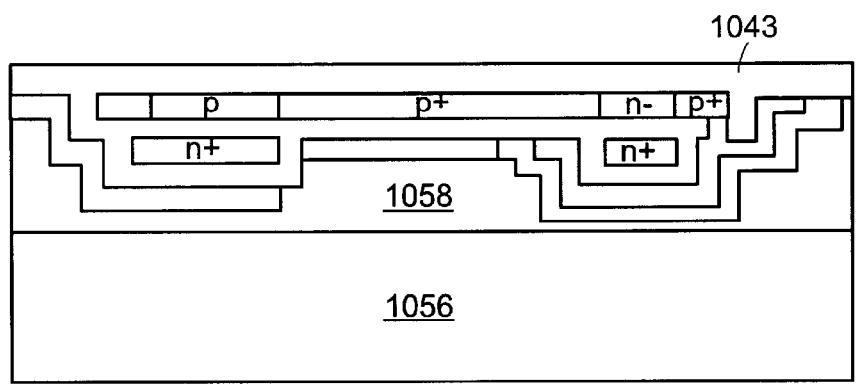

Referring to FIG. 22I, the active matrix structure is then transferred to an optically transmissive substrate 1056 such as glass or plastic. To accomplish this, an epoxy adhesive 1058 is used to attach an optically transmissive substrate 1056 to the active matrix structure. A thin optically transmissive layer (not shown), which can be $SiO_2$, polyimide or sputtered glass, can be formed over each pixel element (not shown) to isolate the color filter array from the epoxy 1058. The substrate 1041 (and optionally the oxide layer 1043) is removed and the epoxy 1058 is cured by heating the structure at about 160° C. for 24 hours.

Figure 22J:
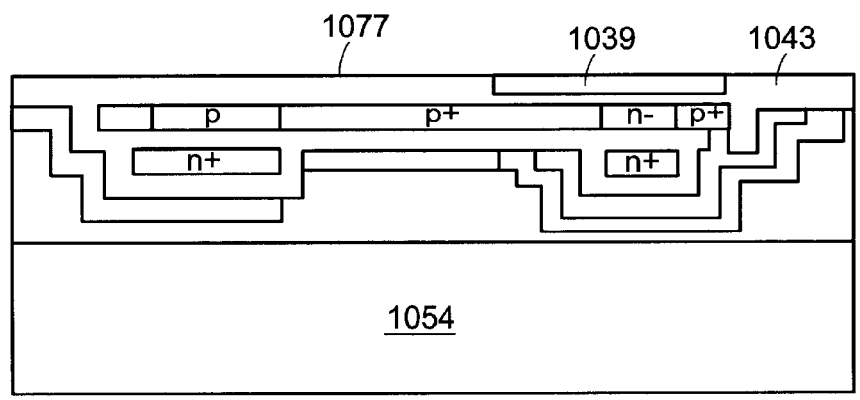

A second light shield 1039 is formed in or on the oxide layer 1043 as shown in FIG. 22J. In one embodiment, a metallization layer is formed on the oxide layer 1043 and patterned to form a light shield adjacent each transistor 1054. In another embodiment, the oxide layer 1043 is thinned adjacent to each transistor 1054. A light shield 1039 is formed in the thinned regions such that a substantially planar surface 1077 is provided adjacent to the liquid crystal material 1079 (FIG. 22K).

Figure 22K:
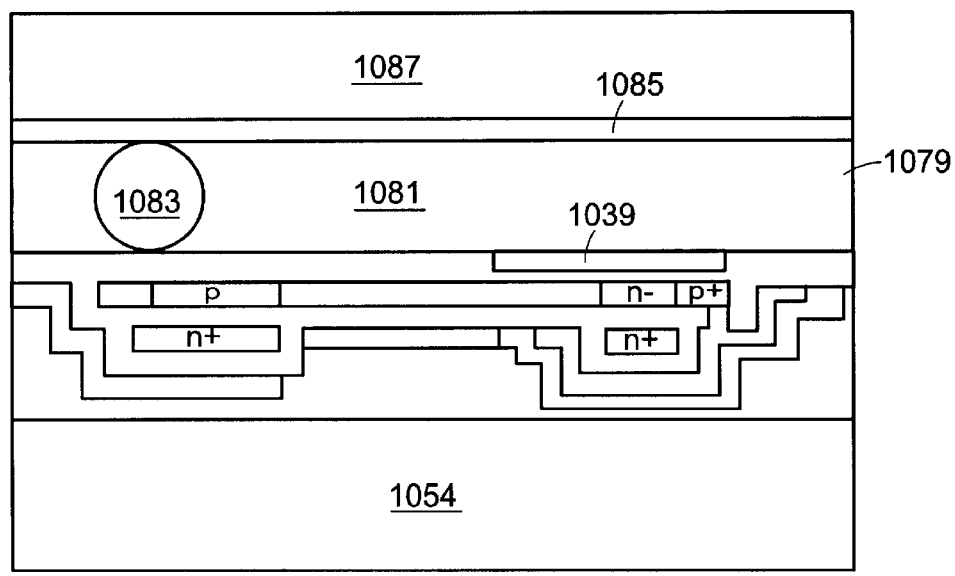

Referring to FIG. 22K, a liquid crystal material 1079 is disposed in a cavity 1081 along with spacers 1083. An ITO layer 1085, which serves as the counterelectrode, is formed adjacent to the cavity 1081. An optically transmissive layer 1087, such as glass or plastic, is positioned over the ITO layer.

Figure 23:
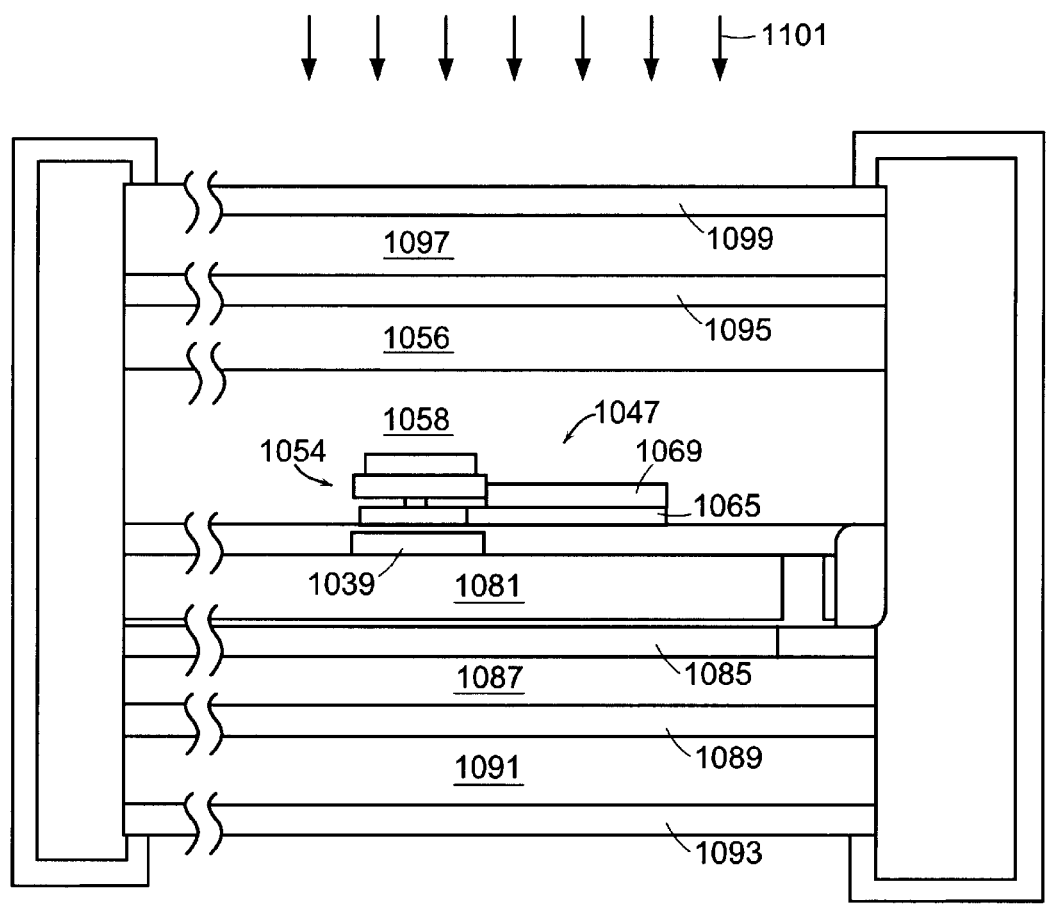
FIG. 23 is a cross-sectional view of the active matrix color display structure fabricated in accordance with FIGS. 22A–22K.

A partial cross-sectional view of the resulting active matrix color display device is shown in FIG. 23. Each pixel electrode 1065 is laterally spaced from the counterelectrode 1085. Each pixel element 1047 will have a transistor 1054, a pixel electrode 1065 and an adjacent color filter element 1069 associated therewith. Polarizing elements 1089, 1095 are positioned on opposite sides of the structure. The display also includes the bonding element or adhesive 1058, the optically transmissive substrate 1056, optically transmissive layers (1087, 1091, 1097) and ITO layers (1093, 1099). The structure is completed by positioning a light source for providing light 1101 adjacent to the ITO layer 1099.

In accordance with the present invention, an array of the color filter elements is formed adjacent to the array of pixel elements prior to transfer and subsequently transferred with the thin film and further processed to form an active matrix transmission display. In one preferred embodiment, a filter fabrication process using negative photoresist materials is employed to form an array of color filter elements.

FIGS. 24A–24J are sectional views illustrating the steps of forming an array of color filter elements in accordance with the this fabrication process.

Figure 24A:
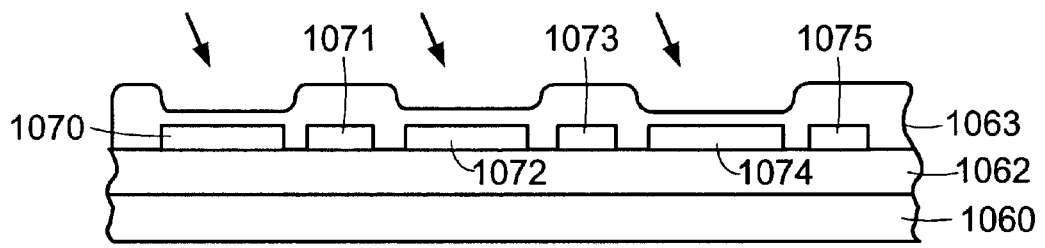
FIG. 24A–24H is a process flow sequence using negative photoresist materials for fabrication of an array of color filter elements.

Referring to FIG. 24A, an SOI structure includes a substrate 1060 and an oxide 1062 (such as, for example, $SiO_2$) that is grown or deposited on the substrate 1060. A thin single crystal layer 1054 of silicon is formed over the oxide 1062. The film 1063 is patterned into an array of pixel elements 1064, 1066, 1068. Each pixel element includes a pixel electrode region 1070, 1072, 1074 and a transistor region 1071, 1073, 1075 respectively for each pixel element.

Figure 24B:
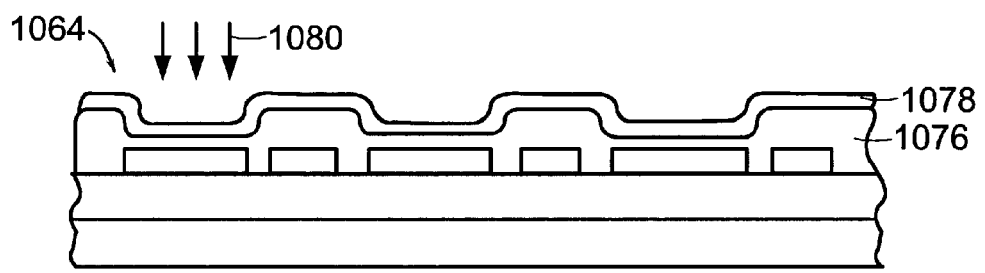
Figure 24C:
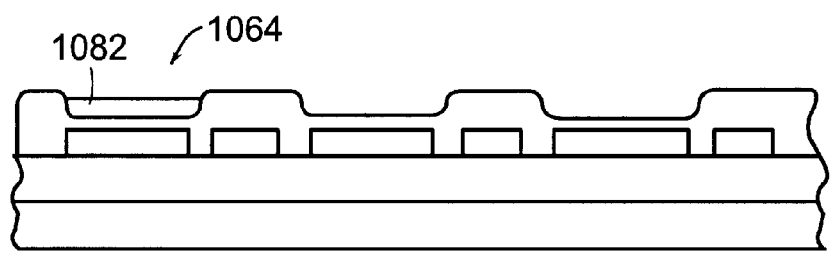

To form a first color filter on each of a first pixel element 1064, a pigment is dispersed in a negative resist material and applied as a film 1078 across an isolation layer 1076 (such as, for example, $SiO_2$) as shown in FIG. 24B. Such colored negative photoresist materials are commercially available. A portion of the film 1078 is exposed to a light 1080. The remainder of the film is masked (not shown) such that it is not exposed to the light 1080. The exposed portion of the film is developed in the presence of the light to form a first color filter element. The undeveloped portion of the film is removed, leaving a pattern of first color filter elements 1082 adjacent to each pixel 1064 (FIG. 24C).

Figure 24D:
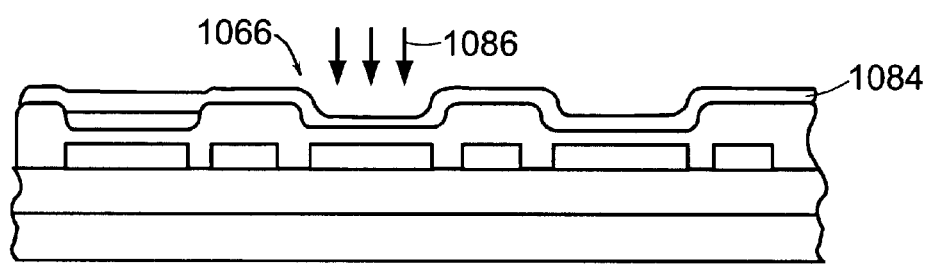
Figure 24E:
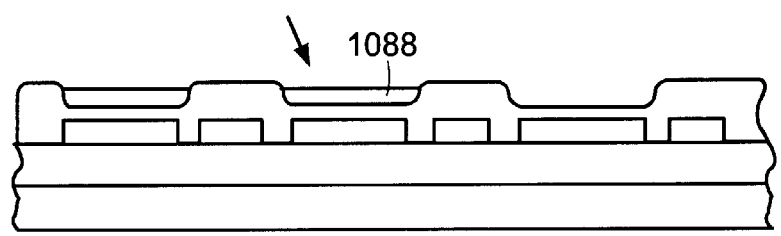

A second color filter element is formed in a similar manner as the first color filter elements 1082. Referring to FIG. 24D, a pigment is dispersed in a negative resist material and applied as a film 1084 across the isolation layer 1076 and the elements 1082. A portion of the film 1084 is exposed to a light 1086, while the remainder of the film is masked (not shown). The exposed portion of the film is developed in the presence of the light to form a second color filter element. The undeveloped portion of the film 1084 is removed, leaving a pattern of second color filter elements 1088 adjacent to each pixel 1066 (FIG. 24E).

Figure 24F:
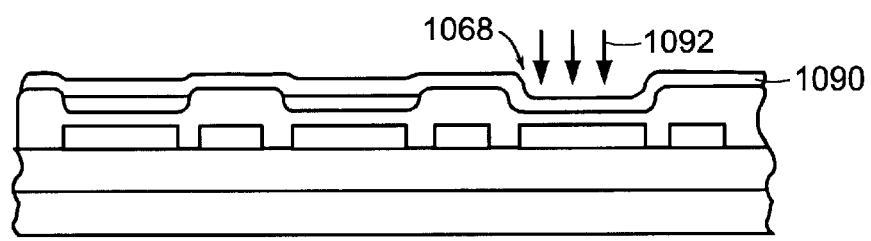
Figure 24G:
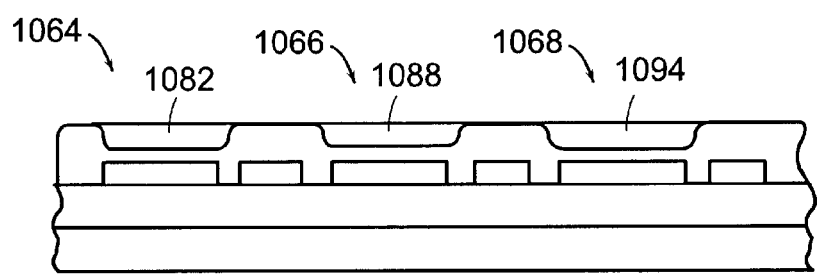
Figure 24H:
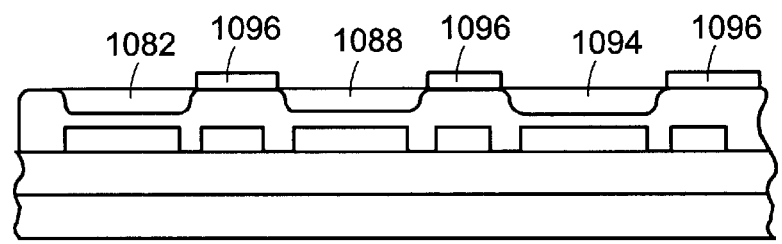

A third color filter element is formed in a similar manner as the first and second color filter elements 1082, 1088. Referring to FIG. 24F, a pigment is dispersed in a negative resist material and applied as a film 1090 across the isolation layer 1076 and the elements 1082, 1088. A portion of the film 1090 is exposed to a light 1092, while the remainder of the film is masked (not shown). The exposed portion of the film 1090 is developed in the presence of the light, and the undeveloped portion of the film 1084 is removed, leaving a pattern of third color filter elements 1094 adjacent to each pixel 1068 (FIG. 24G). optionally, a matrix array of opaque (or black) elements 1096 can be formed over or adjacent the transistor region of each pixel element 1064, 1066, 1068 as well as over the interprise spaces. Each opaque element 1096 serves to absorb light and provide a uniform background.

In other preferred embodiments, a color filter array is formed adjacent to the active matrix circuitry by applying a color photographic development process for each color. FIGS. 25A–25I illustrate in cross-sectional views a photographic development process which uses color-coupler containing developers. Referring to FIG. 25A, an SOI structure includes a substrate 1100 and an oxide 1102 (such as, for example, $SiO_2$) that is grown or deposited on the substrate. A thin single crystal layer 1104 of silicon is formed over the oxide 1102. The film 1104 is patterned into an array of pixel elements 1106, 1108, 1110. Each pixel element includes a pixel electrode region 1112, 1114, 1116 and a transistor region 1113, 1115, 1117 respectively for each pixel element.

Figure 25B:
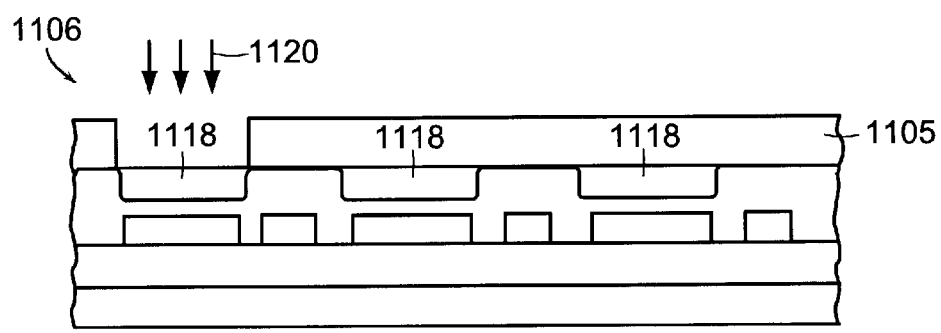
Figure 25C:
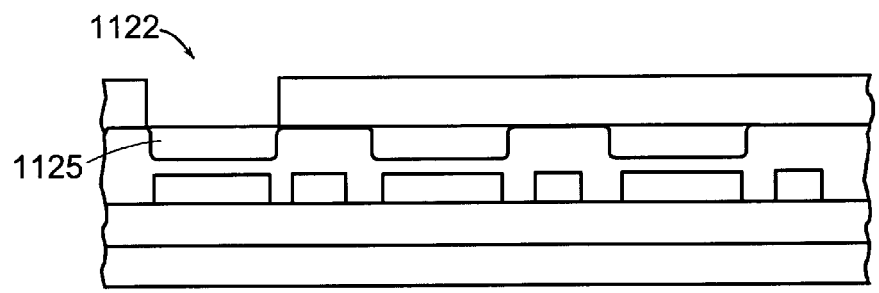
Figure 25D:
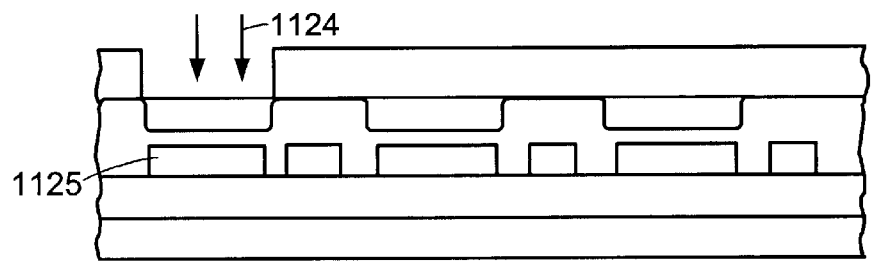

Referring to FIG. 25B, a black and white silver halide emulsion layer 1118 is formed adjacent to each pixel electrode of the active matrix. The formation of color filter elements utilizing a silver halide emulsion can be reviewed in greater detail in U.S. Pat. No. 4,400,454. An isolation layer 1105, such as $SiO_2$, is formed over the active matrix and patterned to expose the portion of the emulsion layer adjacent each first pixel 1106. This portion of the emulsion layer is exposed to light 1120 to provide silver particles. A first developer 1122 containing a color coupler is added to each exposed region 1125 of the emulsion layer (FIG. 25C). As such, a dye of a first color is then formed in each region 1125. Next, the silver is removed by bleaching or rehalogenating 1124 for each region 1125 as shown in FIG. 25D.

Figure 25E:
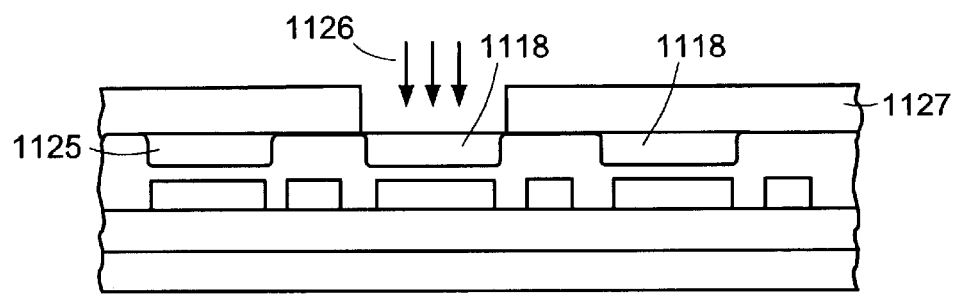
Figure 25F:
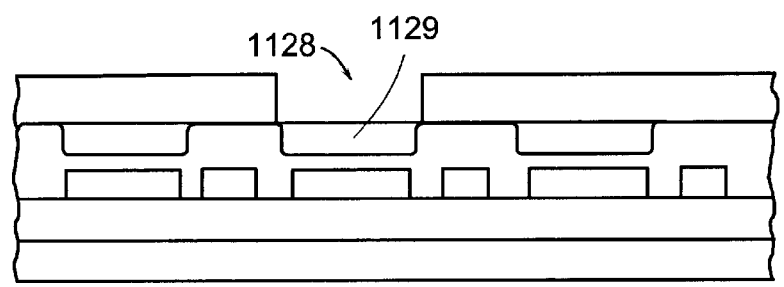
Figure 25G:
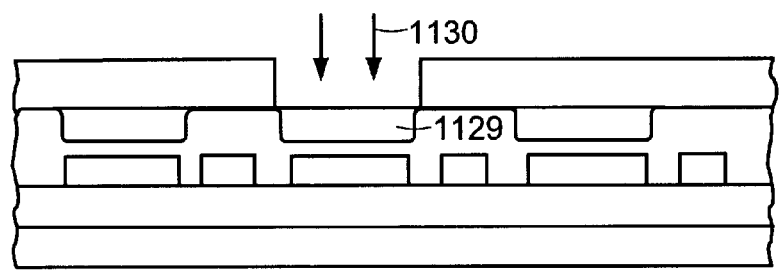

Referring to FIG. 25E, portions of the unexposed silver halide emulsion layer 1118 adjacent to each pixel 1108 are then exposed to light 1126 through a patterned isolation layer 1127 formed over the active matrix. A second developer 1128 containing a color coupler is added to each exposed region 1129 of the emulsion layer to form a dye of a second color in each region 1129 (FIG. 25F). Next, the silver is removed by bleaching or rehalogenating 1130 for each region 1129 as shown in FIG. 25G.

Figure 25H:
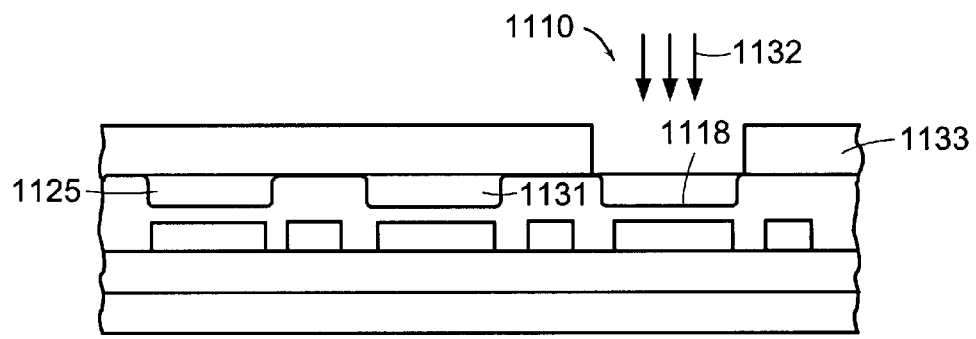
Figure 25I:
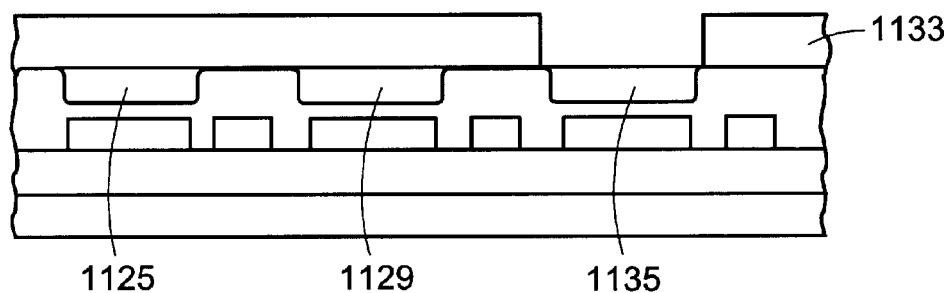
Figure 25J:
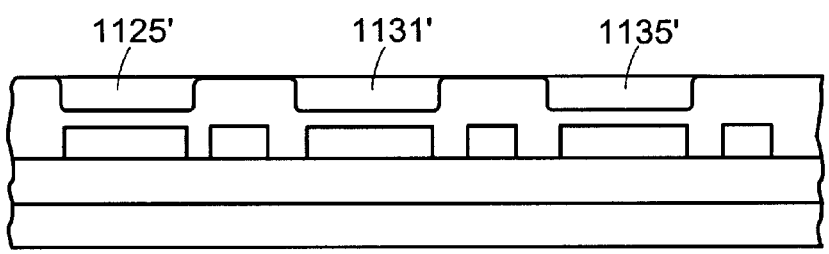

The remaining portions of the unexposed silver halide emulsion layer 1118 adjacent to pixels 1110 are then exposed to light 1132 through a patterned isolation layer 1133 (FIG. 25H). A third developer 1134 containing a color coupler is added to each exposed region 1135 of the emulsion layer to form a dye of a third color in each region 1135 (FIG. 25I). Next, the silver is removed by bleaching or rehalogenating 1130 for each region 1135. The layer 1133 is removed and any silver halide remaining in the emulsion layer is removed by fixing. As shown in FIG. 25J, an array of color filter elements 1125', 1131', 1135' are thus formed adjacent to each pixel.

Alternatively, a color filter array can be formed by applying a color photographic development process which uses developers containing dye developers. To accomplish this, the above-described process is performed using developers containing dye developers instead of developers containing color couplers. After processing such as that described in FIGS. 21–23, the thin film with the formed color filter elements can than be transferred, if necessary, for further processing prior to final display fabrication.

Figure 26A:
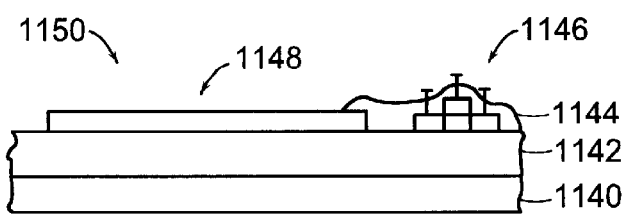
FIGS. 26A–26D is another preferred process flow sequence illustrating the fabrication of a transmissive active matrix color display.

FIGS. 26A–26D illustrate another preferred fabrication process for forming an active matrix color display. Referring to FIG. 26A, an SOI structure includes a substrate 1140 and an oxide 1142 (such as, for example, $SiO_2$) that is grown or deposited on the substrate 1140. A thin single crystal layer 1144 of silicon is formed over the oxide 1140 using any of the aforementioned fabrication techniques. For the case of ISE SOI structures, which were described previously, the top layer is a essentially single-crystal recrystallized silicon, from which CMOS circuits can be fabricated. The silicon thin film 1144 is patterned to define an array of pixel elements 1150. Each pixel element includes a pixel electrode region 1148 and a transistor 1146, formed in accordance with any number of fabrication techniques, including those previously described herein.

Figure 26B:
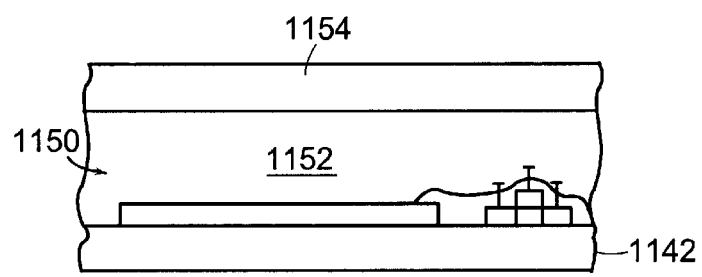

Referring to FIG. 26B, the active matrix structure is then transferred to an optically transmissive substrate 1154. To that end, an epoxy 1152 is used to attach an optically transmissive substrate 1154 to the active matrix. The substrate 1140 (and optionally the oxide layer 1142) is removed, and the epoxy 1152 is cured by heating the structure at about 160° C. for 24 hours.

Figure 26C:
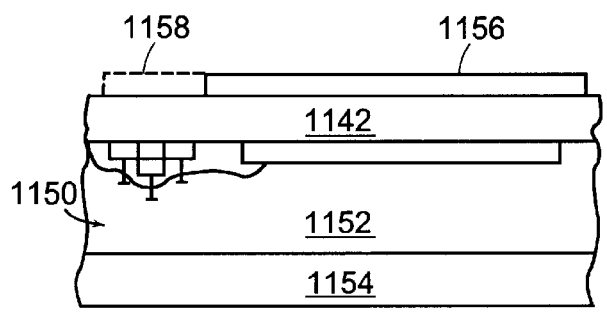

An array of color filter elements 1156 is formed on the oxide layer 1142 adjacent to planar surface of the thin film 1144 (FIG. 26C). Each color filter element 1156 is correlated with a pixel element 1150. The color filter elements 1156 are formed by processing, in accordance with the aforementioned processing techniques, an emulsion or photoresist carrier. The individual color filter elements can be processed to provide a display having a triad pixel arrangement of three primary (or non-primary) color filter elements. Alternatively, the color filter elements can be arranged into groups of four pixel elements. As noted previously, a primary color is defined herein to correspond to one of a group of colors which can be used to provide a spectrum of colors. An opaque (or black) element 1158 can also be formed adjacent to the thin film. Each opaque element 1158 is correlated with a pixel element 1150 and serves to prevent incident light from impinging upon the transistor 1146 associated with the pixel element.

Figure 26D:
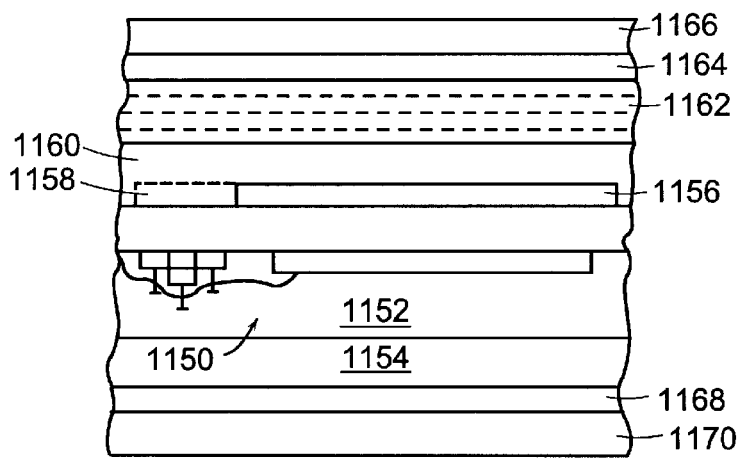

A cross-sectional view of the resulting active matrix display is shown in FIG. 26D. A liquid crystal material 1162 is positioned in close proximity to the pixel elements 1150. An insulating layer 1160, which can be $SiO_2$, polyimide or sputtered glass, is formed over each pixel element for passivating the pixel elements from the liquid crystal material 1162. A counterelectrode 1164 is laterally spaced from the pixel electrodes 1148. Each pixel element 1150 has a transistor 1146, a pixel electrode 1148 and an adjacent color filter element 1156 associated therewith. Polarizing elements 1164, 1168 are positioned on opposite sides of the structure. The structure is completed by positioning a back light source 1170 adjacent to the polarizing element 1168.

Figure 27:
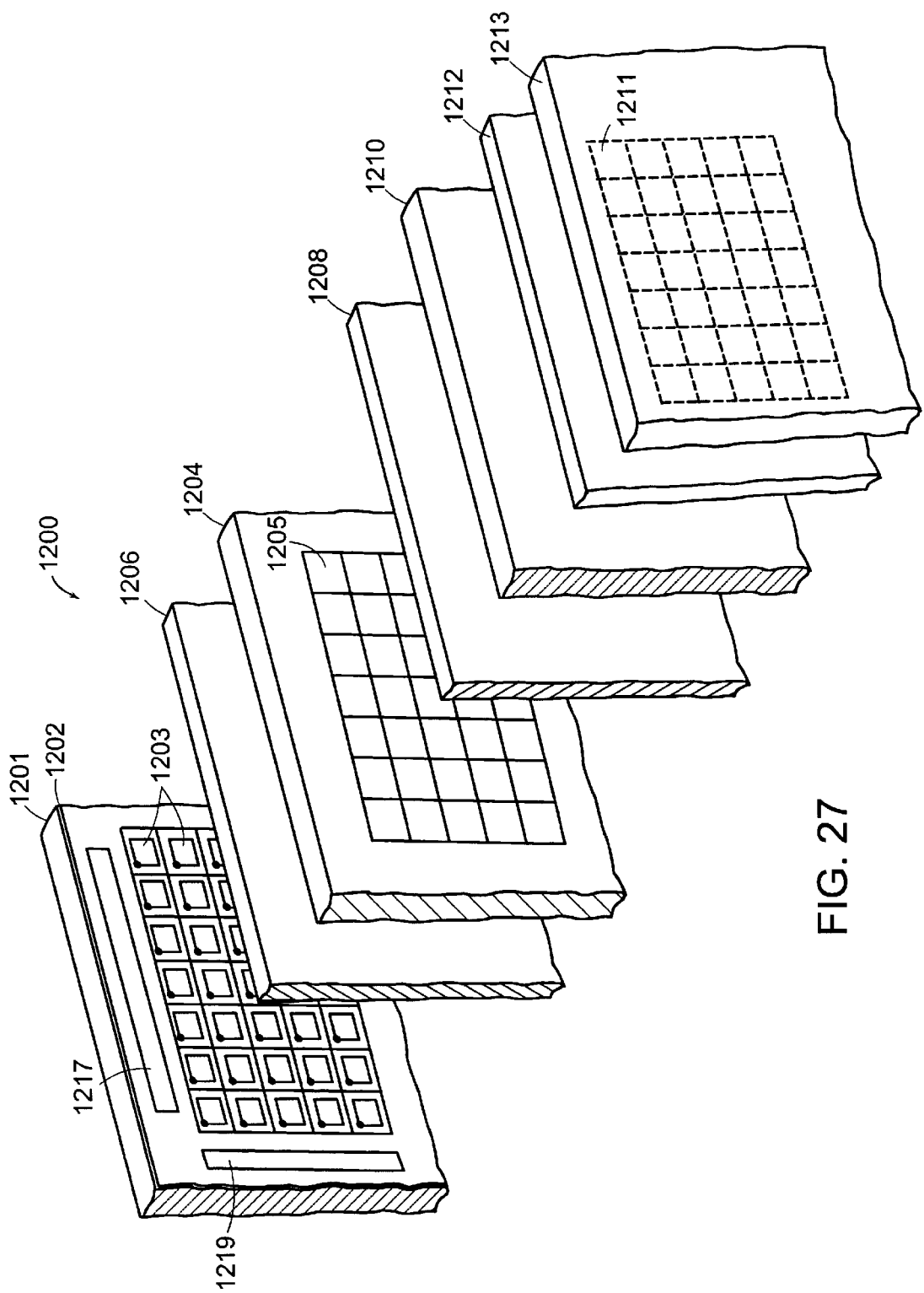
FIG. 27 is an exploded perspective view of an electroluminescent color display in accordance with the present invention.

Other preferred embodiments employ an emissive material (an electroluminescent film, light emitting diodes, porous silicon or any other light emitting material) in combination with a color filter array to form an emissive active matrix color display. To that end, an electroluminescent (EL) color display is shown in FIG. 27. The EL display 1200 is a layered structure which includes an active matrix circuit panel 1201, a bottom insulator 1206, an EL structure 1204, a top insulator 1208, an optically transmissive electrode 1210, a color filter array 1212 and an optically transparent superstrate 1213.

The EL structure is positioned between the two insulating layers 1206, 1208 for preventing destructive electrical breakdown by capacitively limiting direct current flow through the EL structure and for enhancing reliability. The insulators have a high electrical breakdown so that they can remain useful at high fields which are required to create hot electrons in the EL phosphor layers. The capacitive structure is completed by a pair of electrodes. One of these electrodes is pixel electrodes formed on the active matrix 1201 and the other electrode is the optically transmissive electrode 1210.

The EL structure 1204 is formed of a single phosphor layer which produces a white (or other multi-line spectrum) light in the presence of an applied field. The layer is patterned to provide an array of individual phosphor elements 1205. Each EL element 1205 is associated with a pixel element 1203. The color filter array 1212 is located in close proximity to the EL structure 1204 such that each color filter element 1211 is associated with an EL element 1205 and a pixel element 1203. The individual elements 1211 of color filter array can be arranged in a triad arrangement of three primary (or non-primary) color filter elements such as red, green and blue or yellow, cyan and magenta. Alternatively, the color filter elements can be arranged into groups of four different color filter elements such as red, green, blue and white or yellow, cyan, magenta and black/white.

The pixel elements 1203 of the active matrix 1201 are individually actuated by a CMOS/DMOS drive circuit, described previously herein or in a related application previously incorporated by reference, having first 1217 and second 1219 circuit components that are positioned adjacent the pixel array such that each pixel element can produce an electric field in an associated element 1205 of the EL structure 1204 between the pixel electrode and the transparent electrode 1210. The electric field causes the EL element 1205 to emit white light or other multi-line spectrum light. The light passes through the associated color filter element 1211 to produce a colored light which is illuminated from the display through the optically transmissive electrode 1210.

The active matrix pixel array employs transistors (TFTs) collocated with each pixel in the display to control the function of the pixel. As applied to EL displays, the active matrix approach offers significant advantages including reduced power dissipation in the circuit panel and increased frequency in which the AC resonant driver can operate. The formation of a useful EL active matrix requires TFTs that can operate at high voltages and high speeds. Single crystal silicon is preferred for achieving high resolution in a small (6 in×6 in or less) active matrix EL display.

In an EL display, one or more pixels are energized by alternating current (AC) which is provided to each pixel by row and column interconnects connected to the drive circuitry. The efficient conduction of AC by the interconnects is limited by parasitic capacitance. The use of an active matrix, however, provides a large reduction of the interconnect capacitance and can enable the use of high frequency AC to obtain more efficient electroluminescence in the pixel phosphor and increased brightness. In accordance with the present invention, the TFTs that provide this advantage are formed in a single crystal wafer, such as bulk Si wafers, or thin films or layers of single crystal or essentially single crystal silicon in accordance with the previously described fabrication techniques. These high quality TFTs are employed in an EL panel display, providing high speed and low leakage as well as supporting the high voltage levels needed for electroluminescence.

In preferred embodiments, single crystal silicon formed on an insulator (SOI) is processed to permit the formation of high voltage circuitry necessary to drive the EL display. More specifically, thin film single crystal silicon formed by the ISE process, or any of the other fabrication processes described herein, allows for fabrication of high voltage DMOS circuitry for the TFTs as well as low voltage CMOS circuitry for the drivers and other logic elements.

Figure 28A:
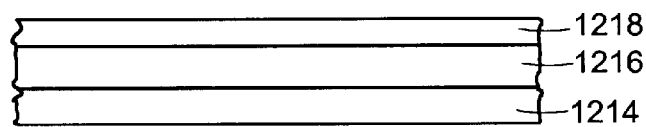
FIGS. 28A–28E is a preferred process flow sequence illustrating the fabrication of an electroluminescent active matrix color display.

A preferred fabrication sequence for the formation of an EL color display is shown in FIGS. 28A–28E. Referring to FIG. 28A, an SOI structure includes a substrate 1214 and an oxide 1216 (such as, for example, $SiO_2$) that is grown or deposited on the substrate 1214. A thin single crystal layer 1218 of silicon is formed over the oxide 1214. For the case of ISE SOI structures, the top layer is a substantially single-crystal recrystallized silicon, from which CMOS and DMOS circuits can be fabricated. The use of a buried insulator provides devices having better isolation than can be obtained in conventional bulk (Czochralski) material. However, it is noted that any number of techniques can be employed to provide a thin-film of single crystal silicon for an EL color display.

Figure 28B:
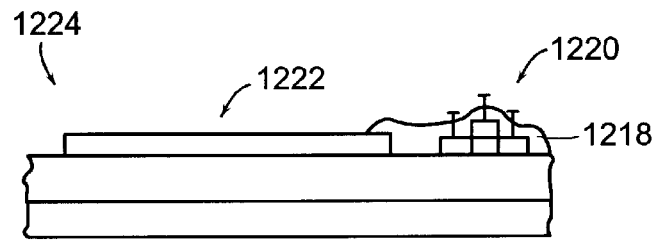
Figure 28C:
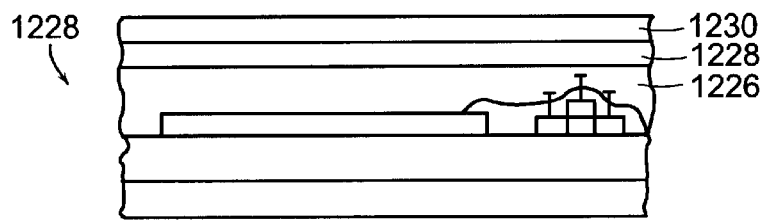

As shown in FIG. 28B, the film 1218 is patterned to define a pixel electrode region and a transistor region for each pixel element 1224. In one embodiment, the pixel electrode 1222 is formed of single crystal silicon. In another embodiment, the silicon is removed and ITO is applied and patterned to form the pixel electrode 1222. A transistor 1218 is then formed in accordance with any number of fabrication techniques, including those previously described herein. Next, the EL structure is formed (FIG. 28C). To that end, a thin layer 1226 of insulating material is deposited and patterned over each pixel element 1224. A white phosphor layer 1228 is deposited and patterned over the bottom insulator 1226, and a top insulator 1230 is deposited and patterned over the phosphor material.

Figure 28D:
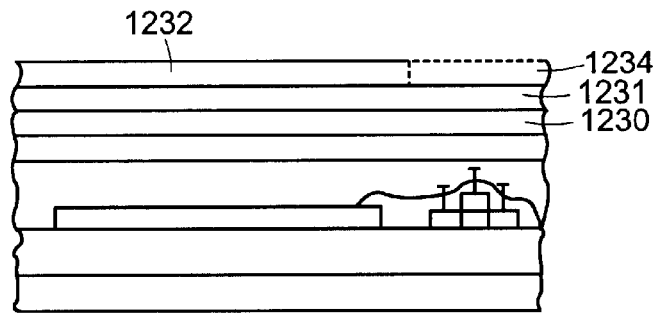
Figure 28E:
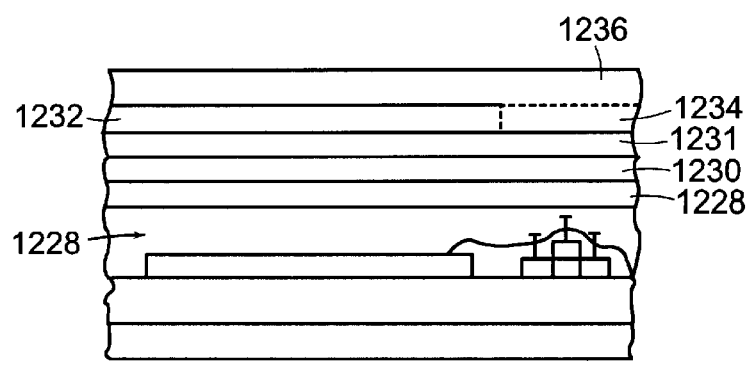

Referring to FIG. 28D, a top electrode 1231 is formed on the EL structure. Next, a color filter element 1232 is formed. Each color filter element 1232 is correlated with a phosphor element 1228 and a pixel element 1224 such that each pixel is capable of producing light of a primary color. As explained previously, the color filter elements are formed by processing an emulsion or a photoresist carrier. The individual color filter elements 1232 can be processed to provide a triad arrangement of primary color pixels such as blue, green and red or yellow, cyan and magenta. In another embodiment, the color filter elements can be processed to provide a triad (or quad) arrangement of non-primary color pixels. In yet another embodiment, the color filter elements can be arranged into groups of four pixel elements. An opaque element 1234 can also be formed adjacent to the EL material. Each opaque element 1234 is correlated with a pixel element 1224 and absorbs light for preventing incident light from impinging upon the transistor 1220 associated with the pixel element. A optically transmissive superstrate 1236 such as glass or plastic is formed over the EL structure to complete the EL color display (FIG. 28E).

Figure 29A:
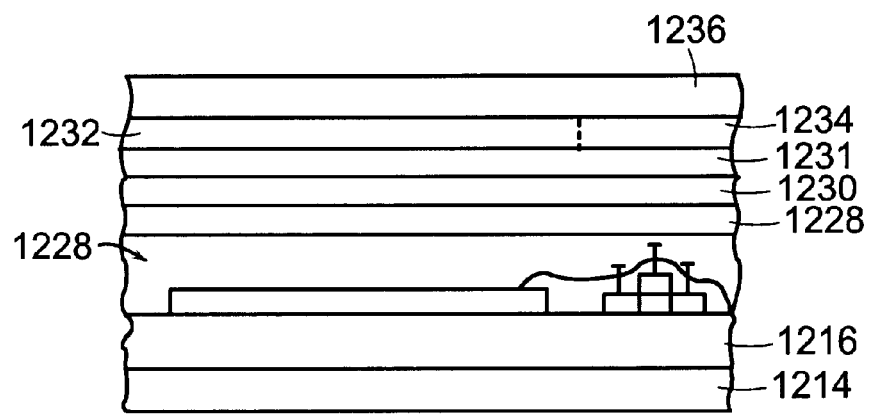
FIGS. 29A–29C is a preferred process flow sequence illustrating the transfer of an electroluminescent active matrix color display to an optically transmissive substrate.
Figure 29B:
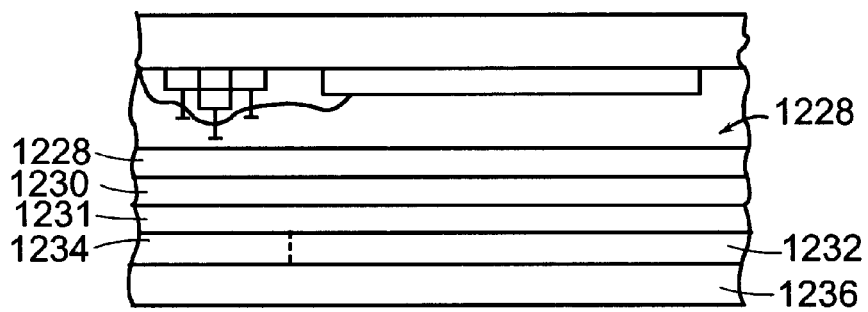
Figure 29C:
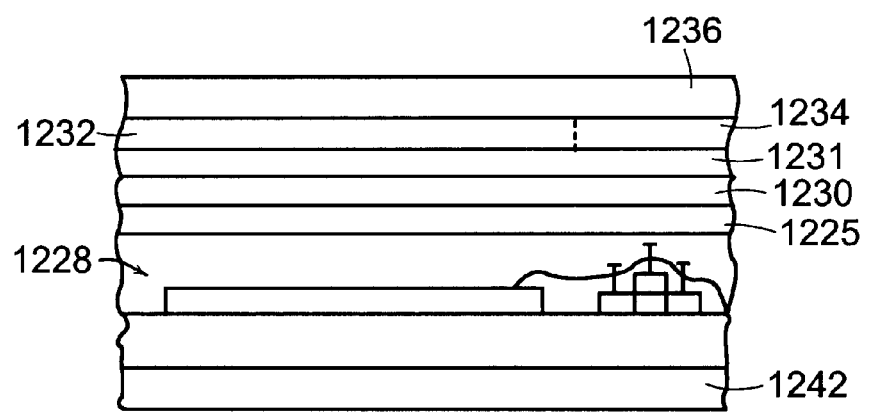

In another embodiment, the EL color display can be transferred to an optically transmissive substrate as illustrated in FIGS. 29A–29C. An EL display fabricated in accordance with any of the previously described methods is shown in FIG. 29A.

The structure is inverted and the initial substrate 1214 is removed (FIG. 29B). The structure is then transferred to an optically transmissive substrate 1242, such as glass or a curved surface of a visor, and the superstrate 1236 is optionally removed.

Figure 30:
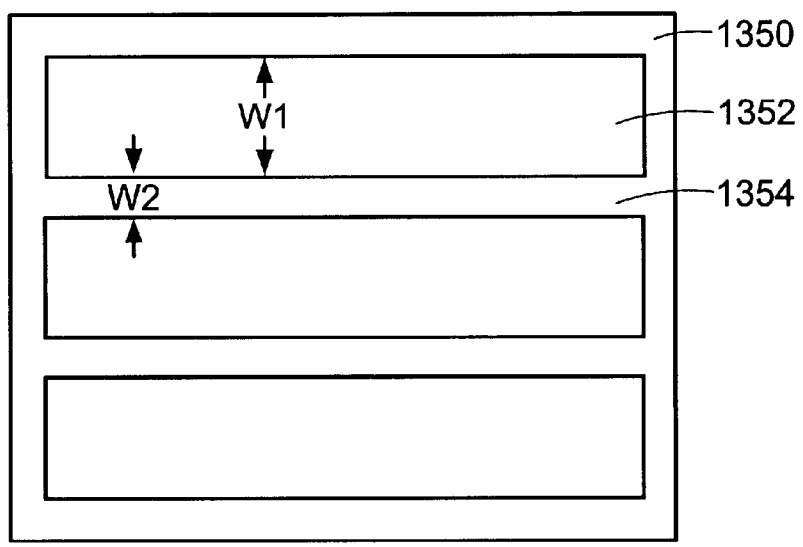
FIG. 30 is an illustration of a patterned pixel electrode element.

Another feature of the active matrix displays of the present invention is that an array of pixel electrode elements can be patterned in the single crystal silicon material. In one preferred embodiment, the individual pixel electrode elements are solid shaped elements formed of single crystal silicon or indium tin oxide (ITO). In another embodiment, the pixel electrodes can be selectively thinned to optimize transistor performance. Regions of the electrode can be thinned to about one-tenth the thickness of the 0.1 to 2.0 micron single crystal silicon layer. In yet another embodiment, the silicon material is patterned to form an array of pixel electrodes and each electrode is further patterned into a grid, serpentine, or other suitable geometry to reduce transmission loss through the pixel electrode. Referring to FIG. 30, an individual pixel electrode 1350 initially comprises a solid layer of single crystal silicon. However, the element is processed such that areas 1352 of silicon are removed and strips 1354 of silicon remain. As such, the resulting pixel electrode resembles a grid. The open areas 1352 have a width (W1) of about 3–5 microns and the strips 1354 have a width (W2) of about 1–2 microns. This provides an aperture through each pixel electrode that improves transmission of light by reducing interference effects and also reducing reflection, absorption and scattering caused by the pixel material. One advantage of the grid-shaped pixels is the increased light transmission through the active matrix which results in brighter displayed images. Another advantage is that the grid-shaped pixels minimize thickness variations in the single crystal silicon layer. These thickness variations cause light absorption and/or interference which reduces the light transmission through the active matrix. By minimizing thickness variations, brighter displayed images can be provided. An alternative embodiment includes further thinning of the pixel electrode material so that the switching circuits are within a thicker film than the pixel electrode.

Figure 31:
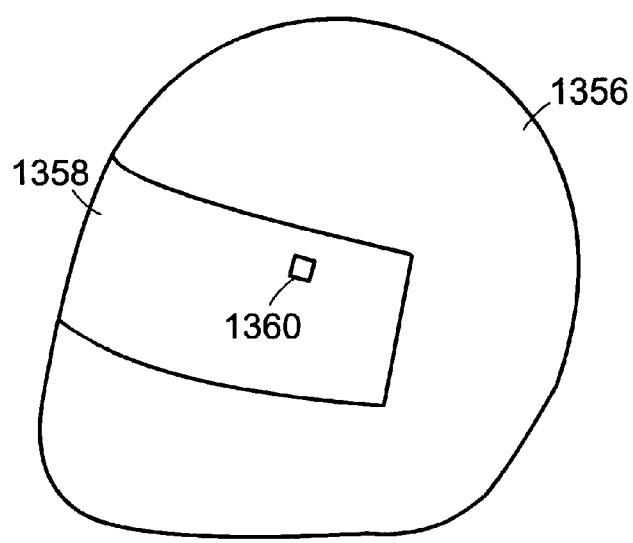
FIG. 31 is an illustration of a head-mounted active matrix display system.

Yet another feature of the active matrix displays described herein is that they may be mounted on a visor of a helmut to form a head-mounted display. Referring to FIG. 31, a visor 1358 formed of optically transmissive material is secured onto a helmut 1356. An active matrix display 1360 is positioned on the visor 1358. When activated by an electronics system (not shown), the display 1360 generates monochrome or multi-color images which are projected into the helmut 1356 for viewing by a subject. The display 1360 is substantially transparent when inactive.

Figure 32:
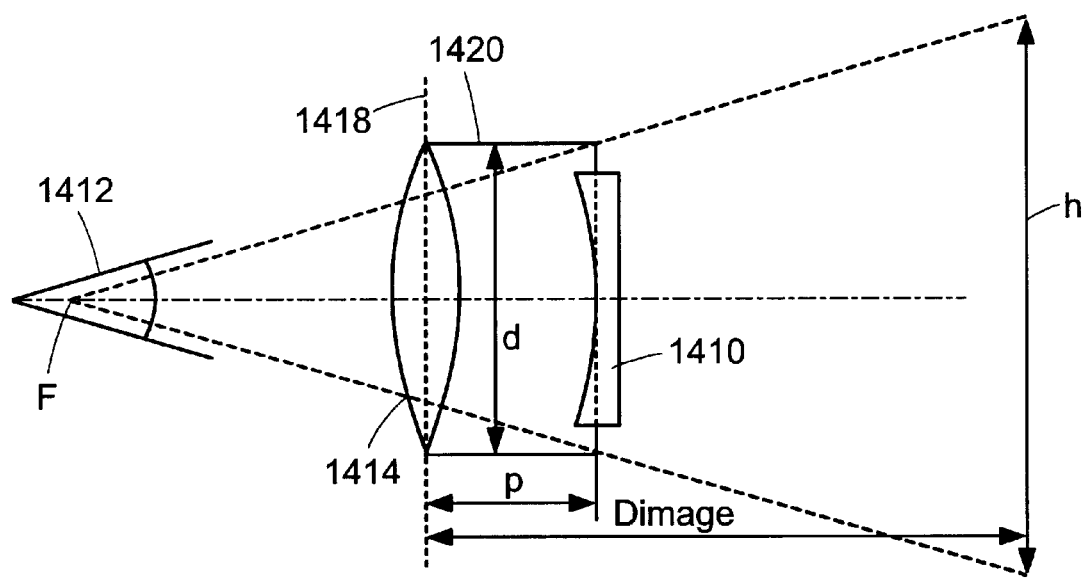
FIG. 32 shows a schematic illustration of a head mounted display system.

A preferred embodiment of the invention is illustrated in the direct view, helmet mounted display system of FIG. 32. An active matrix single crystal silicon display device 1410 is mounted in close proximity to the eye 1412. The fabrication of such active matrix displays 1410 has been described in great detail in the above. A lens 1414 is used to deliver a focussed image to the eye. Lens 1414 has a given thickness and a diameter d. Table 3, that is appended hereto, lists characteristics of commercially available lens including diameter, F# and center thickness. Other lenses having the desired dimensions are easily manufactured to provide the thickness and focal length necessary.

TABLE 3

| Diam. in. (mm) | Nom. f @ 589 nm (mm) | Nom. BFL @ 589 nm (mm) | F/# | Ctr. Thk. (mm) | Edge Thk. (mm) |
|---|---|---|---|---|---|
| 0.5 (12.7) | 11 | 9 | 0.8 | 5.7 | 1.34 |
| | 13.7 | 12.2 | 1.0 | 4.3 | 1.1 |
| | 16.6 | 15.4 | 1.3 | 3.6 | 1.1 |
| | 20.5 | 19.5 | 1.5 | 3.1 | 1.1 |
| | 26.4 | 25.6 | 2.0 | 2.6 | 1.1 |
| | 38.4 | 37.7 | 3.0 | 2.1 | 1.1 |
| | 51.3 | 50.7 | 4.0 | 2.0 | 1.2 |
| 1.0 (25.4) | 20 | 18 | 0.8 | 11.0 | 2.3 |
| | 27.4 | 24.6 | 1.0 | 8.2 | 1.8 |
| | 33 | 30.7 | 1.3 | 6.7 | 1.6 |
| | 39 | 37 | 1.5 | 5.8 | 1.6 |
| | 51.7 | 50.2 | 2.0 | 4.7 | 1.6 |
| | 63.6 | 62.3 | 2.5 | 4.0 | 1.6 |
| | 76.6 | 75.2 | 3.0 | 4.0 | 1.9 |
| | 101.6 | 100.3 | 4.0 | 4.0 | 2.4 |
| 1.5 (38.1) | 34.4 | 29.4 | 0.85 | 14.0 | 1.9 |
| | 40 | 36 | 1.0 | 12.0 | 2.1 |
| | 52.5 | 49.4 | 1.3 | 9.1 | 2.0 |
| | 64.2 | 61.7 | 1.7 | 7.5 | 1.8 |
| | 77 | 74.8 | 2.0 | 6.5 | 1.8 |
| | 101.8 | 100 | 2.6 | 5.3 | 1.8 |
| | 127.2 | 125.6 | 3.3 | 5.0 | 2.2 |
| 2.0 (50.8) | 42 | 34.2 | 0.8 | 21.0 | 2.4 |
| | 53.6 | 48.4 | 1.0 | 15.0 | 2.0 |
| | 65 | 61 | 1.2 | 12.0 | 1.7 |
| | 77.8 | 74 | 1.5 | 11.0 | 2.6 |
| | 102 | 100 | 2.0 | 8.3 | 2.0 |
| | 127.6 | 125.3 | 2.5 | 7.0 | 2.0 |
| | 176.5 | 174.4 | 3.5 | 6.4 | 2.8 |

The distance from the center axis 1418 of lens 1414 to the display 1410 is denoted by p. The active matrix display has a high pixel density so as to match the resolution of the human eye. By increasing the resolution, or the density of pixels in the active matrix display 1410, and at the same time reduce the size of the display it is possible to position the display closer to the eye.

Where the distance P is less than 2.5 centimeters, the pixel density is at least 200 lines per centimeter and preferably over 400 lines per centimeters to provide the desired resolution.

Where P=1.5 centimeters, the display 1410 is about 1.27 centimeters in diameter and has a pixel density of about 400 lines per centimeter. The focal length $F_L$ between the lens 14 and focal point F is generally defined by the expression:

$$\frac{1}{F_L} = \frac{1}{P} + \frac{1}{D_{IMAGE}}$$

Solving for the distance to the image we obtain $$D_{IMAGE} = \left(\frac{1}{F_L} - \frac{1}{P}\right)^{-1}$$

As the human eye will optimally focus an image at a distance of about 400 centimeters (about 15 feet), and as the focal length of the lens is preferably small enough to focus the image onto the eye over a short distance, the diameter of the lens should be less than 3 centimeters and preferably under 2.0 centimeters.

The following table defines the relationship between lens diameter d, and the distance between the lens and the display P in accordance with the invention where $D_{IMAGE}$ is about 400 centimeters:

| Lens Diameter, d | Object Distance P (all in cm) |
|---|---|
| 0.6 | 0.48 |
| 0.8 | 0.64 |
| 1 | 0.80 |
| 1.2 | 0.96 |
| 1.4 | 1.12 |
| 1.6 | 1.28 |
| 1.8 | 1.43 |
| 2 | 1.59 |
| 2.2 | 1.75 |
| 2.4 | 1.91 |
| 2.6 | 2.07 |
| 2.8 | 2.23 |
| 3 | 2.39 |

The above summarizes the preferred elements of a head mounted display where the active matrix display and lens system are mounted in close proximity to the eye.

The following embodiment comprises a simple optical approach to attain a brightness increase of up to 100% by reducing a common parasitic loss. This loss obtains in all liquid crystal display light valves at the first polarizing filter, which attenuates one half of the unpolarized light emanating from the lamp. In other words, the light source of the display generates light of two polarizations; one polarization (half of the light) is absorbed by the polarizing filter to make it suitable for modulation by the liquid crystal.

Figure 33:
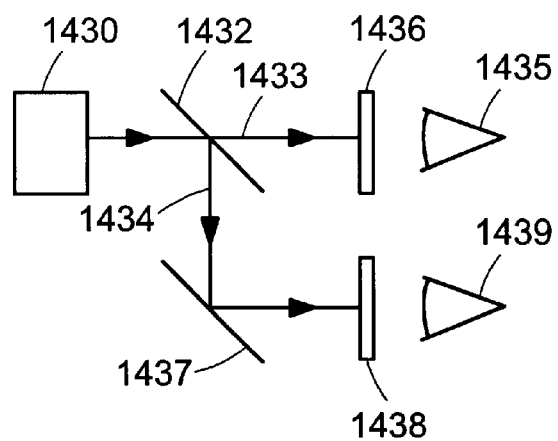
FIG. 33 illustrates a preferred embodiment of a head mounted display where two components of polarized light are separated for improved optical efficiency.

In this embodiment, as shown in FIG. 33, the light from source 1430 is polarized, not by a polarizing filter, but by a Brewster polarizing window 1432 which passes one polarization 1433 only to light valve 1436. The other polarization 1434 is reflected, at window 1432 and reflected again at mirror 1437 and directed to a second light valve 1438. There are at least two implementations of this invention, as follows:

In a head-mounted display the Brewster window 1432 can be used to pass polarized light, TE polarized for example, to the right eye 1435 light valve liquid crystal display 1436. The reflected light, TM polarized in this example, is passed to the left eye 1439 light valve liquid crystal display 1438. Neither light valve requires a "first" polarizer that is described in the parent application referenced above, although the presence of one introduces only a slight reduction in fluence since the light is already polarized. Thus, substantially all of the incident light is passed to the liquid crystal, leading to near doubling of the optical efficiency. of course, the liquid crystal in the left and right liquid crystal display must be rotated 90° with respect to each other to account for the polarization of the TE and TM polarizations of the light. The absence of a "first" polarizing filter can reduce the cost of the display.

Figure 34:
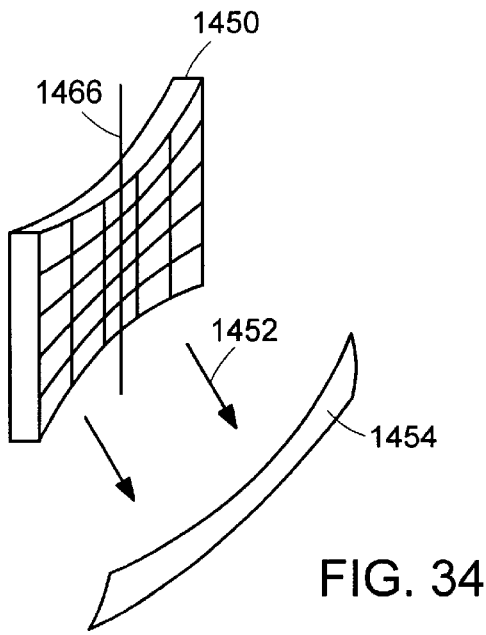
FIG. 34 illustrates an active matrix for a wide angle field of view head mounted display system.

Another preferred embodiment of the invention is illustrated in FIG. 34. In this embodiment the active matrix 1450 is fabricated where the pixel geometry and pixel area is variable as a function of the position of the pixel within the matrix. This provides a wide angle field of view image that can be projected onto the internal surface of the face shield 1454 of the head mounted display.

FIG. 35 illustrates a detailed view of a portion of the active matrix surface area. Pixels 1460, 1462, 1464 and 1468 have an increasing surface area as the distance from the pixel to the matrix center 1466 axis is increased. The distance between adjacent column lines and between adjacent row lines also increases as a function of the distance from center axis 1466. The matrix can be a backlit transmission display or an emission type display as described in more detail in U.S. Ser. No. 07/944,207 filed on Sep. 11, 1992. The active matrix can be formed on a first substrate and transferred onto either a flat or curved substrate prior to mounting onto the optical support assembly of the helmet. The active matrix can also be transferred to a flat substrate that is subjected to a low temperature anneal in the rang of 300–400 degrees F and preferably at about 350 degrees F that will provide a desired curvature to the active matrix.

A further embodiment is illustrated in FIG. 36 wherein separate active matrix display elements 1470, 1472, 1474 etc. are mounted or tiled onto a plastic visor screen 1476. The visor screen can be polycarbonate, polyethylene or polyester material. Each display element 1470, 1472, 1474 can have driver circuitry 1482, 1480, 1478, respectively, formed separately on the edge. The tiling process is described in detail in the above referenced related U.S. Applications that have been incorporated herein by reference.

Equivalents

While this invention has been particularly shown and described with reference to preferred embodiments thereof, it will be understood by those skilled in the art that various changes in form and details may be made therein without departing from the spirit and scope of the invention are defined by the appended claims.

What is claimed is:

1. A display system for viewing by a user's eye comprising:
  a support frame that can be positioned adjacent a user's head;
  an active matrix liquid crystal display mounted on the support frame to direct an image emitted from a display surface onto the user's eye and having a plurality of row address lines and a plurality of column address lines, the active matrix display further comprising an array of pixel circuits and an array of pixel electrodes, each pixel circuit being formed with a thin film of single crystal silicon and being electrically connected to one row address line and one column address line, such that there are at least 200 row address lines per centimeter and 200 column address lines per centimeter, the array of pixel electrodes defining an image area having a diameter of 2.5 centimeters or less, each pixel electrode in a column of pixel electrodes being connected to a different row address line;
  a driver circuit formed with the thin film of single crystal silicon that is connected to the array of pixel circuits and that drives the display;
  a battery that provides power to the display;
  a backlight source positioned adjacent to the active matrix display that directs light along an axis to the user's eye; and
  a lens mounted to the support frame and positioned between the active matrix display and the user's eye along the axis to direct an image from the display onto the user's eye, the lens being less than 2.54 centimeters from the display surface and having a diameter of less than 3 centimeters.

2. The head mounted display system of claim 1 wherein the active matrix display further comprises at least 1000 row address lines.

3. The head mounted display system of claim 1 wherein the lens comprises a center axis and is positioned such that the lens center axis is 1.52 centimeters or less from the display surface.

4. The head mounted display system of claim 1 wherein the active matrix display is positioned to direct an image onto the user's left eye and further comprising a second active matrix display mounted on the support frame such that the second active matrix display directs light onto the user's right eye.

5. The head mounted display system of claim 1 further comprising a row driver circuit and a column driver circuit in the thin film of single crystal silicon.

6. The head mounted display system of claim 1 wherein the display comprises a color liquid crystal display.

7. A display system for viewing by a user's eye comprising:
  a support frame that can be positioned adjacent a user's head;
  an active matrix display mounted on the support frame to direct an image emitted from a display surface onto the user's eye and having a plurality of row address lines and a plurality of column address lines, the active matrix display further comprising an array of pixel circuits and an array of pixel electrodes, each pixel circuit being formed in a thin film of single crystal silicon and being electrically connected to one row address line and one column address line, such that there are at least 400 row address lines per centimeter and 400 column address lines per centimeter, the array of pixel electrodes defining an image area having a diameter of 2.5 centimeters or less, each pixel electrode being connected to a different row address line; and
  a driver circuit formed with the thin film of single crystal silicon that is connected to the array of pixel circuits and that drives the display;
  a battery that provides power to the display; and
  a lens positioned between the active matrix display and the user's eye to focus an image from the display onto the user's eye, the lens being less than 2.54 centimeters from the display surface and having a diameter of less than 3 centimeters.

8. The head mounted display system of claim 7 wherein the lens comprises a center axis and is positioned such that the lens center axis is 1.5 centimeters or less from the display surface.

9. The head mounted display system of claim 7 wherein the active matrix display is positioned to direct an image onto the user's left eye and further comprising a second active matrix display mounted on the support frame such that the second active matrix display directs light onto the user's right eye.

10. The head mounted display system of claim 7 further comprising a row driver circuit and a column driver circuit in the thin film of single crystal silicon.

11. The head mounted display system of claim 7 wherein the display comprises a color liquid crystal display.

12. A display system for viewing by a user's eye comprising:
- a support frame that can be positioned adjacent a user's head;
- an active matrix liquid crystal display mounted on the support frame to direct an image emitted from a display surface onto the user's eye and having a plurality of row address lines and a plurality of column address lines, the active matrix display further comprising an array of pixel circuits and an array of pixel electrodes, each pixel circuit being formed with a thin film of single crystal silicon and being electrically connected to one row address line and one column address line, such that there are at least 200 row address lines per centimeter and 200 column address lines per centimeter, the array of pixel electrodes defining an image area having a diameter of 1.27 centimeters or less, each pixel electrode in a column of pixel electrodes being connected to a different row address line;
- a driver circuit formed with the thin film of single crystal silicon that is connected to the array of pixel circuits and that drives the display;
- an antenna and a receiver that is electrically connected to the antenna and the display, and that receives image data from a remote source;
- a backlight source positioned adjacent to the active matrix display that directs light along an axis to the user's eye;
- a battery that provides power to the display; and
- a lens mounted to the support frame and positioned between the active matrix display and the user's eye along the axis to direct an image from the display onto the user's eye, the lens being less than 2.54 centimeters from the display surface and having a diameter of less than 3 centimeters.

13. The head mounted display system of claim 12 wherein the active matrix display further comprises at least 1000 row address lines.

14. The head mounted display system of claim 12 wherein the lens comprises a center axis and is positioned such that the lens center axis is 1.52 centimeters or less from the display surface.

15. The head mounted display system of claim 12 wherein the active matrix display is positioned to direct an image onto the user's left eye and further comprising a second active matrix display mounted on the support frame such that the second active matrix display directs light onto the user's right eye.

16. The system of claim 15 wherein the driver circuit compress a row driver circuit and a column driver circuit in the thin film of single crystal silicon.

17. The display system of claim 15 wherein the display comprises a color liquid crystal display.

18. A display system for viewing by a user's eye comprising:
- a display housing;
- an active matrix liquid crystal display mounted within the housing to direct an image emitted from a display surface onto the user's eye and having a plurality of row address lines and a plurality of column address lines, the active matrix display further comprising an array of pixel circuits and an array of pixel electrodes, each pixel circuit being formed with a single crystal silicon material and being electrically connected to one row address line and one column address line, such that there are at least 200 row address lines per centimeter and 200 column address lines per centimeter and each pixel electrode in a column of pixel electrodes being connected to a different row address line;
- a driver circuit formed with the thin film of single crystal silicon that is connected to the array of pixel circuits and drives the display;
- a battery within the housing that provides power to the display;
- a light source that directs light onto the active matrix display; and
- a lens positioned between the active matrix display and the user's eye along a viewing axis to direct an image from the display onto the user's eye, the lens being less than 2.54 centimeters from the display surface and having a diameter of less than 3 centimeters.

19. The display system of claim 18 wherein the active matrix display further comprises at least 1000 row address lines.

20. The display system of claim 18 wherein the lens has a center axis and is positioned such that the lens center axis is 1.52 centimeters or less from the display surface.

21. The display system of claim 18 wherein the active matrix display is positioned to direct an image onto the user's left eye and further comprising a second active matrix display mounted on the user's head such that the second active matrix display directs light onto the user's right eye.

22. The display system of claim 18 further comprising a row driver circuit and a column driver circuit in the thin film of single crystal silicon.

23. The display system of claim 18 wherein the display comprises a color liquid crystal display.

24. The display system of claim 18 further comprising a wireless receiver.

25. The display system of claim 18 wherein the system comprises an antenna.

* * * * *

UNITED STATES PATENT AND TRADEMARK OFFICE
CERTIFICATE OF CORRECTION

| | | |
|---|---|---|
| PATENT NO. | : 7,075,501 B1 | Page 1 of 1 |
| APPLICATION NO. | : 08/384237 | |
| DATED | : July 11, 2006 | |
| INVENTOR(S) | : Mark B. Spitzer, Ronald Gale and Jeffrey Jacobsen | |

It is certified that error appears in the above-identified patent and that said Letters Patent is hereby corrected as shown below:

Col. 29, line 2, Claim 12, delete "eve" and insert -- eye --
Col. 29 line 49, Claim 16, delete "The system" and insert -- The head mounted display system --
Col. 29, line 52, Claim 17 delete "The display system" and insert -- The head mounted display system --

Signed and Sealed this

Twenty-first Day of November, 2006

JON W. DUDAS
*Director of the United States Patent and Trademark Office*